(12) United States Patent
Suzuki et al.

(10) Patent No.: US 10,947,193 B2
(45) Date of Patent: Mar. 16, 2021

(54) CATIONIC LIPID

(71) Applicant: EISAI R&D MANAGEMENT CO., LTD., Tokyo (JP)

(72) Inventors: Yuta Suzuki, Ibaraki (JP); Yoshinori Takahashi, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/897,752

(22) Filed: Jun. 10, 2020

(65) Prior Publication Data

US 2020/0308111 A1 Oct. 1, 2020

Related U.S. Application Data

(63) Continuation of application No. PCT/JP2018/047440, filed on Dec. 25, 2018.

(30) Foreign Application Priority Data

Dec. 27, 2017 (JP) .............................. JP2017-251870

(51) Int. Cl.
C07D 207/16 (2006.01)

(52) U.S. Cl.
CPC .................................. *C07D 207/16* (2013.01)

(58) Field of Classification Search
CPC .................................................... C07D 207/16
See application file for complete search history.

(56) References Cited

U.S. PATENT DOCUMENTS

| | | |
|---|---|---|
| 8,158,601 B2 | 4/2012 | Chen et al. |
| 9,873,669 B2 | 1/2018 | Suzuki et al. |
| 2010/0324120 A1 | 12/2010 | Chen et al. |
| 2011/0256175 A1 | 10/2011 | Hope et al. |
| 2012/0027803 A1 | 2/2012 | Manoharan et al. |
| 2012/0183602 A1 | 7/2012 | Chen et al. |
| 2013/0178541 A1 | 7/2013 | Stanton et al. |
| 2013/0195920 A1 | 8/2013 | Maier et al. |
| 2015/0133519 A1 | 5/2015 | Colletti et al. |
| 2015/0166465 A1 | 6/2015 | Chen et al. |
| 2015/0273068 A1 | 10/2015 | Maier et al. |
| 2015/0306039 A1 | 10/2015 | Akinc et al. |
| 2015/0361434 A1 | 12/2015 | Stanton et al. |
| 2016/0009637 A1 | 1/2016 | Manoharan et al. |
| 2016/0317458 A1 | 11/2016 | Brito et al. |
| 2016/0326116 A1 | 11/2016 | Suzuki et al. |
| 2016/0367638 A1 | 12/2016 | Byers et al. |
| 2017/0135962 A1 | 5/2017 | Colletti et al. |
| 2017/0143631 A1 | 5/2017 | Chen et al. |
| 2017/0233734 A1 | 8/2017 | Akinc et al. |
| 2017/0334852 A1 | 11/2017 | Suzuki et al. |
| 2018/0193279 A1 | 7/2018 | Colletti et al. |

FOREIGN PATENT DOCUMENTS

| | | |
|---|---|---|
| CN | 103167866 | 6/2013 |
| JP | 2012-530059 | 11/2012 |
| JP | 2013-533224 | 8/2013 |
| RU | 2014141547 | 5/2016 |
| WO | WO 2010/042877 | 4/2010 |
| WO | WO 2010/144740 | 12/2010 |
| WO | WO 2011/153493 | 12/2011 |
| WO | WO 2012/040184 | 3/2012 |
| WO | WO 2012/061259 | 5/2012 |
| WO | WO 2013/059496 | 4/2013 |
| WO | WO 2013/086354 | 6/2013 |
| WO | WO 2013/135360 | 9/2013 |
| WO | WO 2013/158579 | 10/2013 |
| WO | WO 2014/089239 | 6/2014 |
| WO | WO 2015/095346 | 6/2015 |
| WO | WO 2015/095351 | 6/2015 |
| WO | WO 2015/105131 | 7/2015 |
| WO | WO 2016/104580 | 5/2020 |

OTHER PUBLICATIONS

Examination Report in Australian Patent Application No. 2017282459, dated Sep. 22, 2020, 4 pages.
Response to Office Action in Israeli Patent Application No. 262574, dated Oct. 8, 2020, 4 pages (with English Translation).
Decision to Grant a Patent in Japanese Patent Application No. 2015-556822, dated Jul. 31, 2018, 6 pages (with English Translation).
Decision to Grant a Patent in Japanese Patent Application No. 2016-566429, dated Sep. 3, 2019, 6 pages (with English Translation).
Extended European Search Report in European Patent Application No. 15735252.7, dated Jun. 8, 2017, 6 pages.
Extended European Search Report in European Patent Application No. 15873148.9, dated May 4, 2018, 7 pages.
Extended European Search Report in European Patent Application No. 17815482.9, dated Jan. 22, 2020, 5 pages.

(Continued)

*Primary Examiner* — Laura L Stockton
(74) *Attorney, Agent, or Firm* — Fish & Richardson P.C.

(57) ABSTRACT

The present invention provides a cationic lipid which is able to be used for nucleic acid delivery to the cytoplasm. A cationic lipid according to the present invention is, for example, a compound represented by formula (1) or a pharmaceutically acceptable salt thereof, wherein $L_1$ and $L_2$ independently represent an alkylene group having 3 to 10 carbon atoms; $R_1$ and $R_2$ independently represent an alkyl group having 4 to 24 carbon atoms or an alkenyl group having 4 to 24 carbon atoms; $R_3$ represents an alkyl group having 1 to 3 carbon atoms; and $X_1$ represents a single bond or CO—O—.

(1)

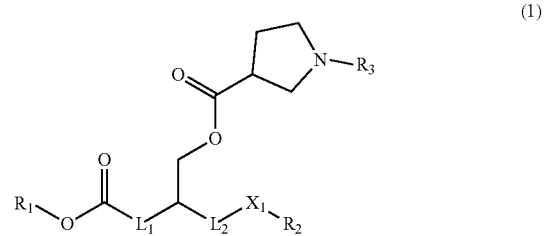

14 Claims, 2 Drawing Sheets

Specification includes a Sequence Listing.

(56) References Cited

OTHER PUBLICATIONS

Gindy, M.E. et al., "Stabilization of Ostwald Ripening in Low Molecular Weight Amino Lipid Nanoparticles for Systemic Delivery of siRN A Therapeutics," Mol. Pharmaceutics, (2014), 11: 4143-4153.
Intention to Grant in European Patent Application No. 15873148.9. dated Oct. 19, 2018, 99 pages.
International Preliminary Report on Patentability in International Application No. PCT/JP2015/050295, dated Jul. 12, 2016, 7 pages (with English Translation).
International Preliminary Report on Patentability in International Application No. PCT/JP2017/023052, dated Feb. 12, 2019, 13 pages (with English Translation).
International Search Report and Written Opinion in International Application No. PCT/JP2015/050295, dated Feb. 17, 2015, 11 pages (with English Translation).
International Search Report and Written Opinion in International Application No. PCT/JP2015/085969, dated Mar. 15, 2016, 15 pages (with English Translation).
International Search Report and Written Opinion in International Application No. PCT/JP2017/023051, dated Sep. 5, 2017, 13 pages (with English Translation).
International Search Report and Written Opinion in International Application No. PCT/JP2018/047440, dated Feb. 19, 2019, 16 pages (with English Translation).
Jayaraman, M. et al., "Maximizing the Potency of siRNA Lipid Nanoparticles for Hepatic Gene Silencing in Vivo," Angew. Chem. Int. Ed., (2012), 51:8529-8533.
Notice of Allowance in Chinese Patent Application No. 201580003735.2, dated Jul. 10, 2018, 4 pages (with English Translation).
Notice of Allowance in Taiwanese Patent Application No. 104143612, dated May 6, 2020, 6 pages (with English Translation).
Notice of Allowance in U.S. Appl. No. 15/109,512, dated Sep. 18, 2017, 7 pages.
Notice of Allowance in U.S. Appl. No. 15/841,652, dated Oct. 1, 2018, 10 pages.
Notice of Allowance in U.S. Appl. No. 16/307,202, dated Aug. 1, 2019, 6 pages.
Notice of Allowance in U.S. Appl. No. 16/307,202, dated May 30, 2019, 11 pages.
Notice of Allowance in U.S. Appl. No. 16/307,202, dated Sep. 19, 2019, 9 pages.
Office Action in Chinese Patent Application No. 201580003735.2, dated Dec. 21, 2017, 6 pages (with English Translation).
Office Action in Chinese Patent Application No. 201580003735.2, dated May 27, 2017, 10 pages (with English Translation).
Office Action in Chinese Patent Application No. 201580068712.X, dated Sep. 6, 2018, 13 pages (with English Translation).
Office Action in European Patent Application No. 15735252.7, dated Jul. 12, 2018, 70 pages.
Office Action in Japanese Patent Application No. 2016-566429, dated Apr. 23, 2019, 6 pages (with English Translation).
Office Action in Taiwanese Patent Application No. 104100437, dated Aug. 31, 2018, 6 pages (with English Translation).
Office Action in Taiwanese Patent Application No. 104143612, dated Oct. 2, 2019, 7 pages (with English Translation).
Office Action in U.S. Appl. No. 15/109,512, dated May 19, 2017, 34 pages.
Office Action in U.S. Appl. No. 15/841,652, dated May 18, 2018, 8 pages.
Official Notification to Grant in Chinese Patent Application No. 201580068712.X, dated Mar. 12, 2019, 4 pages (with English Translation).
Official Notification to Grant in Taiwanese Patent Application No. 104100437, dated Nov. 27, 2018, 6 pages (with English Translation).
Response filed in Chinese Patent Application No. 201580003735.2, dated Feb. 28, 2018, 10 pages (with English Translation).
Response filed in Chinese Patent Application No. 201580003735.2, dated Sep. 25, 2017, 5 pages (with English Translation).
Response filed in Chinese Patent Application No. 201580068712.X, dated Nov. 14, 2018, 27 pages (with English Translation).
Response filed in European Patent Application No. 15873148.9, dated Aug. 17, 2018, 93 pages.
Response filed in Japanese Patent Application No. 2016-566429, dated Aug. 9, 2019, 12 pages (with English Translation).
Response filed in Taiwanese Patent Application No. 104100437, dated Nov. 16, 2018, 16 pages (with English Translation).
Response to European Extended Search Report in European Patent Application No. 17815482.9, dated May 19, 2020, 3 pages.
Response to Office Action in Taiwanese Patent Application No. 104143612, dated Dec. 26, 2019, 29 pages (with English Translation).
Response to Office Action in U.S. Appl. No. 15/109,512, dated Aug. 16, 2017, 10 pages.
Response to Office Action in U.S. Appl. No. 15/841,652, dated Jul. 24, 2018, 3 pages.
Response to Restriction Requirement in U.S. Appl. No. 15/109,512, dated May 10, 2017, 3 pages.
Response to Restriction Requirement in U.S. Appl. No. 15/841,652, dated Mar. 22, 2018, 3 pages.
Restriction Requirement in U.S. Appl. No. 15/109,512, dated Mar. 13, 2017, 8 pages.
Restriction Requirement in U.S. Appl. No. 15/841,652, dated Jan. 30, 2018, 6 pages.
Suzuki et al., "Biodegradable lipid nanoparticles induce a prolonged RNA interference-mediated protein knockdown and show rapid hepatic clearance in mice and nonhuman primates," International Journal of Pharmaceutics, vol. 519, No. 1-2, Jan. 9, 2017, pp. 34-43.
Wan et al., "Lipid nanoparticle delivery systems for siRNA-based therapeutics," Drug Delivery and Translational Research, Spring, (2013), Germany, 4(1):74-83.
Office Action and Search Report in Russian Patent Application No. 2018143237, dated Jul. 24, 2020, 9 pages (with English Translation).
Office Action in Israeli Patent Application No. 262574, dated Jun. 24, 2020, 7 pages (with English Translation).
Examination Report in Indian Patent Application No. 201847045536, dated Sep. 22, 2020, 6 pages (with English Translation).
Response to Office Action in Russian Patent Application No. 2018143237, dated Oct. 20, 2020, 24 pages (with English Translation).
Russian Decision to Grant for Application No. 2018143237 dated Nov. 27, 2020, with English translation.

CATIONIC LIPID

TECHNICAL FIELD

The present invention relates to a novel cationic lipid.

BACKGROUND ART

Nucleic acids such as siRNA (small interfering RNA), miRNA (micro RNA) and shRNA (short hairpin RNA or small hairpin RNA) expression vectors and antisense oligonucleotides induce sequence-specific gene silencing in vivo and are known as oligonucleotide therapeutics.

Among the oligonucleotide therapeutics, siRNAs have attracted particular attention. siRNAs are double-stranded RNAs consisting of 19 to 23 base pairs and induce sequence-specific gene silencing called RNA interference (RNAi).

siRNAs are chemically stable; however, siRNAs have issues in therapeutic applications such as being liable to be decomposed by RNase (ribonuclease) in plasma and being unlikely to pass through the cell membrane alone (for example, see Patent Literature 1).

In order to address the above issues, it has been known that by encapsulating siRNA in a fine particle containing a cationic lipid, the encapsulated siRNA is protected from decomposition in blood plasma and can penetrate a lipophilic cell membrane (for example, see Patent Literature 1).

Patent Literature 2 to 6 disclose cationic lipids where are used for delivery of oligonucleotide therapeutics such as siRNAs and which have improved biodegradability.

Fine particles containing cationic lipids have such an issue of stability that the particles are likely to aggregate during storage, and a method for preventing aggregation by adding polyethylene glycol-modified lipids (PEG lipids) to the fine particles is known. Further, Patent Literature 7 discloses a method for preventing aggregation and improving a delivery efficiency of nucleic acids by configuring fine particles that comprise a specific PEG lipid, which is PEG-DPG, and a preparation that comprises the fine particles and a deionized solvent.

CITATION LIST

Patent Literature

Patent Literature 1: WO 2010/144740
Patent Literature 2: WO 2011/153493
Patent Literature 3: WO 2013/086354
Patent Literature 4: WO 2013/1158579
Patent Literature 5: WO 2015/095346
Patent Literature 6: WO 2016/104580
Patent Literature 7: WO 2014/089239

SUMMARY OF INVENTION

However, despite recent developments, there is still a need for a cationic lipid that can be used for nucleic acid delivery to the cytoplasm.

The present invention relates to [1] to [14] indicated below.

[1] A compound represented by formula (1) below or a pharmaceutically acceptable salt thereof:

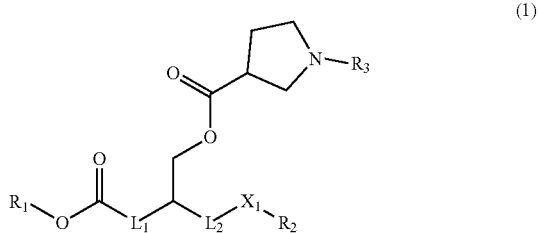

(1)

wherein $L_1$ and $L_2$ independently represent an alkylene group having 3 to 10 carbon atoms; $R_1$ and $R_2$ independently represent an alkyl group having 4 to 24 carbon atoms or an alkenyl group having 4 to 24 carbon atoms; $R_3$ represents an alkyl group having 1 to 3 carbon atoms; and $X_1$ represents a single bond or CO—O—.

[2] The compound according to [1] selected from the group consisting of compounds represented by formulae (A1) to (A9) below, or a pharmaceutically acceptable salt thereof.

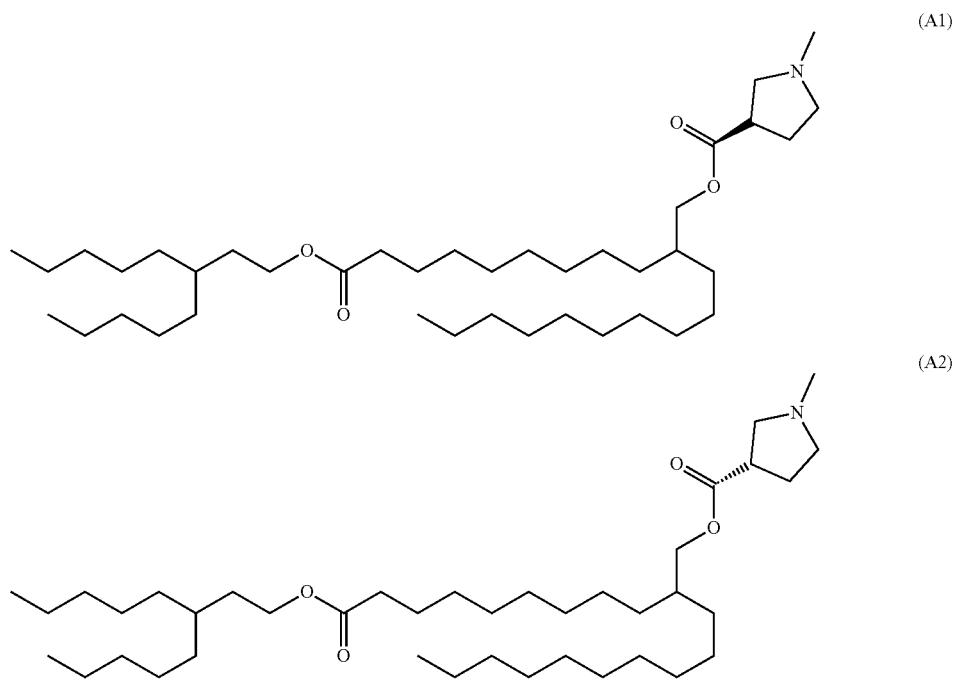

-continued
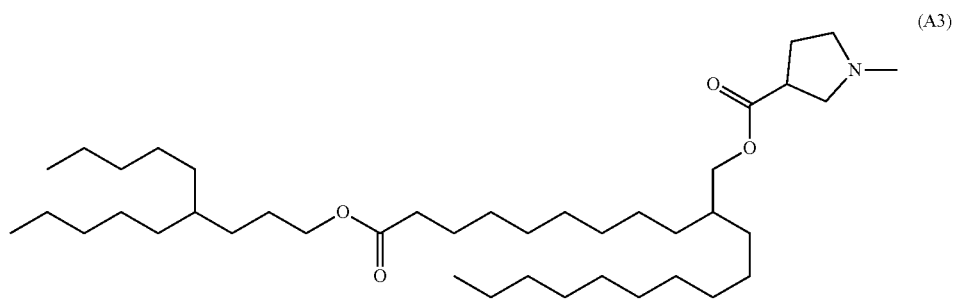
(A3)
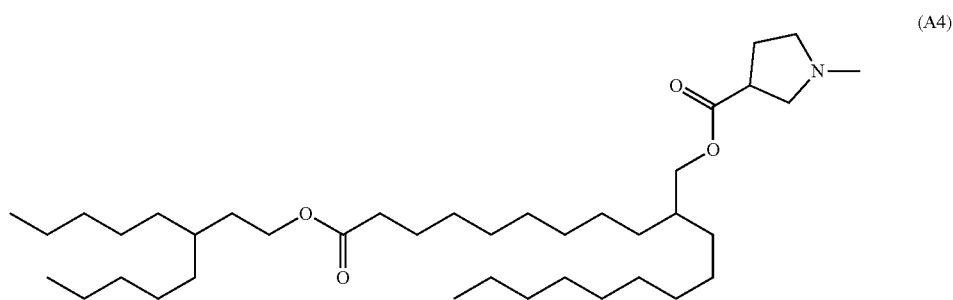
(A4)
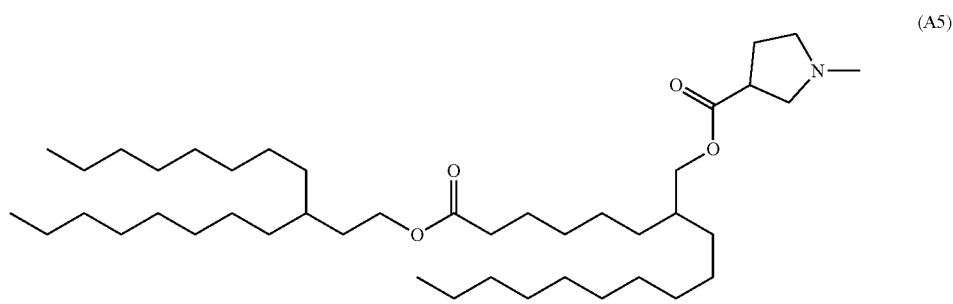
(A5)
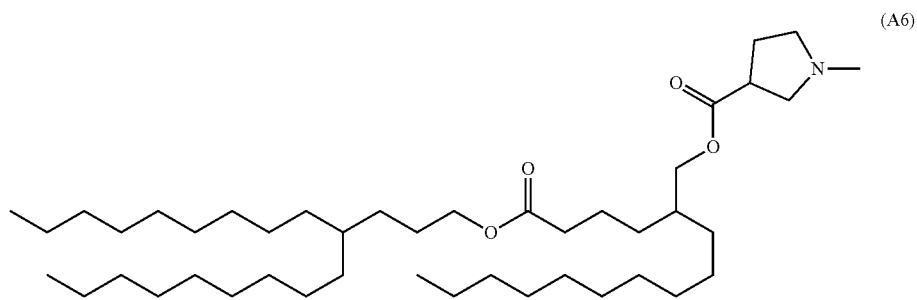
(A6)
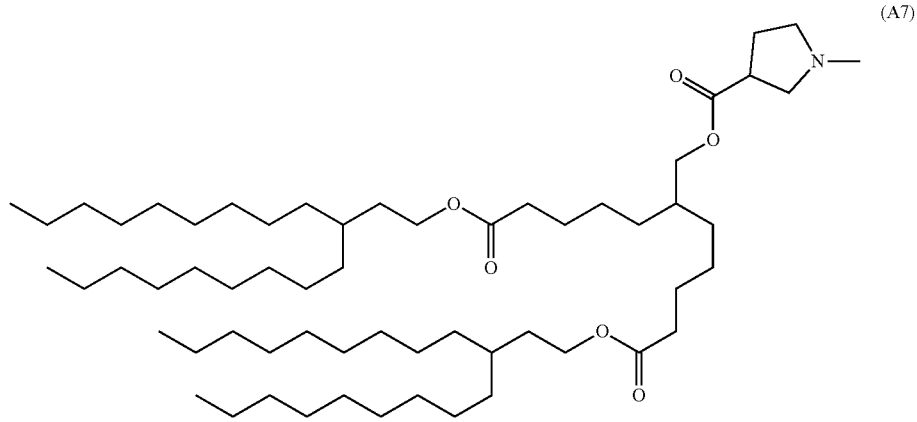
(A7)

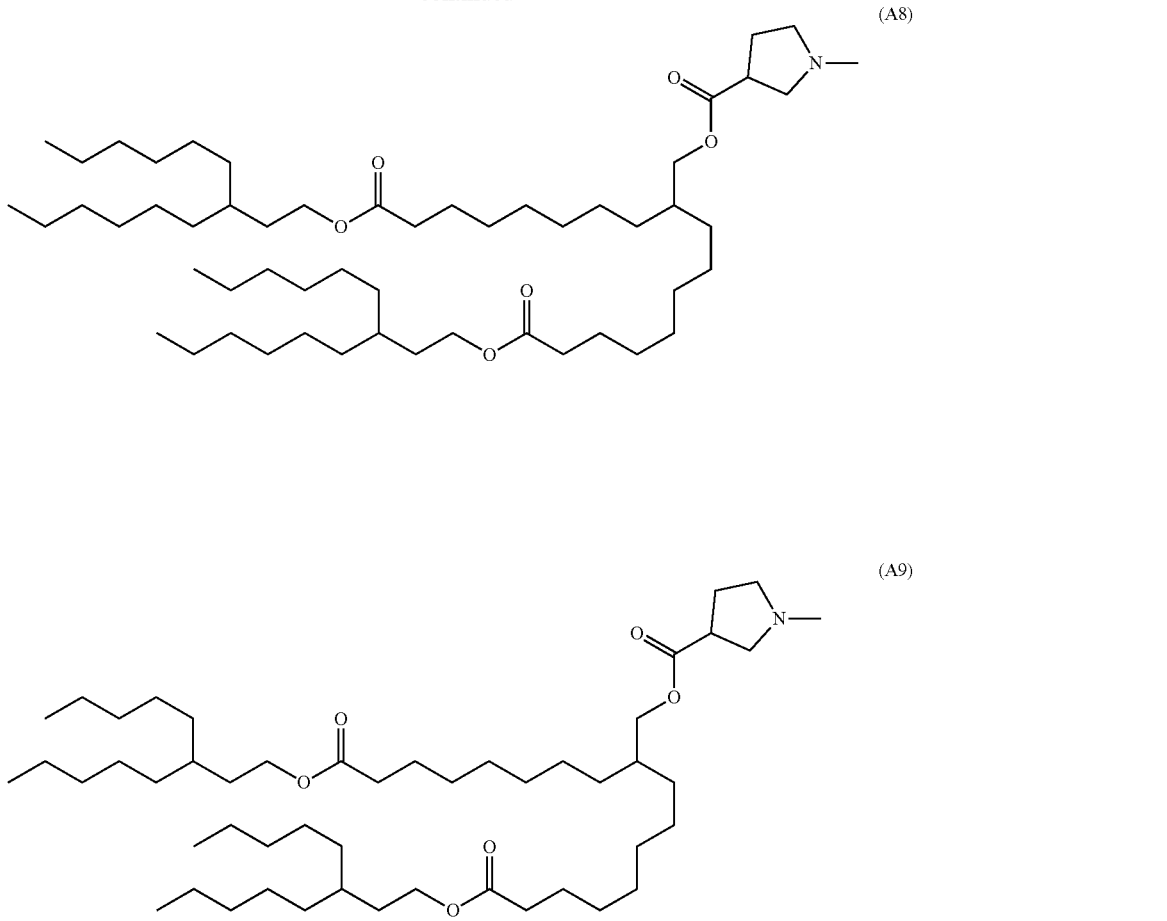

[2a] The compound according to [2] selected from the group consisting of compounds represented by formulae (A1), (A2), (A3), (A4), (A5), (A6), (A8) and (A9) above, or a pharmaceutically acceptable salt thereof.

[2b] The compound according to [2] selected from the group consisting of compounds represented by formulae (A1), (A2). (A3), (A4), (A5), (A6) and (A9) above, or a pharmaceutically acceptable salt thereof.

[2c] The compound according to [2] selected from the group consisting of compounds represented by formulae (A1), (A2), (A4) and (A6) above, or a pharmaceutically acceptable salt thereof.

[2d] The compound according to [1] represented by formula (2) or (3) below, or a pharmaceutically acceptable salt thereof:

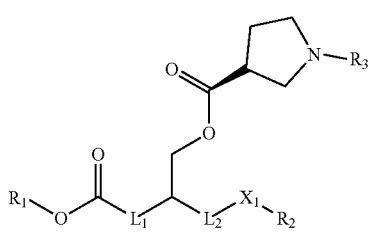

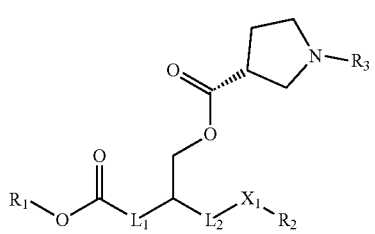

wherein $L_1$ and $L_2$, $R_1$ to $R_3$ and $X_1$ are defined as in formula (1) above.

[2e] The compound according to [1] or [2d] or a pharmaceutically acceptable salt thereof, wherein $R_3$ is a methyl group.

[3] The compound according to [1] or [2] represented by formula (A1) below, or a pharmaceutically acceptable salt thereof.

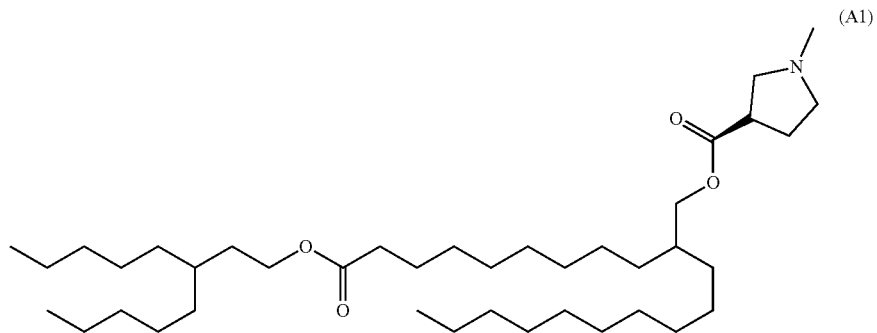
[4] The compound according to [1] or [2] represented by formula (A2) below, or a pharmaceutically acceptable salt thereof.
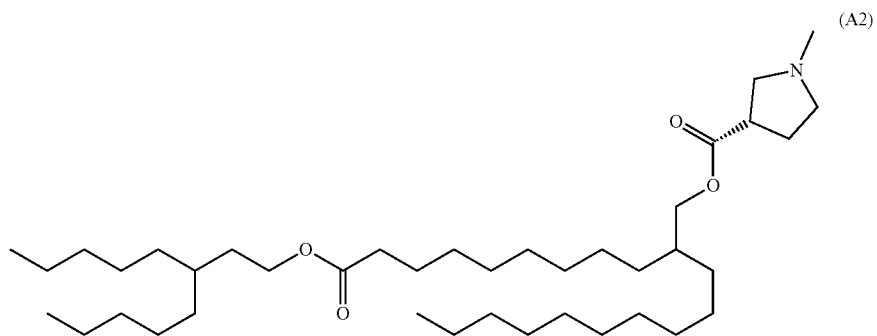
[5] The compound according to [1] or [2] represented by formula (A3) below, or a pharmaceutically acceptable salt thereof.
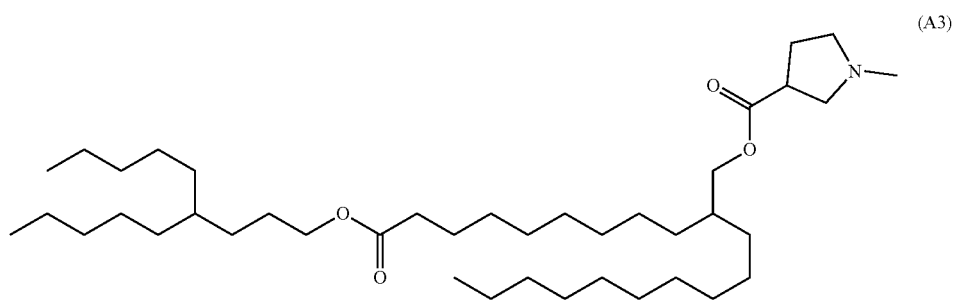 [SMILES: CCCCCCCCCCC(CCCCCCCCC(=O)OCCCC(CCCCC)CCCCC)COC(=O)C1CCN(C)C1]
[6] The compound according to [1] or [2] represented by formula (A4) below, or a pharmaceutically acceptable salt thereof.

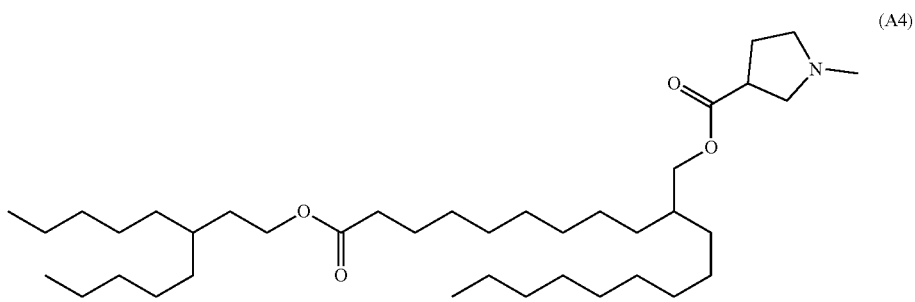 [SMILES: CCCCCCCCCC(CCCCCCCCC(=O)OCCC(CCCCC)CCCCC)COC(=O)C1CCN(C)C1]
(A4)
[7] The compound according to [1] or [2] represented by formula (A5) below, or a pharmaceutically acceptable salt thereof.
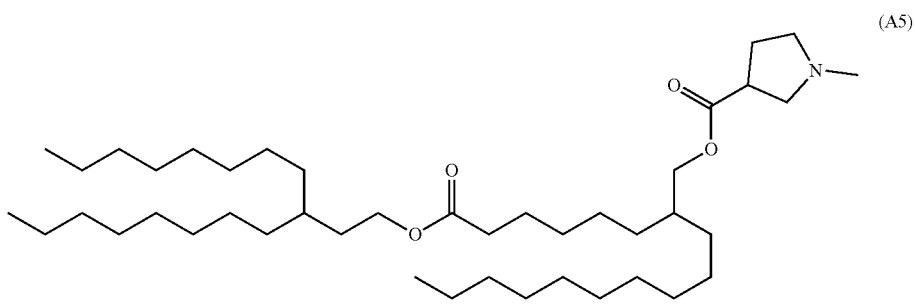 [SMILES: CCCCCCCCCCC(CCCCCC(=O)OCCC(CCCCCCCC)CCCCCCCC)COC(=O)C1CCN(C)C1]
(A5)
[8] The compound according to [1] or [2] represented by formula (A6) below, or a pharmaceutically acceptable salt thereof.
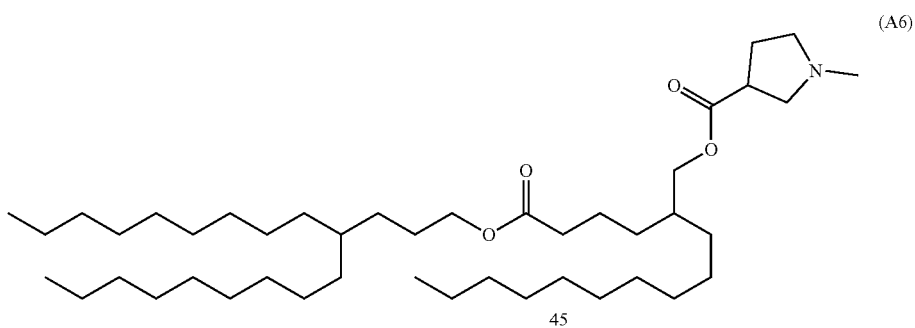
(A6)
[9] The compound according to [1] or [2] represented by formula (A7) below, or a pharmaceutically acceptable salt thereof.
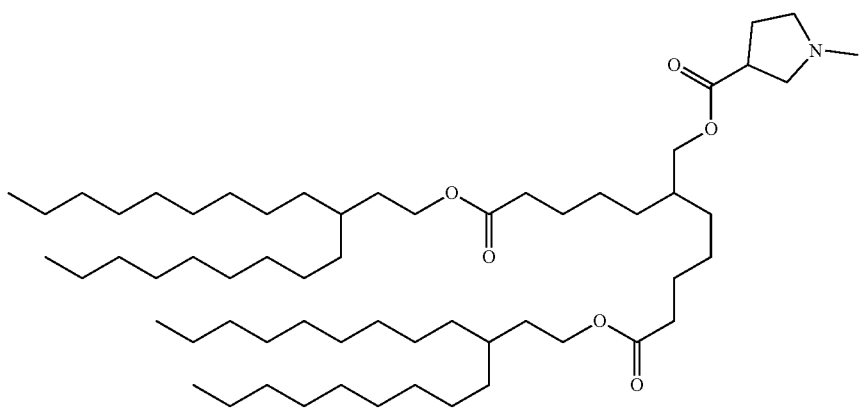 [SMILES: CCCCCCCCCC(CCCCCCCCC)CCOC(=O)CCCCC(CCCCC(=O)OCCC(CCCCCCCCC)CCCCCCCCC)COC(=O)C1CCN(C)C1]

[10] The compound according to [1] or [2] represented by formula (A8) below, or a pharmaceutically acceptable salt thereof.

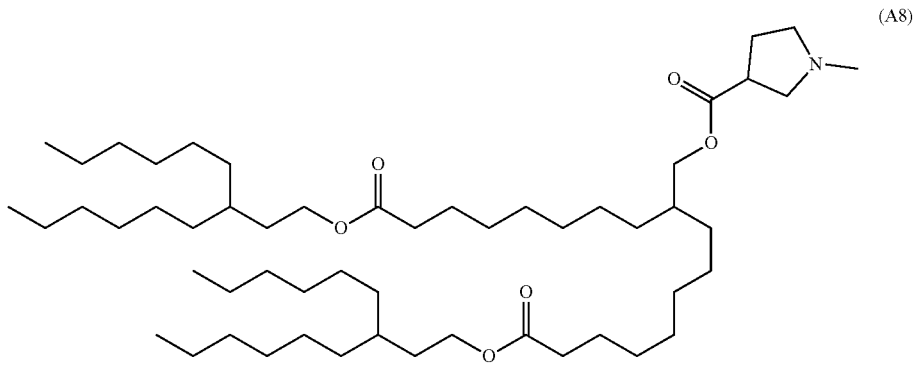 [SMILES: CCCCCCC(CCCCCC)CCOC(=O)CCCCCCCC(CCCCCCCC(=O)OCCC(CCCCCC)CCCCCC)COC(=O)C1CCN(C)C1]

[11] The compound according to [1] or [2] represented by formula (A9) below, or a pharmaceutically acceptable salt thereof.

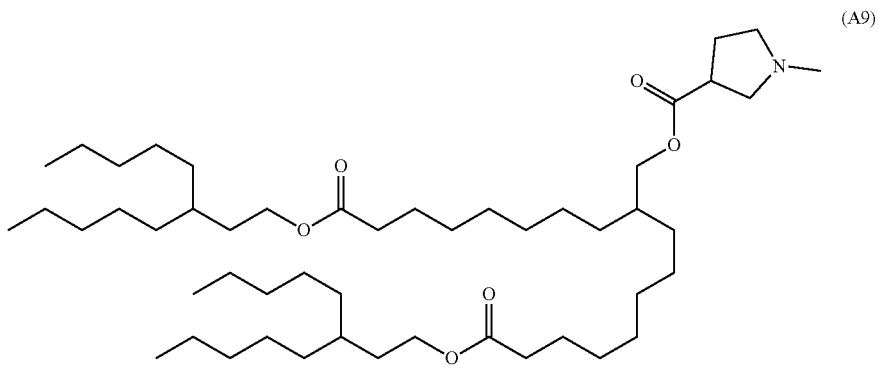 [SMILES: CCCCCC(CCCCC)CCOC(=O)CCCCCCCC(CCCCCCCC(=O)OCCC(CCCCC)CCCCC)COC(=O)C1CCN(C)C1]

[12] A lipid complex containing: (I) the compound according to any one of [1] to [11] and [2a] to [2e] or a pharmaceutically acceptable salt thereof; and (II) at least one lipid selected from the group consisting of a neutral lipid, a polyethylene glycol-modified lipid and a sterol.

[13] A composition containing: (I) the compound according to any one of [1] to [11] and [2a] to [2e] or a pharmaceutically acceptable salt thereof, (II) at least one lipid selected from the group consisting of a neutral lipid, a polyethylene glycol-modified lipid and a sterol; and (III) a nucleic acid.

[14] A method for producing a composition, the method including: the step of mixing a polar organic solvent-containing aqueous solution containing (I) the compound according to any one of [1] to [11] and [2a] to [2e] or a pharmaceutically acceptable salt thereof, and (II) at least one lipid selected from the group consisting of a neutral lipid, a polyethylene glycol-modified lipid and a sterol with an aqueous solution containing (III) a nucleic acid to obtain a mixed solution; and the step of reducing a content percentage of the polar organic solvent in the mixed solution.

Effects of Invention

The cationic lipid of the present invention has one or more effects indicated below:
(1) The cationic lipid of the present invention allows effective release of nucleic acids to the cytoplasm;
(2) The cationic lipid of the present invention can prevent an increase in the particle diameter of the lipid complex during the storage over a certain period of time.

Therefore, the cationic lipid of the present invention can be applied as a lipid used to deliver a nucleic acid into the cytoplasm.

DESCRIPTION OF EMBODIMENTS

Figure 1:
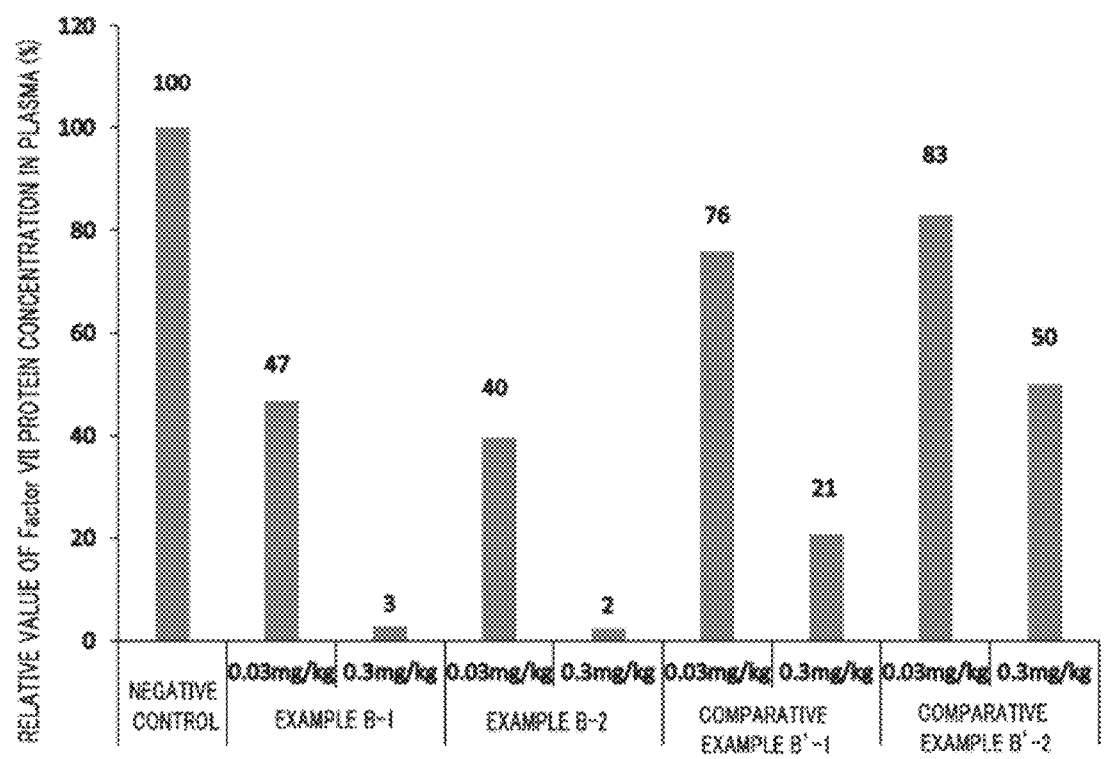
FIG. 1 is a graph illustrating the result of Test Example 1.

The present invention is hereinafter described in detail by presenting embodiments and examples. However, the present invention is not limited to the embodiments and examples described below and any modification may be made within the scope that does not deviate the concept of the present invention. All the documents and publications cited in the present specification are entirely incorporated herein by reference regardless of the purpose thereof.

<Cationic Lipid>

In one embodiment, the present invention is a compound represented by formula (1) below or a pharmaceutically acceptable salt thereof, and may be used as a cationic lipid. The cationic lipid may be a hydrate of the salt or a solvate of the salt.

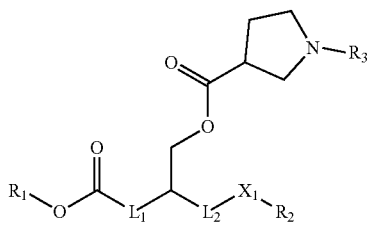

(1)

In formula (1), $L_1$ and $L_2$ independently represent an alkylene group having 3 to 10 carbon atoms; $R_1$ and $R_2$ independently represent an alkyl group having 4 to 24 carbon atoms or an alkenyl group having 4 to 24 carbon atoms; $R_3$ represents an alkyl group having 1 to 3 carbon atoms; and $X_1$ represents a single bond or CO—O—.

As used herein, "alkyl" means a linear, cyclic or branched saturated aliphatic hydrocarbon group having a denoted number of carbon atoms.

As used herein, "alkenyl" means a linear or branched hydrocarbon group having a denoted number of carbon atoms and at least one carbon-carbon double bond. Examples thereof include monoene, dienes, trienes and tetraenes; however, the term is not limited thereto.

As used herein, "alkylene" means a linear, cyclic or branched bivalent saturated aliphatic hydrocarbon group having a denoted number of carbon atoms.

As used herein, "halogen" means F, Cl, Br or I.

Asymmetric atoms (such as carbons) in the compound of the present invention may be present in the form of concentrated racemic compounds or enantiomers such as (R)-, (S)- or (R,S)-configuration.

One embodiment of the present invention is a compound represented by formula (2) or (3) below, or a pharmaceutically acceptable salt thereof.

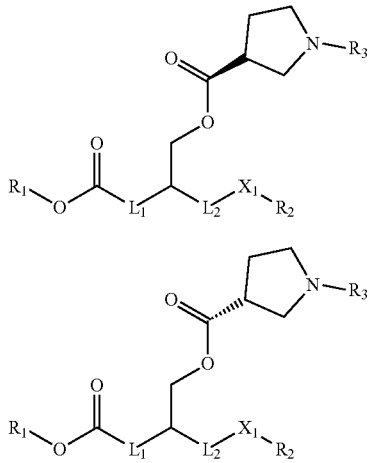

(2)

(3)

In formula (2) or (3), $L_1$ and $L_2$, $R_1$ to $R_3$ and $X_1$ are defined as above in formula (1). The compound according to the present embodiment may be used as a cationic lipid. The cationic lipid may be a hydrate of the salt or a solvate of the salt.

One embodiment of the present invention is a compound of the formulae (1) to (3) above, wherein $L_1$ and $L_2$ independently represent an alkylene group having 3 to 10 carbon atoms (for example 3 to 8 carbon atoms); $R_1$ and $R_2$ independently represent an alkyl group having 4 to 24 carbon atoms or an alkenyl group having 4 to 24 carbon atoms; $R_3$ represents an alkyl group having 1 to 3 carbon atoms; and $X_1$ represents a single bond or —CO—O—, or a pharmaceutically acceptable salt thereof, and may be used as a cationic lipid. The cationic lipid may be a hydrate of the salt or a solvate of the salt.

One embodiment of the present invention is a compound of the formulae (1) to (3) above, wherein $L_1$ and $L_2$ independently represent a linear alkylene group having 3 to 10 carbon atoms (for example 3 to 8 carbon atoms); $R_1$ and $R_2$ independently represent a linear or branched alkyl group having 4 to 24 carbon atoms or a linear alkenyl group having 4 to 24 carbon atoms; $R_3$ is an alkyl group having 1 to 3 carbon atoms; and $X_1$ is —CO—O—, or a pharmaceutically acceptable salt thereof, and may be used as a cationic lipid. The cationic lipid may be a hydrate of the salt or a solvate of the salt.

A specific embodiment of the present invention is a compound represented by formula (1a) below, or a pharmaceutically acceptable salt thereof.

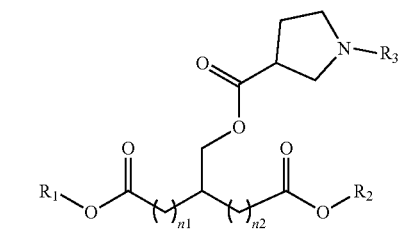

(1a)

In formula (1a), $R_1$ and $R_2$ independently is an alkyl group having 4 to 24 carbon atoms or an alkenyl group having 4 to 24 carbon atoms; $R_3$ is an alkyl group having 1 to 3 carbon atoms; and n1 and n2 independently represent an integer of 3 to 10 (for example 3 to 8).

In one embodiment of the present invention, the present invention is a compound of the formulae (1) to (3) above, wherein $X_1$ is —CO—O—; $L_1$ is the same as $L_2$; and $R_1$ is the same as $R_2$, or a pharmaceutically acceptable salt thereof, and may be used as a cationic lipid. The cationic lipid may be a hydrate of the salt or a solvate of the salt.

In one embodiment of the present invention, the present invention is a compound of the formulae (1) to (3) above, wherein $L_1$ and $L_2$ independently is a linear alkylene group having 3 to 10 carbon atoms (for example 3 to 8 carbon atoms); $R_1$ is a linear or branched alkyl group having 4 to 24 carbon atoms or a linear alkenyl group having 4 to 24 carbon atoms; $R_2$ is a linear alkyl group having 4 to 24 carbon atoms; $R_3$ is an alkyl group having 1 to 3 carbon atoms; and $X_1$ is a single bond, or a pharmaceutically acceptable salt thereof. In the present embodiment, the total number of carbon atoms in $L_2$ and $R_2$ is preferably 9 to 12. The compound of the present embodiment may be used as a cationic lipid. The cationic lipid may be a hydrate of the salt or a solvate of the salt.

A specific embodiment of the present invention is a compound represented by formula (1b) below, or a pharmaceutically acceptable salt thereof.

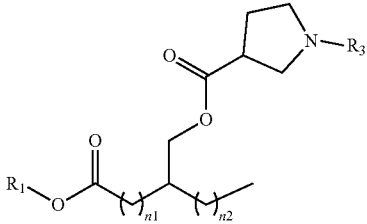

(1b)

In formula (1b), $R_1$ is an alkyl group having 4 to 24 carbon atoms or an alkenyl group having 4 to 24 carbon atoms; $R_3$ is an alkyl group having 1 to 3 carbon atoms; n1 represents an integer of 3 to 10 (for example 3 to 8); and n2 represents an integer of 6 to 33, preferably 8 to 11.
Examples of a compound according to an embodiment of the present invention are indicated below.
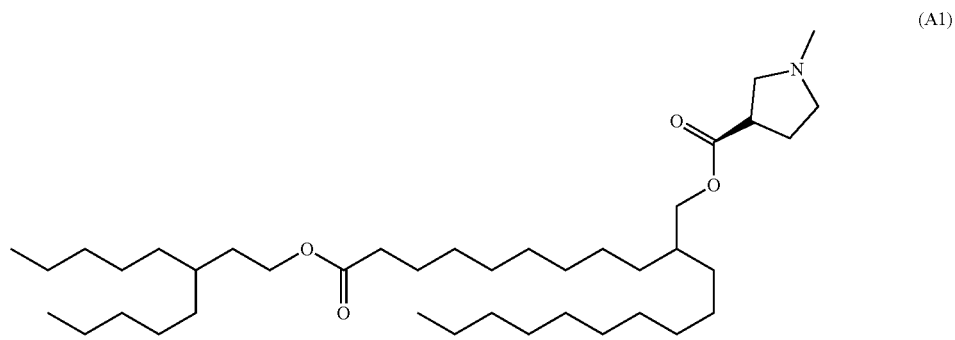
(A1)
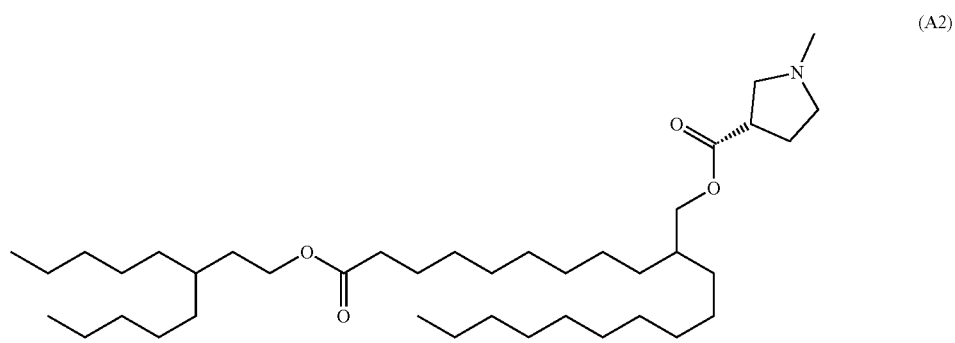
(A2)
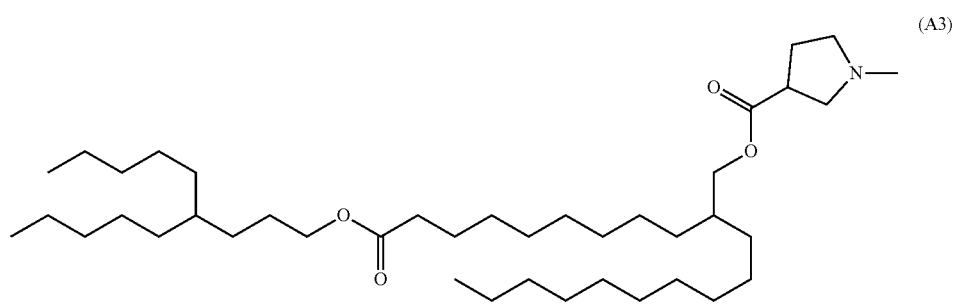
(A3)
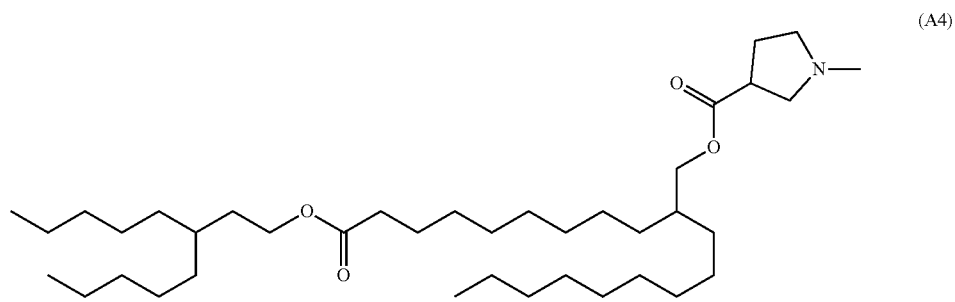
(A4)
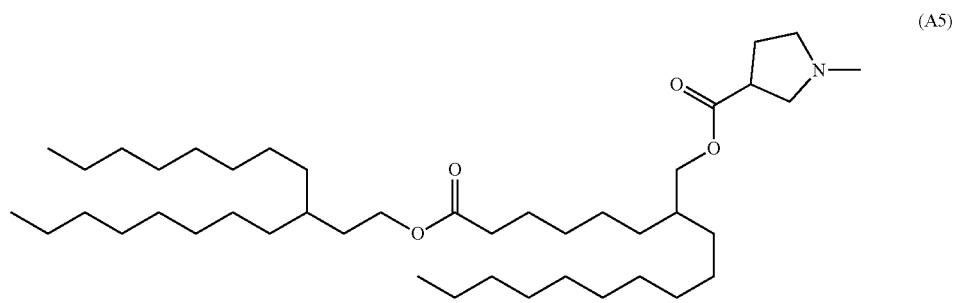
(A5)

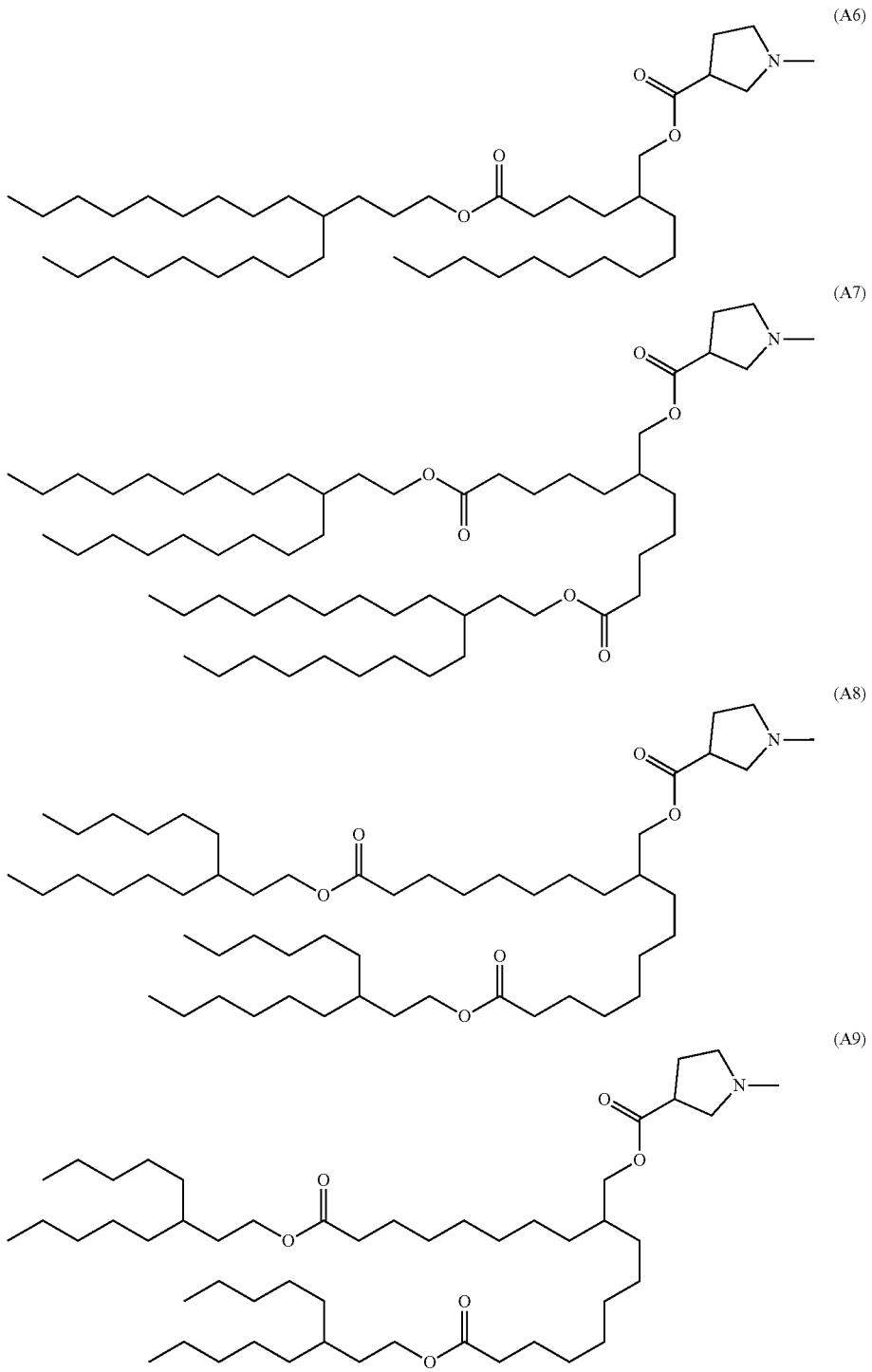

One embodiment of the present invention is a compound represented by any of formulae (A1), (A2), (A3), (A4), (A5), (A6), (A8) and (A9) above, or a pharmaceutically acceptable salt thereof, and may be used as a cationic lipid. The cationic lipid may be a hydrate of the salt or a solvate of the salt.

One embodiment of the present invention is a compound represented by any of formulae (A1), (A2), (A3), (A4), (A5), (A6) and (A9) above, or a pharmaceutically acceptable salt thereof, and may be used as a cationic lipid. The cationic lipid may be a hydrate of the salt or a solvate of the salt.

One embodiment of the present invention is a compound represented by any of formulae (A1), (A2), (A4) and (A6) above, or a pharmaceutically acceptable salt thereof, and may be used as a cationic lipid. The cationic lipid may be a hydrate of the salt or a solvate of the salt.

As used herein, "cationic lipid" is an amphiphilic molecule having a lipophilic region containing one or more hydrocarbon groups and a hydrophilic region containing a polar group that is neutral or undergoes protonation at a physiological pH. Namely, the cationic lipid of the present invention may be protonated to form a cation. For example, the compound represented by formula (1) above encompasses the compound (cationic compound) represented by formula (1)' below in which a hydrogen ion coordinates with a lone electron-pair on the nitrogen atom on the pyrrolidine ring. The cationic compound may form a salt represented by formula (1)' below and a hydrate or solvate of the salt together with an anion.

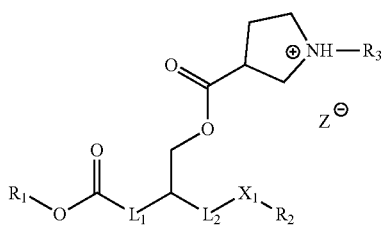

(1)'

In formula (1)', $L_1$ and $L_2$, $R_1$ to $R_3$ and $X_1$ are defined as above in formula (1). Z is an anion (counter ion). The compound of the present embodiment may be used as a cationic lipid.

The anion (Z in formula (1)' above) that may be included in the cationic lipid of the present embodiment by forming a pair with the cationic compound is not particularly limited as far as the anion is pharmaceutically acceptable. Examples thereof include inorganic ions such as a chloride ion, a bromide ion, a nitrate ion, a sulphate ion and a phosphate ion; organic acid ions such as an acetate ion, an oxalate ion, a maleate ion, a fumarate ion, a citrate ion, a benzoate ion and a methanesulphonate ion or the like.

The cationic lipid of the present invention may have a stereoisomer such as a geometric isomer and an optical isomer or a tautomer. The cationic lipid of the present invention encompasses all possible isomers including the above and mixtures thereof.

<Production Method of the Cationic Lipid>

The method for producing the cationic lipid of the present invention is now described. An embodiment of the synthetic scheme of the cationic lipid is indicated below. All the compounds described herein are encompassed by the present invention as the compounds. The compound of the present invention may be synthesized according to at least one method illustrated in the schemes indicated below. The cationic lipid of the present invention may have one or more asymmetric centres, and thus the synthesized compound may be produced as a (R)- or (S)-stereoisomer or a mixture thereof (R,S). Unless specifically indicated, it is intended that recitations of specific compounds herein encompass both individual enantiomers and racemic mixtures thereof. Methods for determination of stereochemistry and separation of stereoisomers are well known to a person skilled in the art.

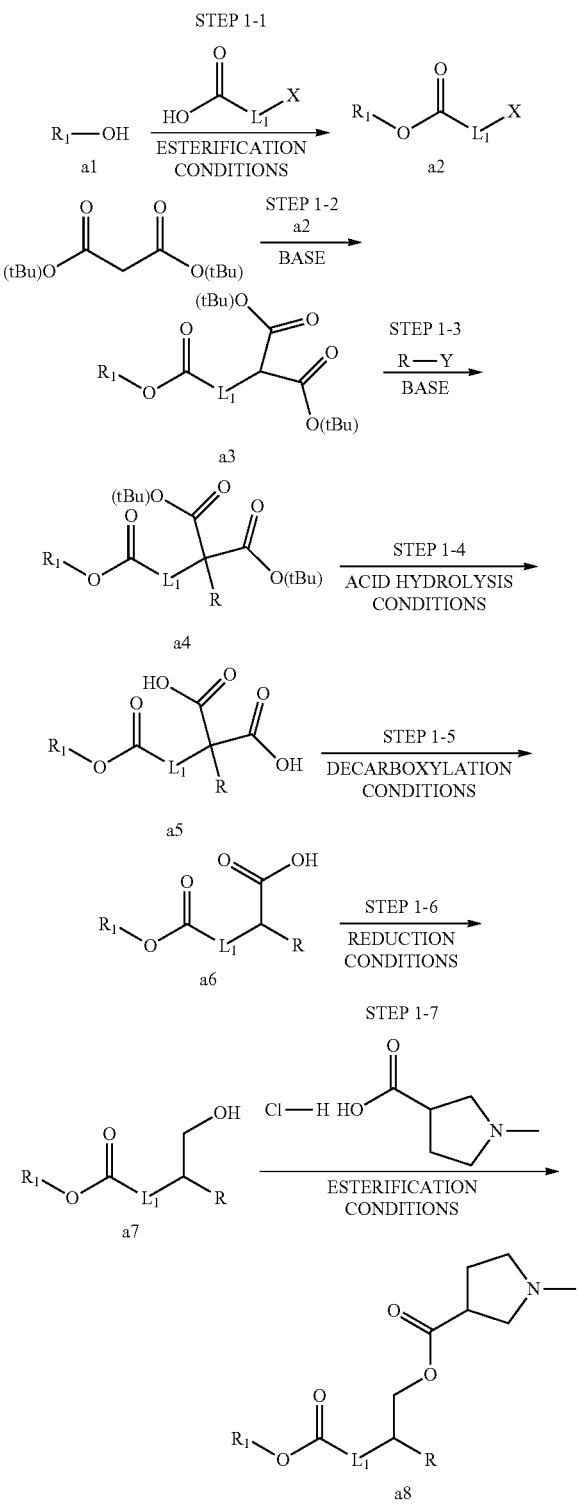

In the formulae, $L_1$ and $R_1$ respectively are defined as above in formula (1); X and Y respectively are a halogen atom; and R is -$L_2$-$X_1$—$R_2$— ($L_2$, $X_1$ and $R_2$ respectively are defined as above in formula (1)) in formula (1).

The cationic lipid of formula (1) (compound wherein $X_1$ is a single bond) may be synthesized, for example, according to scheme 1 above.

(Step 1-1: Esterification)

First, alcohol (a1) and a halogenated carboxylic acid $X-L_1-COOH$ (X is a halogen atom and $L_1$ is defined as above) (preferably a brominated carboxylic acid) are reacted in the presence of a condensation agent to obtain halogenated ester (a2). Examples of the condensation agent include 1-[3-(dimethylamino)propyl]-3-ethylcarbodiimide (EDC) hydrochloride. N,N'-dicyclohexylcarbodiimide (DCC) or the like. Optionally, a base may be added. Examples of the base include N-methylmorpholine (NMM), triethylamine (TEA), N,N-diisopropylethylamine (DIPEA), 4-(dimethylamino)pyridine (DMAP), pyridine, picoline, lutidine or the like. Examples of the solvent include tetrahydrofuran (THF), methylene chloride, chloroform, toluene, hexane, ethyl acetate or the like.

Alternatively, a halogenated carboxylic acid $X-L_1-COOH$ (X is a halogen atom and $L_1$ is defined as above) (preferably a brominated carboxylic acid) may be reacted with an electrophilic halogenating agent such as oxalyl chloride optionally in the presence of dimethylformamide to convert to a carboxylic acid chloride and the carboxylic acid chloride and an alcohol may be further reacted to obtain halogenated ester (a2). Examples of the solvent include tetrahydrofuran, methylene chloride, chloroform, toluene, hexane or the like.

(Step 1-2: Introduction of Alkyl Chain)

Next, halogenated ester (a2) and di-tert-butyl malonate are reacted in the presence of a base. By the reaction, a hydrogen atom of active methylene in the malonic diester is abstracted to introduce an alkyl ester chain, thereby obtaining compound (a3). Examples of the base include sodium hydride (NaH). Examples of the solvent include dioxane, tetrahydrofuran, cyclopentyl methyl ether, 1,2-dimethoxyethane, DMF, N-methylpyrrolidinone or the like.

(Step 1-3: Introduction of Alkyl Chain)

Next, compound (a3) and alkyl halide (R—Y) (preferably iodide) are reacted in the presence of a base to introduce an alkyl chain, thereby obtaining compound (a4). The base and the solvent similar to those in step 1-2 above may be used.

(Step 1-4: deprotection)

Next, the tert-butyl group (tBu) of compound (a4) is deprotected under acid hydrolysis conditions to obtain compound (a5). Examples of the acid used for deprotection include trifluoroacetic acid (TFA), hydrochloric acid or the like. Examples of the solvent include methylene chloride or the like.

(Step 1-5: Decarboxylation)

Next, monocarboxylic acid (a6) is obtained by decarboxylation of compound (a5). The decarboxylation reaction may be conducted by, for example, heating in a solvent. Examples of the solvent include aromatic hydrocarbons such as toluene and xylene.

(Step 1-6: Reduction)

The carboxyl group of compound (a6) is reduced to a hydroxy group in the presence of a reducing agent to obtain compound (a7). Examples of the reducing agent include borane complexes such as borane ($BH_3$)-tetrahydrofuran complex and borane-dimethyl sulphide complex. Examples of the solvent include ethers such as diethyl ether, tetrahydrofuran and dioxane; halogenated hydrocarbons such as chloroform, methylene chloride and dichloroethane:hydrocarbons such as hexane and toluene; and mixed solvents thereof.

(Step 1-7: Esterification)

The obtained alcohol (a7) and 1-methyl-pyrrolidine-3-carboxylic acid or a derivative thereof (hydrogen halide or the like) are reacted in the presence of a condensation agent and a base to obtain a final product, compound (a8) ($R=L_2-X_1-R_2$) (compound corresponding to the cationic lipid of formula (1)). The condensation agent and the base similar to those in step 1-1 may be used.

When the compound wherein $X_1$ is —CO—O— is synthesized, a compound of which carboxyl group is protected according to step 2-1 described below (halogenated ester) may be prepared in step 1-3 in scheme 1 above, the compound may be reacted with compound (a3), the obtained compound may be further subjected to step 1-4 to step 1-7 and deprotection of the carboxyl group and esterification (reaction with $R_2$—OH) may be finally conducted.

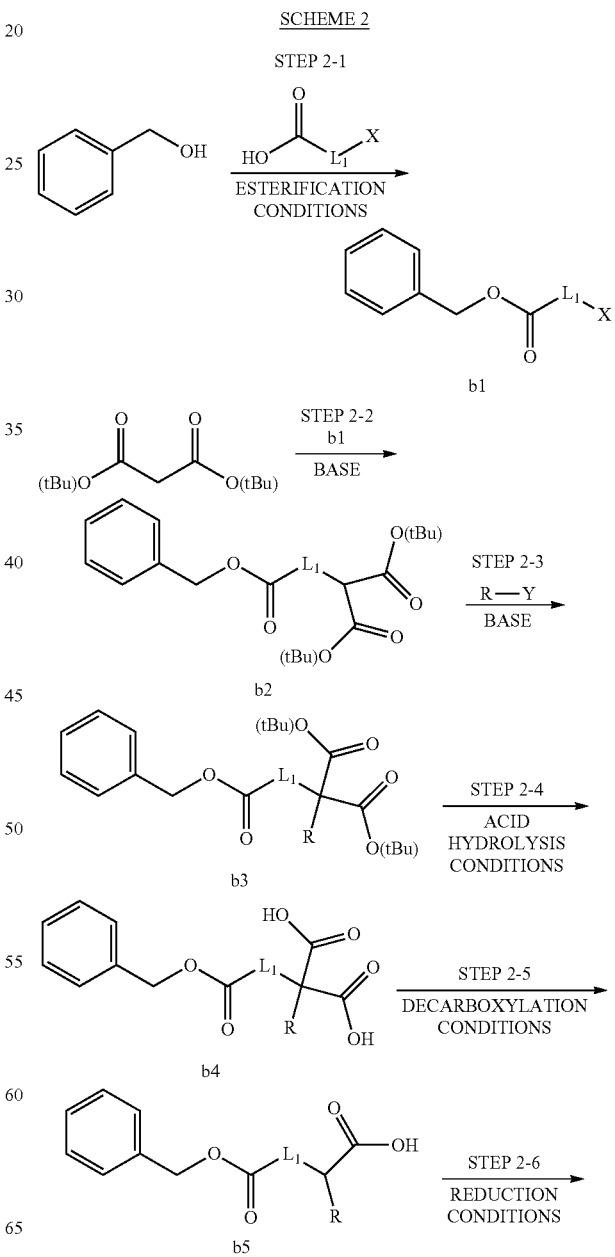

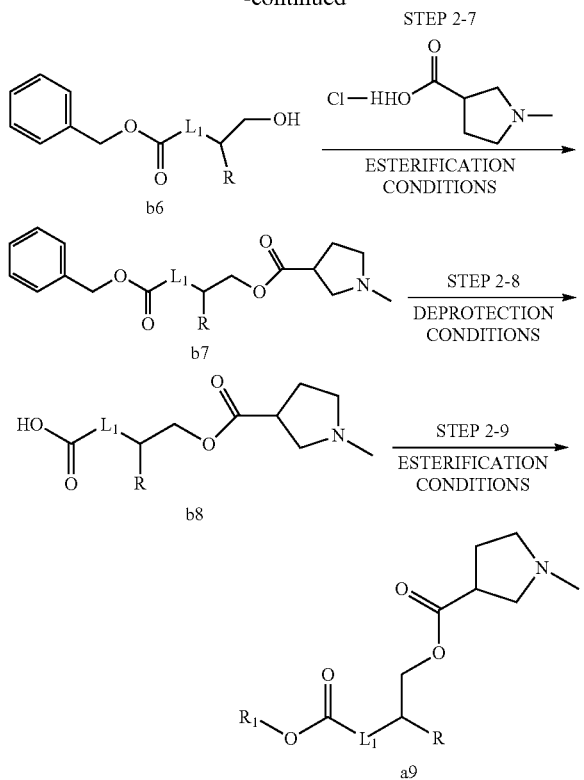

R = —$L_2$—$X_1$—$R_2$

In the formulae, $L_1$ and $R_1$ respectively are defined as above in formula (1); X and Y respectively are a halogen atom; and R is -$L_2$-$X_1$—$R_2$— ($L_2$, $X_1$ and $R_2$ respectively are defined as above in formula (1)) in formula (1).

Scheme 2 above illustrates another method for synthesizing the cationic lipid of formula (1) (compound wherein $X_1$ is a single bond) used by a person skilled in the art.

(Step 2-1: Esterification)

First, benzyl alcohol and a halogenated carboxylic acid X-$L_1$-COOH (X is a halogen atom and $L_1$ is defined as above) are subjected to esterification reaction to obtain halogenated ester (b1). Esterification conditions are similar to those in step 1-1.

(Step 2-2: Introduction of Alkyl Chain)

Next, similar to step 1-2, halogenated ester (b1) and di-tert-butyl malonate are reacted in the presence of a base to obtain compound (b2).

(Step 2-3: Introduction of Alkyl Chain)

Next, similar to step 1-3, compound (b2) and alkyl halide (R—Y) are reacted in the presence of a base to obtain compound (b3).

(Step 2-4: Deprotection)

Next, similar to step 1-4, the tert-butyl group (tBu) of compound (b3) is deprotected under acid hydrolysis conditions to obtain compound (b4).

(Step 2-5: Decarboxylation)

Next, similar to step 1-5, monocarboxylic acid (b5) is obtained.

(Step 2-6: Reduction Step)

Further, similar to step 1-6, monocarboxylic acid (b5) is reduced in the presence of a reducing agent to obtain compound (b6).

(Step 2-7: Esterification)

The obtained compound (b6) and 1-methyl-pyrrolidine-3-carboxylic acid or a derivative thereof (hydrogen halide or the like) are subjected to esterification reaction in the presence of a condensation agent and a base to obtain compound (b7). The condensation agent and the base similar to those in step 1-1 may be used.

(Step 2-8: Deprotection)

Next, under reducing conditions, the benzyl protecting group is deprotected to obtain compound (bK). Deprotection may be conducted, for example, by catalytic hydrogenation reaction in the presence of a metal catalyst such as palladium/carbon.

(Step 2-9: Esterification)

Finally, compound (b8) may be reacted with an alcohol ($R_1$—OH) in the presence of a condensation agent and a base to obtain compound (b9) (R=$L_2$-$X_1$—$R_2$) (compound corresponding to the cationic lipid of formula (1)). The condensation agent and the base similar to those in step 1-1 may be used.

In scheme 2 above, compound (b6) obtained in step 2-6 is esterified with 1-methyl-pyrrolidine-3-carboxylic acid or a derivative thereof (step 2-7), and then esterification reaction with an alcohol ($R_1$—OH) is conducted (step 2-9). However, as illustrated in scheme 2' below, the hydroxy group of compound (b6) obtained in step 2-6 may be protected, the benzyl group may be deprotected and esterification reaction with an alcohol ($R_1$—OH) may be conducted and then esterification reaction with 1-methyl-pyrrolidine-3-carboxylic acid or a derivative thereof may be conducted.

SCHEME 2'

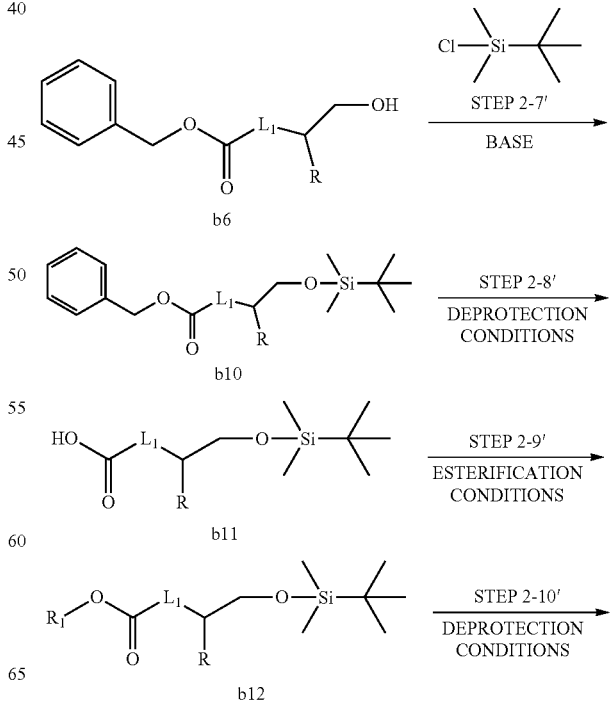

-continued

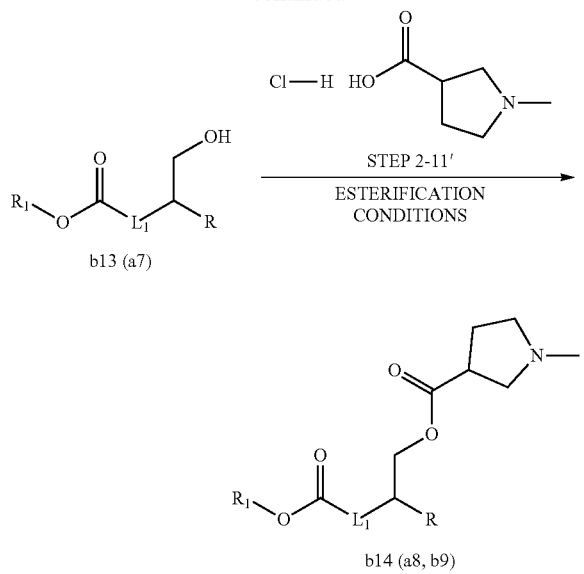

b13 (a7)

b14 (a8, b9)

R = —L₂—X₁—R₂

In the formulae, $L_1$ and $R_1$ respectively are defined as above in formula (1); and R is -$L_2$-$X_1$—$R_2$— ($L_2$, $X_1$ and $R_2$ respectively are defined as above in formula (1)) in formula (1).

(Step 2-7': Protection)

The hydroxy group of compound (b6) obtained in step 2-6 is protected. For example, ten-butyldimethylsilyl chloride (TBDMS-Cl) is reacted therewith in a solvent such as N,N-dimethylformamide in the presence of a base such as imidazole to obtain compound (b10) of which the hydroxy group is protected with a tert-butyldimethylsilyl group (TBDMS).

(Step 2-8': Deprotection)

Next, the benzyl protecting group is deprotected under reducing conditions to obtain compound (b11). Deprotection may be conducted, for example, by catalytic hydrogenation reaction in the presence of a metal catalyst such as palladium/carbon.

(Step 2-9': Esterification)

The obtained compound (b11) is reacted with an alcohol ($R_1$—OH) in the presence of a condensation agent and a base to obtain compound (b12). The condensation agent and the base similar to those in step 1-1 may be used.

(Step 2-10': Deprotection)

Next, the TBDMS group is deprotected to obtain compound (b13). Deprotection may be conducted, for example, by reaction with a fluoride salt such as tetra-n-butylammonium fluoride (TBAF) in an organic solvent such as tetrahydrofuran.

(Step 2-11': Esterification)

Finally, similar to step 1-7, the obtained alcohol (b13) and 1-methyl-pyrrolidine-3-carboxylic acid or a derivative thereof (hydrogen halide or the like) are reacted in the presence of a condensation agent and a base to obtain a final product, compound (b14) (R=$L_2$-$X_1$—$R_2$) (compound corresponding to the cationic lipid of formula (1)).

SCHEME 2''

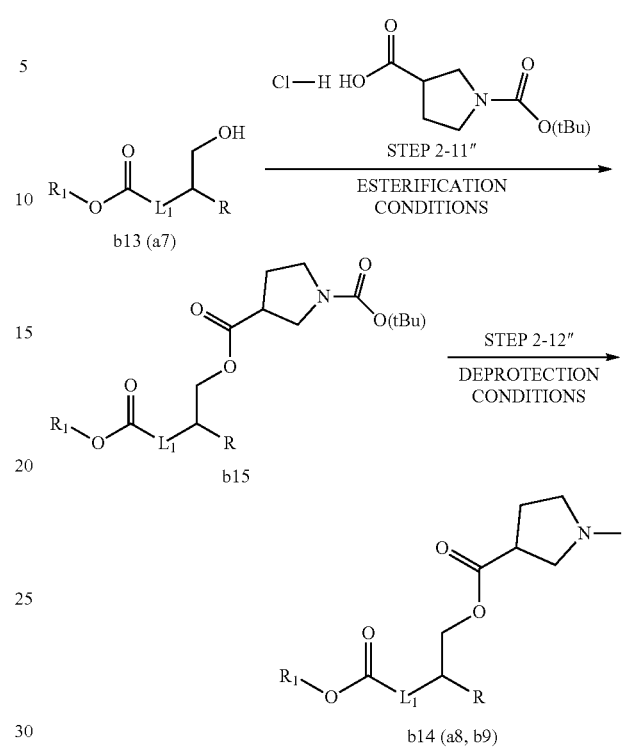

b13 (a7)

b15 b14 (a8, b9)

R = —L₂—X₁—R₂

In the formula, $L_1$ and $R_1$ respectively are defined as above in formula (1); and R is -$L_2$-$X_1$—$R_2$ ($L_2$, $X_1$ and $R_2$ respectively are defined as above in formula (1)) in formula (1).

(Step 2-11'': Esterification)

Alternatively, instead of step 2-11', a carboxylic acid or a derivative thereof in which the nitrogen atom on the pyrrolidine ring is protected with a protecting group (such as a tert-butoxycarbonyl group (tBu-O—CO—; Boc)) and an alcohol (b13) may be reacted in the presence of a condensation agent and a base similar to step 1-7 to obtain compound (b15).

(Step 2-12'': Deprotection/Reductive Amination)

Next, the tert-butoxycarbonyl group (Boc) of compound (b15) is deprotected and methylated by reductive amination. Specifically, the Boc group of compound (b15) is deprotected by reaction with a strong acid such as trifluoroacetic acid (TFA) to obtain NH, which is reacted with formaldehyde to generate imine (iminium cation), which is further reacted with a reducing agent such as NaBH(OAc)₃ or NaBH₃CN, thereby obtaining a final product, amine compound (b14) (R=$L_2$-$X_1$—$R_2$) (compound corresponding to the cationic lipid of formula (1)).

In step 2-11' or step 2-11'' above, as a carboxylic acid or a derivative thereof, a starting material in which the configuration of the carbon atom at the 3-position of the pyrrolidine ring is controlled, such as (3S)-1-methyl-pyrrolidine-3-carboxylic acid or (3R)-1-methyl-pyrrolidine-3-carboxylic acid or a derivative thereof, may be used to control the configuration of the pyrrolidine ring in the compound of formula (1).

When the compound wherein $X_1$ is —CO—O— (for example the compound of formula (1a)) is synthesized, a compound of which carboxyl group is protected according to step 2-1 above (ester compound) may be prepared in scheme 2, the compound may be reacted with compound (b2) in step 2-3, the obtained compound may be further subjected to the subsequent steps, and deprotection and esterification may be conducted in step 2-8 and step 2-9 or step 2-8' and step 2-9'. By using different types of protecting groups which can be deprotected under deprotection conditions different from each other for two carboxyl groups, a compound in which $R_1$ and $R_2$ are different may be obtained.

In the schemes above, synthesis methods in which $R_3$ in formula (1) is a methyl group are exemplarily illustrated. However, the compound wherein $R_3$ is other than methyl group may also be synthesized according to the schemes above by using 1-alkyl-pyrrolidine-3-carboxylic acid instead of 1-methyl-pyrrolidine-3-carboxylic acid in step 1-7 or step 2-7 above.

In synthesis of the compound of the present invention, unless the production of starting materials is particularly recited, the compounds are known or may be prepared according to similar methods that are well known in the art or as described in Examples below. A person skilled in the art understands that the above schemes are merely typical preparation methods of the compound of the present invention and can apply other well-known methods.

In preparation of the compound of the present invention, protection of a functional group of a molecule may be necessary and/or desirable. This may be carried out with a conventional protecting group that is well known to a person skilled in the art. The protecting group may be eliminated according to a well-known method in the art at any following appropriate stage. The protecting groups (such as a tert-butyl protecting group, a ten-butoxycarbonyl protecting group, a benzyl protecting group and a tert-butyldimethylsilyl protecting group) indicated in the above schemes may be replaced by other protecting groups that are well known to a person skilled in the art.

<Lipid Complex>

The present invention provides a lipid complex containing (I) the cationic lipid described above and (II) at least one lipid selected from the group consisting of a neutral lipid, a polyethylene glycol-modified lipid and a sterol. The lipid complex according to one embodiment of the present invention contains (I) the cationic lipid described above, (II) at least one lipid selected from the group consisting of a neutral lipid, a polyethylene glycol-modified lipid and a sterol and (III) a nucleic acid. Thus, the lipid complex of the present invention may or may not contain a nucleic acid. The lipid complex of the present embodiment allows effective release of a nucleic acid into the cytoplasm. The lipid complex of the present embodiment is prevented from an increase in the particle diameter after the storage over a certain period of time (for example 1 month, 1.5 months or 3 months) and may exhibit excellent physical stability.

Examples of the form of the complex formed from the lipid containing the cationic lipid and a nucleic acid include a complex of a nucleic acid and a membrane (reverse micelle) formed from a lipid monolayer (single molecular layer), a complex of a nucleic acid and a liposome, a complex of a nucleic acid and a micelle or the like. In the lipid complex according to one embodiment of the present invention, a nucleic acid is encapsulated in a fine particle formed with a lipid containing the cationic lipid.

The lipid complex of the present embodiment contains, based on the total lipid content of the lipid complex, the cationic lipid at, for example, 10% to 100% by mole, such as 20% to 90% by mole, such as 40% to 80% by mole. The cationic lipid used may be used alone or as a mixture of two or more.

Examples of the nucleic acid include siRNA, miRNA, shRNA expression vector, antisense oligonucleotide, mRNA, ribozyme or the like. In one embodiment, the nucleic acid may be siRNA, miRNA or mRNA.

The lipid complex of the present embodiment contains, relative to the total weight of the lipid complex, the nucleic acid at, for example, 0.01% to 50% by weight, such as 0.1% to 30% by weight, such as 1% to 10% by weight.

The lipid complex of the present embodiment contains, as lipid components, (I) the cationic lipid and (II) at least one lipid selected from the group consisting of a neutral lipid, a polyethylene glycol-modified lipid and a sterol. The lipid complex of the present embodiment contains, relative to the total weight of the lipid complex, the lipid components at, for example, 50% to 100% by weight, such as 70% to 99.99% by weight, such as 90% to 99% by weight.

"Neutral lipid" means a lipid that exists in uncharged form or in neutral amphoteric ion at a physiological pH. Examples of the neutral lipid include dioleoyl phosphatidylethanolamine (DOPE), palmitoyl oleoyl phosphatidylcholine (POPC), egg phosphatidylcholine (EPC), dimyristoyl phosphatidylcholine (DMPC), dipalmitoyl phosphatidylcholine (DPPC), distearoyl phosphatidylcholine (DSPC), diarachidoyl phosphatidylcholine (DAPC), dibehenoyl phosphatidylcholine (DBPC), dilignoceroyl phosphatidylcholine (DLPC), dioleoyl phosphatidylcholine (DOPC), sphingomyelin, ceramide, dioleoyl phosphatidylglycerol (DOPG), dipalmitoyl phosphatidylglycerol (DPPG), phosphatidylethanolamine (POPE), dioleoyl-phosphatidylethanolamine 4-(N-maleimidomethyl)-cyclohexane-1-carboxylate (DOPE-mal) or the like. The neutral lipid may be used alone or as a mixture of two or more.

The lipid complex of the present embodiment may contain, based on the total lipid content in the lipid complex, the neutral lipid at, for example, 0% to 50% by mole, such as 0% to 40% by mole, such as 0% to 30% by mole.

Examples of the polyethylene glycol-modified lipid include PEG2000-DMG (PEG2000-dimyristyl glycerol), PEG2000-DPG (PEG2000-dipalmitoyl glycerol), PEG2000-DSG (PEG2000-distearoyl glycerol), PEG5000-DMG (PEG5000-dimyristyl glycerol), PEG5000-DPG (PEG5000-dipalmitoyl glycerol), PEG5000-DSG (PEG5000-distearoyl glycerol), PEG-cDMA (N-[(methoxy-poly(ethylene glycol)2000)carbamyl]-1,2-dimyristyl oxylpropyl-3-amine), PEG-C-DOMG (R-3-[(ω-methoxy-poly(ethylene glycol)2000)carbamoyl]-1,2-dimyristyl oxylpropyl-3-amine), polyethylene glycol (PEG)-diacyl glycerol (DAG), PEG-dialkyloxypropyl (DAA), PEG-phospholipid, PEG-ceramide (Cer) or the like.

Examples of the PEG-dialkyloxypropyl include PEG-dilauryloxypropyl, PEG-dimyristyl oxypropyl, PEG-dipalmityloxypropyl, PEG-distearyloxypropyl or the like.

The polyethylene glycol-modified lipid may be used alone or as a mixture of two or more. The polyethylene glycol-modified lipid may have a terminal of PEG (polyethylene glycol) that is methoxylated (MPEG; methoxy(polyethylene glycol)).

The lipid complex of the present embodiment may contain, based on the total lipid content in the lipid complex, the polyethylene glycol-modified lipid at, for example, 0% to 30% by mole, such as 0% to 20% by mole, such as 0% to 10% by mole.

The sterol is an alcohol having a steroid back bone. Examples of the sterol include cholesterol, dihydrocholesterol, lanosterol, β-sitosterol, campesterol, stigmasterol, brassicasterol, ergocasterol, fucosterol, 3β-[N—(N',N'-dimethylaminoethyl)carbamoyl]cholesterol (DC-Chol) or the like. The sterol may be used alone or as a mixture of two or more.

The lipid complex of the present embodiment may contain, based on the total lipid content in the lipid complex, the sterol at, for example, 0% to 90% by mole, such as 10% to 80% by mole, such as 20% to 50% by mole.

The lipid components in the lipid complex of the present embodiment may be combined without any limitation, and examples of the combination include a combination of the cationic lipid, the neutral lipid and the sterol described above, a combination of the cationic lipid, the neutral lipid, the polyethylene glycol-modified lipid and the sterol described above or the like.

The "average particle diameter" of the lipid complex of the present embodiment may be calculated according to any of the volume overage, the number average and the Z-average. The lipid complex of the present embodiment may have an average particle diameter (Z-average) of, for example, 10 to 1000 nm, such as 30 to 500 nm, such as 30 to 200 nm.

The lipid complex of the present embodiment is preferably such that increase in the particle diameter of the lipid complex during storage period compared to that before the storage is minimized. For example, it is preferable that the average particle diameter (Z-average) after a storage at 4° C. for 1.5 months is 1.25 times or less, more preferably 1.2 times or less and particularly preferably 1.1 times or less of the particle diameter before the storage.

From the viewpoint of preventing nonspecific adsorption and immune reaction, the lipid complex of the present embodiment preferably has almost no surface charge in an environment of pH of about 7.4 such as in blood. In addition, from the viewpoint of improving the fusion efficiency with an endosomal membrane during incorporation into cells by endocytosis, it is preferable that the lipid complex is positively charged in an environment of low pH (for example 3.5 to 7.0).

<Composition>

The present invention provides a composition including (I) the cationic lipid described above, (II) at least one lipid selected from the group consisting of a neutral lipid, a polyethylene glycol-modified lipid and a sterol, and (III) a nucleic acid. In one embodiment of the present invention, the composition includes the lipid complex containing the nucleic acid as described above. The composition of the present embodiment allows efficient release of a nucleic acid into the cytoplasm. The composition of the present embodiment may contain the lipid complex described above, a pharmaceutically acceptable medium and optionally other additives. The pharmaceutically acceptable medium and other additives are described hereinafter.

The composition of the present invention contains, based on the total lipid content in the composition, the cationic lipid at, for example, 10% to 100% by mole, such as 20% to 90% by mole, such as 40% to 70% by mole. The cationic lipid may be used alone or as a mixture of two or more.

Examples of the nucleic acid include those described above. The composition of the present invention contains, relative to the total weight of the composition, the nucleic acid at, for example, 0.01% to 50% by weight, such as 0.1% to 30% by weight, such as 1% to 10% by weight.

The composition of the present invention contains, as lipid components, (I) the cationic lipid described above and (II) at least one lipid selected from the group consisting of a neutral lipid, a polyethylene glycol-modified lipid and a sterol.

Examples of the neutral lipid include those described above. The composition of the present invention may contain, based on the total lipid content in the composition, the neutral lipid at, for example, 0% to 50% by mole, such as 0% to 40% by mole, such as 0% to 30% by mole.

Examples of the polyethylene glycol-modified lipid includes those described above. The composition of the present invention may contain, based on the total lipid content in the composition, the polyethylene glycol-modified lipid at, for example, 0% to 30% by mole, such as 0% to 20% by mole, such as 0% to 10% by mole.

Examples of the sterol include those described above. The composition of the present invention may contain, based on the total lipid content in the composition, the sterol at, for example, 0% to 90% by mole, such as 10% to 80% by mole, such as 20% to 50% by mole.

The lipid components in the composition of the present invention may be combined without any limitation, and examples thereof include a combination of the cationic lipid, the neutral lipid and the sterol described above, a combination of the cationic lipid, the neutral lipid, the polyethylene glycol-modified lipid and the sterol described above or the like.

The composition of the present invention may contain, as other additives, saccharides such as sucrose, glucose, sorbitol and lactose; amino acids such as glutamine, glutamic acid, sodium glutamate and histidine; salts of acids such as citric acid, phosphoric acid, acetic acid, lactic acid, carbonic acid and tartaric acid or the like.

The composition of the present invention may be formulated as a pharmaceutical composition. Examples of the dosage form of the pharmaceutical composition include an injectable.

The composition of the present invention may be, for example, in a powder state obtained by removing a solvent by freeze-drying or the like or in a liquid state. The composition according to one embodiment of the present invention is a powder composition containing the lipid complex according to the embodiment described above. The powder composition may be prepared from a composition in a liquid state (dispersion) by removing a solvent by, for example, filtration or centrifugation, or prepared by freeze-drying the dispersion. When the composition is in a powder state, the composition may be suspended or dissolved in a pharmaceutically acceptable medium before using the same as an injectable. The composition according to one embodiment of the present invention is a liquid composition containing the lipid complex according to the embodiment described above and a pharmaceutically acceptable medium. When the composition is in a liquid state, the composition may be used directly or as an injectable after dissolving the composition in a pharmaceutically acceptable medium.

Examples of the pharmaceutically acceptable medium include sterile water; saline; isotonic solutions containing an adjuvant such as glucose, D-sorbitol, D-mannose. D-mannitol and sodium chloride; buffers such as phosphate buffer, citrate buffer and acetate buffer; or the like. The composition of the present embodiment may further contain additives including a dissolution adjuvant such as alcohols including ethanol, propylene glycol and polyethylene glycol, a stabilizing agent, an antioxidant, an antiseptic, a vehicle that is generally used in production of drugs, a filler, a bulking agent, a binding agent, a humectant, a disintegrating agent, a lubricant, a surfactant, a dispersant, a preservative, a flavoring agent, a soothing agent or the like.

The composition may be administered to a patient by parenteral manners such as an intra-arterial injection, an intravenous injection and a hypodermic injection. The dose of the composition may vary according to the subject to be administered, the target organ, the symptom or the mode of administration. The subject to which the composition is administered is not limited and the composition may be applied to various animals. Particularly, the composition may be administered to a mammal, preferably a human and an experimental animal in clinical tests, screening and laboratory experiments.

<Production Method of Composition>

In one embodiment, the present invention provides a method for producing a composition, the method including: the step (a) of mixing a polar organic solvent-containing aqueous solution containing (I) the cationic lipid described above, (II) at least one lipid selected from the group consisting of a neutral lipid, a polyethylene glycol-modified lipid and a sterol with an aqueous solution containing (III) a nucleic acid to obtain a mixed solution; and the step (b) of reducing a content percentage of the polar organic solvent in the mixed solution. The production method according to the present embodiment allows production of the composition that can effectively release a nucleic acid into the cytoplasm.

The lipid complex containing nucleic acids encapsulated in fine particles formed with the lipids may be formed by the electrostatic interaction between water-soluble nucleic acids and the cationic lipid and the hydrophobic interaction between lipids. For example, by reducing the content percentage of the polar organic solvent in the mixed solution, the solubility of lipid components including (I) the cationic lipid described above and (II) at least one lipid selected from the group consisting of a neutral lipid, a polyethylene glycol-modified lipid and a sterol in the polar organic solvent-containing aqueous solution may be changed, thereby forming the lipid complex. Examples of the polar organic solvent include alcohols such as ethanol.

First, in the step (a), a polar organic solvent-containing aqueous solution containing (I) the cationic lipid and (II) at least one lipid selected from the group consisting of a neutral lipid, a polyethylene glycol-modified lipid and a sterol dissolved therein and an aqueous solution containing (III) a nucleic acid are mixed to obtain a mixed solution. The concentration of the polar organic solvent in the polar organic solvent-containing aqueous solution is not particularly limited as long as lipid molecules can be solubilized even after being mixed with the aqueous solution of the nucleic acid. For example, the concentration of the polar organic solvent in the polar organic solvent-containing aqueous solution in the step (a) may be 0% to 60% by weight.

Next, in the step (b), water or the like is added to the mixed solution to reduce the content percentage of the polar organic solvent. As a result, the lipid complex may be formed. In order to form the lipid complex effectively, it is preferable that the content percentage of the polar organic solvent is rapidly reduced. For example, the concentration of the polar organic solvent in the final polar organic solvent-containing aqueous solution in the step (b) may be 0% to 5% by weight.

Alternatively, the mixed solution obtained in the step (a) may be subjected to dialysis to remove the polar organic solvent and replace the solvent by a pharmaceutically acceptable medium. Because the content percentage of the polar organic solvent in the solution decreases during the dialysis process, the lipid complex may be formed as a result.

According to the method for producing the composition of the present embodiment, the lipid complex containing a nucleic acid efficiently encapsulated in fine particles can be obtained. The lipid complex may have excellent physical stability. For example, after the storage over a certain period of time (for example 1 month or 3 months), an increase in the particle diameter may be minimized.

When the nucleic acid encapsulated in the composition is an oligonucleotide therapeutic, the composition may be used as a pharmaceutical composition. For example, the composition of the present invention may be used in the therapy (such as gene therapy) for introducing a desired nucleic acid to the target cytoplasm (such as cytoplasm causing a disease) in vivo or in vitro. Thus, the present invention according to one embodiment provides a method (particularly a gene therapy method) of therapy of various diseases by using the pharmaceutical composition containing the lipid complex. The subject to be administered, the method and condition of administration are the same as above.

One embodiment of the present invention may be a kit for delivering a nucleic acid therapeutic, the kit containing the cationic lipid. The kit may also be preferably used in the therapy (such as gene therapy) of various target cells. In the kit of the present embodiment, the state of storage of the cationic lipid is not particularly limited, and may be any state such as solution or powder by taking the stability (storage property), convenience of use or the like into account. The kit of the present embodiment may contain, in addition to the cationic lipid, for example various nucleic acids, various media (pharmaceutically acceptable media, buffers), an instruction (instruction manual) or the like. The kit of the present embodiment is used for preparing a composition or a lipid complex containing a desired nucleic acid to be introduced into target cells and lipids containing the above cationic lipid. The prepared composition or lipid complex may be effectively used for delivery of the nucleic acid to target cells. Further, one embodiment of the present invention may be a kit for delivering a nucleic acid therapeutic, the kit containing a pharmaceutical composition that contains the cationic lipid. The kit of the present embodiment may contain, in addition to the pharmaceutical composition, for example various media (pharmaceutically acceptable media), an instruction (instruction manual) or the like.

EXAMPLES

The present invention is more specifically described hereinafter by way of Examples, Production Examples and Test Examples. However, the present invention is not limited to these Examples. In Examples and Production Examples, the nomenclature of the compounds is obtained on the software (product name "ChemDraw Plugin ver. 15.1", produced by PerkinElmer Co., Ltd.).

All starting materials, reagents, acids, bases, dehydrating agents, solvents and catalysts that are used for synthesis of the compounds of the present invention are commercially available or may be produced according to the organic synthesis methods that are well known to a person skilled in the art. Further, the compounds of the present invention may be, as demonstrated in Examples below, produced according to the organic synthesis methods that are well known to a person skilled in the art.

The abbreviations used in Examples are conventional and well known to a person skilled in the art. Some of the abbreviations are indicated below.

DIPEA: N,N-Diisopropylethylamine
DMAP: 4-(Dimethylamino)pyridine
DMSO: Dimethyl sulfoxide
DMF: N,N-Dimethylformamide
EDC.HCl: 1-Ethyl-3-(3-dimethylaminopropyl)carbodiimide hydrochloride
n-: Normal
tert-: Tertiary
TFA: Trifluoroacetic acid
THF: Tetrahydrofuran
LAH: Lithium aluminium hydride
TBAF: Tetra-n-butylammonium fluoride
$^1$H-NMR: Proton nuclear magnetic resonance spectrometry In Examples and Production Examples below, "room temperature" indicates generally from about 10° C. to about 35° C. % indicates percent by weight unless otherwise stated.

The chemical shifts of proton nuclear magnetic resonance spectrometry are recorded in δ unit (ppm) from tetramethylsilane. The abbreviations in the patterns are as indicated below:

s: singlet, d: doublet, t: triplet, q: quartet, quin: quintet, m: multiplet, br: broad.

For chromatography. Parallel Prep produced by YAMAZEN Corporation {column: produced by YAMAZEN Corporation, Hi-Flash Column (Silica gel), size; S (16×60 mm), M (20×75 mm), L (26×100 mm), 2 L (26×150 mm)}, or flash automatic purification system Isolera produced by Biotage {column: SNAP Cartridge KP-Sil (10 g, 25 g, 50 g, 100 g, 340 g)} was used.

A. Synthesis of Cationic Lipid

Production Example 1

Synthesis of benzyl 9-bromononanoate

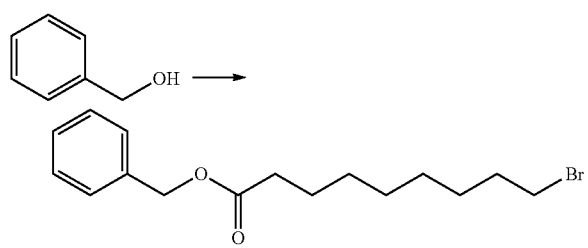

Benzyl alcohol (1.3 mL, 12.6 mmol), 9-bromononanoic acid (3.0 g, 12.65 mmol) and DMAP (155 mg, 1.27 mmol) were dissolved in methylene chloride (25 mL), to which EDC.HCl (2.67 g, 13.92 mmol) was added under ice cooling, and the mixture was stirred at room temperature for 2 hours. The reaction mixture was added with a saturated sodium hydrogen carbonate aqueous solution and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (3.7 g, 11.31 mmol).

$^1$H-NMR (400 MHz, CDCl$_3$) δ(ppm): 1.22-1.48 (m, 8H), 1.58-1.71 (m, 2H), 1.78-1.90 (m, 2H), 2.30-2.40 (m, 2H), 3.35-3.44 (m, 2H), 5.12 (s, 2H), 7.26-7.45 (m, 5H).

Production Example 2

Synthesis of 4-pentylnonan-1-ol

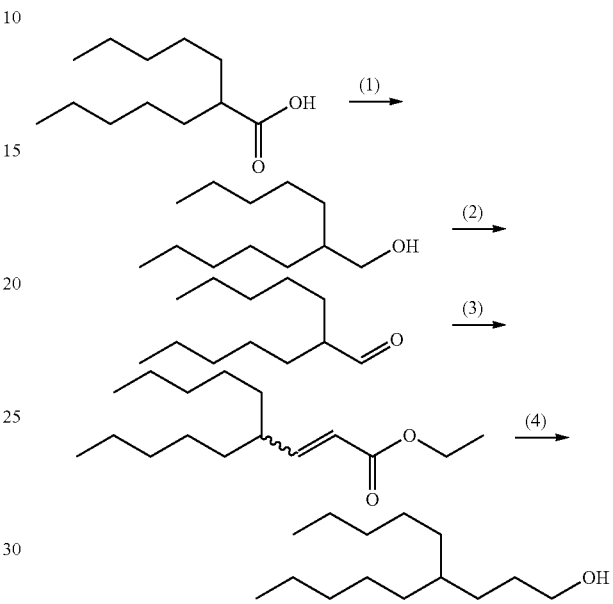

(1) Synthesis of 2-pentylheptan-1-ol

2-Pentylheptanoic acid (2.0 g, 9.98 mmol) was dissolved in THF (50 mL), to which borane-THF complex (1.0 M, 25.0 mL, 25.0 mmol) was added dropwise at −78° C. The mixture was allowed to warm to room temperature and stirred overnight. The mixture was again cooled to −78° C. borane-THF complex (1.0 M, 10.0 mL, 10.0 mmol) was further added and the mixture was stirred overnight at room temperature. A saturated ammonium chloride aqueous solution was added and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (cyclohexane/ethyl acetate) to obtain the titled compound (1.40 g, 7.49 mmol).

$^1$H-NMR (600 MHz, CDCl$_3$) δ(ppm): 0.89 (t, J=7.2 Hz, 6H), 1.24-1.35 (m, 19H), 1.45-1.47 (m, 1H), 1.62-1.71 (m, 1H), 3.54 (br d, J=0.5 Hz, 2H).

(2) Synthesis of 2-pentylheptanal

To a solution of oxalyl chloride (1.3 mL, 15.0 mmol) in methylene chloride (1.0 mL), a solution of DMSO (2.1 mL, 30.0 mmol) in methylene chloride (1.0 mL) was added dropwise at −78° C. After stirring for 30 minutes, a solution of the compound (1.40 g, 7.49 mmol) obtained in Production Example 2-(1) in methylene chloride (2.0 mL) was added. After stirring for 1 hour, triethylamine (5.2 mL, 37.5 mmol) was added. After heating to room temperature, the mixture was stirred for 2 hours and water was added to separate an organic phase. The organic phase was washed with water and a saturated sodium chloride solution, and the solvent was removed by distillation under reduced pressure. The residue was purified by silica gel column chromatography (cyclohexane/diethyl ether) to obtain the titled compound (1.26 g, 6.82 mmol).

$^1$H-NMR (600M Hz, CDCl3) δ(ppm): 0.89 (t, J=0.8 Hz, 7H), 1.19-1.34 (m, 13H), 1.40-1.47 (m, 4H), 1.57 (s, 1H), 1.58-1.66 (m, 2H), 2.15-2.28 (m, 1H), 2.66 (s, 1H), 9.56 (d, J=3.3 Hz, 1H).

(3) Synthesis of ethyl 4-pentylnonan-2-enoate

To a solution of ethoxycarbonylmethyl(triphenyl)phosphonium bromide (2.23 g, 5.19 mmol) in THF (14 mL), a sodium hexamethyldisilazane-THF solution (I M, 5.2 mL, 5.19 mmol) was added dropwise at −78° C. After heating to 0° C. over 2 hours, a solution of the compound (0.48 g, 2.59 mmol) obtained in Production Example 2-(2) in THF (4.0 mL) was added dropwise through a cannula. After stirring overnight at room temperature, the mixture was refluxed under heating for 4 hours. Water was added and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (cyclohexane/diethyl ether) to obtain the titled compound (0.28 g, 1.0) mmol).

$^1$H-NMR (600 MHz, CDCl$_3$) δ(ppm): 0.89 (br t, J=7.2 Hz, 5H), 0.87 (br t, J=7.0 Hz, 6H), 1.18-1.35 (m, 26H), 1.38-1.46 (m, 3H), 1.53-1.64 (m, 4H), 2.09-2.24 (m, 1H), 2.38 (t, J=7.5 Hz, 3H), 4.19 (q, J=7.0 Hz, 2H), 5.76 (d, J=15.8H, 1H), 6.74 (dd, J=15.6, 9.4 Hz, 1H).

(4) Synthesis of 4-pentylnonan-1-ol

To a solution of the compound (0.28 g, 1.10 mmol) obtained in Production Example 2-(3) in THF (2.2 mL), a LAH-THF solution (1M, 2.2 mL, 2.2 mmol) was added dropwise under a nitrogen atmosphere at 0° C. The mixture was heated to room temperature and refluxed under heating for 18 hours. At 0° C., the mixture was diluted with tert-butyl methyl ether (4.6 mL) and then sequentially added with water (0.078 mL), a sodium hydroxide aqueous solution (15%, 0.078 mL) and water (0.234 mL). The reaction mixture was stirred for 15 minutes, filtered through Celite and washed with diethyl ether. The filtrate was concentrated, and the residue was purified by silica gel column chromatography (cyclohexane/diethyl ether) to obtain the titled compound (0.048 g, 0.22 mmol).

$^1$H-NMR (600 MHz, CDCl$_3$) δ(ppm): 0.89 (t, J=7.2 Hz, 6H), 1.19-1.33 (m, 21H), 1.43 (s, 1H), 1.47 (br s, 1H), 1.50-1.58 (m, 2H), 3.62 (t, J=6.8 Hz, 2H).

Production Example 3

Synthesis of 3-pentyloctyl 9-bromononanoate

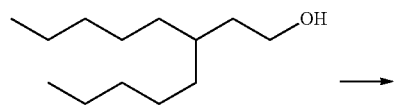

-continued

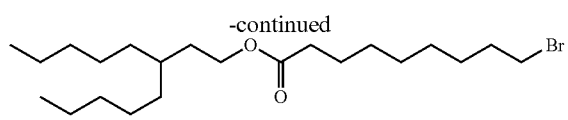

To a solution of 9-bromononanoic acid (1.61 g, 6.77 mmol) in methylene chloride (35 mL), oxalyl chloride (0.95 mL, 10.8 mmol) was added under ice cooling and then DMF (0.050 mL, 0.68 mmol) was added over 40 minutes. After stirring at room temperature for 40 minutes, the mixture was concentrated under reduced pressure and azeotroped with toluene. The residue was dissolved in methylene chloride (35 mL), 3-pentyloctan-1-ol (1.36 g, 6.77 mmol) was added and the mixture was stirred at room temperature for 1 hour. The reaction mixture was added with a saturated sodium hydrogen carbonate aqueous solution and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (cyclohexane/diethyl ether) to obtain the titled compound (2.22 g, 5.28 mmol).

$^1$H-NMR (600 MHz, CDCl$_3$) δ(ppm): 0.89 (t, J=7.3 Hz, 6H), 1.22-1.35 (m, 22H), 1.37-1.47 (m, 3H), 1.53-1.66 (m, 5H), 1.86 (quin, J=7.2 Hz, 2H), 2.29 (t, J=7.5 Hz, 2H), 3.41 (t, J=7.0 Hz, 2H), 4.09 (t, J=7.2 Hz, 2H).

Production Example 4

Synthesis of 3-octylundecan-1-ol

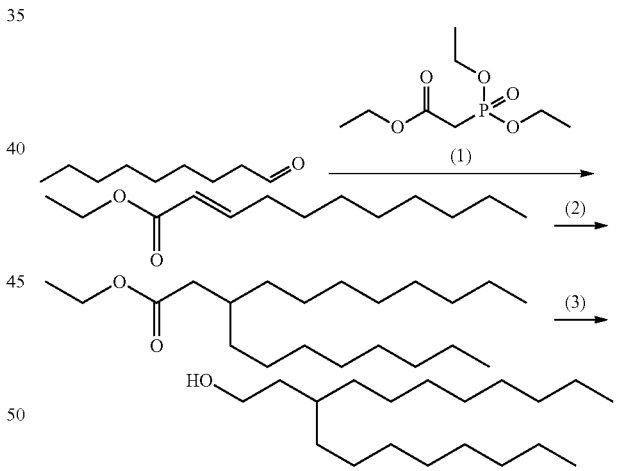

(1) Synthesis of (E)-ethyl 2-undecenoate

To a suspension of ethyl 2-(diethoxyphosphoryl)acetate (5.0 mL, 25.3 mmol) in THF (40 mL), 60% sodium hydride (0.93 g, 23.2 mmol) was gradually added under ice cooling. After 30 minutes, a solution of nonyl aldehyde (3.6 mL, 21.1 mmol) in THF (40 mL) was added dropwise and stirred for 30 minutes. After stirring at room temperature for 2 hours, the mixture was extracted with ethyl acetate. The organic phase was dried over anhydrous magnesium sulphate, and following filtration, the solvent was removed by distillation under reduced pressure. To a suspension of ethyl 2-(diethoxyphosphoryl)acetate (2.5 mL, 12.7 mmol) in THF (20 mL), 60% sodium hydride (1.0 g, 25.0 mmol) was gradually added under ice cooling and then the solution of the crude product obtained as above in THF (20 mL) was added dropwise. After stirring for 1 hour, water was added and extracted with ethyl acetate. The organic phase was dried over anhydrous magnesium sulphate, and following filtration, the solvent was removed by distillation under reduced pressure. The residue was purified by silica gel column chromatography (cyclohexane/diethyl ether) to obtain the titled compound (3.07 g, 14.6 mmol).

$^1$H-NMR (600 MHz, CDCl$_3$) δ(ppm): 1.22-1.35 (m, 14H), 1.41-1.50 (m, 2H), 2.15-2.23 (m, 2H), 4.14-4.22 (m, 2H), 5.81 (dt, J=15.6, 1.5 Hz, 1H), 6.96 (dt, J=15.6, 7.0 Hz, 1H).

(2) Synthesis of Ethyl 3-octylundecanoate

Copper(I) bromide (0.21 g, 1.45 mmol) and lithium chloride (0.12 g, 2.89 mmol) were suspended in THF (40 mL) and stirred at room temperature for 10 minutes. Under ice cooling, the compound (3.07 g, 14.46 mmol) obtained in Production Example 4-(1) and chlorotrimethylsilane (2.2 mL, 17.4 mmol) were sequentially added and stirred for 20 minutes. An octylmagnesium bromide-THF solution (2.0 M, 8.7 mL, 17.4 mmol) was added dropwise and stirred for additional 1.5 hours. A saturated ammonium chloride aqueous solution was added and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (cyclohexane/diethyl ether) to obtain the titled compound (4.43 g, 13.58 mmol).

$^1$H-NMR (600 MHz, CDCl$_3$) δ(ppm): 0.88 (t, J=7.1 Hz, 6H), 1.19-1.33 (m, 34H), 1.35-1.35 (m, 1H), 1.84 (br d, J=5.0 Hz, 1H), 2.21 (d, J=7.0 Hz, 2H), 4.12 (q, J=7.2 Hz, 2H).

(3) Synthesis of 3-octylundecan-1-ol

To a solution of the compound (4.43 g, 13.56 mmol) obtained in Production Example 4-(2) in THF (30 mL), a LAH-THF solution (2 M, 13.6 mL, 27.1 mmol) was added dropwise at room temperature in a nitrogen atmosphere. After heating at 65° C. for 5 hours, water (1 mL), a sodium hydroxide aqueous solution (2 M, 1 mL) and water (2 mL) were serially added under ice cooling. The reaction mixture was stirred for 10 minutes, filtered through Celite and washed with diethyl ether. The filtrate was concentrated under reduced pressure and the residue was purified by silica gel column chromatography (cyclohexane/diethyl ether) to obtain the titled compound (4.43 g. quant).

$^1$H-NMR (600 MHz, CDCl$_3$) δ(ppm): 0.88 (t, J=7.1 Hz, 6H), 1.12 (br s, 1H), 1.19-1.33 (m, 30H), 1.39-1.44 (m, 2H), 1.49-1.54 (m, 2H), 3.62-3.71 (m, 2H).

Production Example 5

Synthesis of 3-octylundecyl 6-bromohexanoate

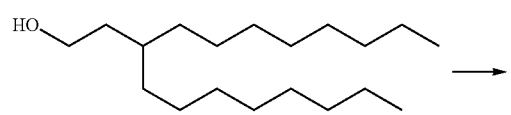

The compound (3.46 g, 12.16 mmol) obtained in Production Example 4, 6-bromohexanoic acid (2.61 g, 13.38 mmol) and DMAP (0.15 g, 1.22 mmol) were dissolved in methylene chloride (22 mL), to which EDC.HCl (2.91 g, 15.20 mmol) was added under ice cooling, and the mixture was stirred for 3 days at room temperature. The reaction mixture was concentrated under reduced pressure and diluted with diethyl ether. The reaction mixture was washed with a saturated sodium hydrogen carbonate aqueous solution, water and a 10% citric acid aqueous solution and dried over anhydrous magnesium sulphate. Following filtration, the solvent was removed by distillation under reduced pressure. The residue was purified by silica gel column chromatography (n-heptane/ethyl acetate) to obtain the titled compound (4.67 g, 10.09 mmol).

$^1$H-NMR (600 MHz, CDCl$_3$) δ (ppm): 0.88 (t, J=7.0 Hz, 6H), 1.21-1.32 (m, 30H), 1.39 (br s, 1H), 1.44-1.51 (m, 2H), 1.57 (q, J=7.0 Hz, 2H), 1.66 (quin, J=7.6 Hz, 2H), 1.84-1.91 (m, 2H), 2.31 (t, J=7.4 Hz, 2H), 3.40 (t, J=6.7 Hz, 2H), 4.09 (t, J=7.2 Hz, 2H).

Production Example 6

Synthesis of benzyl 4-bromobutanoate

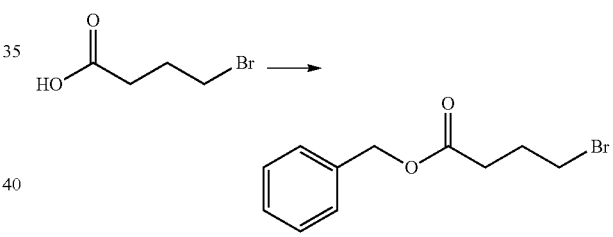

To a solution of 4-bromobutanoic acid (2.94 g, 17.61 mmol) in methylene chloride (88 mL), oxalyl chloride (1.6 mL, 18.5 mmol) and DMF (0.40 mL, 1.8 mmol) were serially added at room temperature. After stirring at room temperature for 30 minutes, benzyl alcohol (1.90 g, 17.61 mmol) was added and stirred for 15 minutes. The reaction mixture was concentrated under reduced pressure and the residue was purified by silica gel column chromatography (cyclohexane/diethyl ether) to obtain the titled compound (3.64 g, 14.09 mmol).

$^1$H-NMR (600 MHz, CDCl$_3$) δ(ppm): 1.61 (s, 1H), 2.21 (quin, J=6.8 Hz, 2H), 2.57 (t, J=7.3 Hz, 2H), 3.47 (t, J=6.4 Hz, 2H), 5.15 (s, 2H), 7.33-7.40 (m, 5H).

Production Example 7

Synthesis of 4-nonyltridecan-1-ol

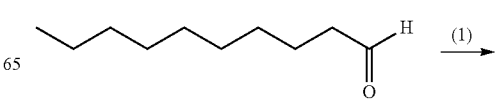

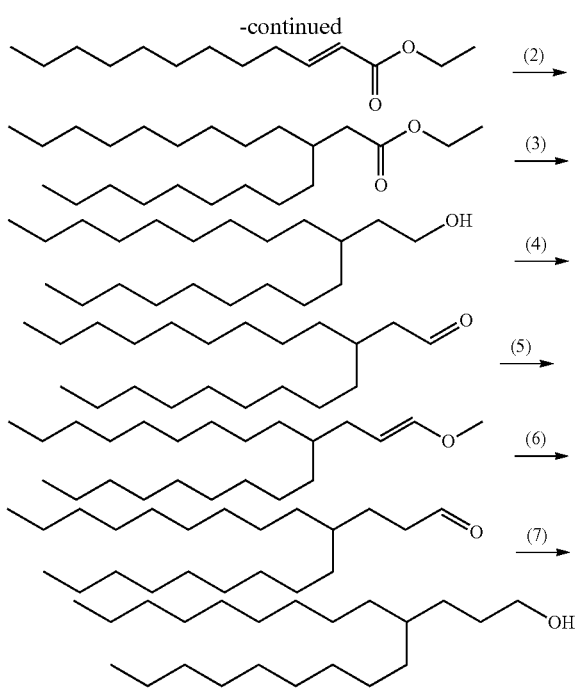

(1) Synthesis of (E)-ethyl 2-dodecenoate

To a suspension of 60% sodium hydride (1.28 g, 32.0 mmol) in 1,2-dimethoxyethane (70 mL), ethyl 2-(diethoxyphosphoryl)acetate (6.4 mL, 32.0 mmol) was added dropwise under ice cooling. After 20 minutes, a solution of decyl aldehyde (5.0 mL, 32.0 mmol) in 1,2-dimethoxyethane (30 mL) was added and the mixture was stirred overnight at room temperature. A saturated ammonium chloride aqueous solution was added and extracted with ethyl acetate. The organic phase was dried over anhydrous magnesium sulphate and following filtration, the solvent was removed by distillation under reduced pressure. The organic phase was dried over anhydrous magnesium sulphate and following filtration, the solvent was removed by distillation under reduced pressure. The residue was purified by silica gel column chromatography (n-pentane/diethyl ether) to obtain the titled compound (5.18 g, 23.0 mmol).

$^1$H-NMR (600 MHz, CDCl$_3$) δ(ppm): 0.88 (t, J=7.06 Hz, 4H), 1.25-1.32 (m, 18H), 1.45 (dt, J=14.5, 7.3 Hz, 2H), 2.15-2.22 (m, 2H), 4.15-4.26 (m, 2H), 5.72-5.90 (m, 1H), 6.96 (dt, J=15.6.7.0 Hz, 1H).

(2) Synthesis of ethyl 3-nonyldodecanoate

According to the method in Production Example 4-(2), the titled compound (2.76 g, 7.84 mmol) was obtained from the compound (2.22 g, 9.80 mmol) obtained in Production Example 7-(1), copper(I) bromide (0.141 g, 0.98 mmol), lithium chloride (0.083 g, 1.96 mmol), chlorotrimethylsilane (1.4 mL, 10.8 mmol), a nonylmagnesium bromide-THF solution (1.0 M, 10.8 mL, 10.8 mmol) and THF (53 mL).

$^1$H-NMR (600 MHz, CDCl$_3$) δ(ppm): 0.77 (t, J=7.0 Hz, 9H), 1.04 (br d, J=7.3 Hz, 1H), 1.11-1.26 (m, 48H), 1.29-1.39 (m, 1H), 1.44 (s, 1H), 1.68-1.84 (m, 1H), 2.05-2.09 (m, 1H), 2.09-2.16 (m, 2H), 3.46 (t, J=6.8 Hz, 1H), 3.42-3.49 (m, 1H), 4.01 (q, J=7.0 Hz, 2H), 4.07 (q, J=7.3 Hz, 1H), 5.7 (dt, J=15.7, 1.5 Hz, 1H), 6.85 (dt, J=15.8, 7.0 Hz, 1H), 7.15 (s, 1H).

(3) Synthesis of 3-nonyldodecan-1-ol

According to the method in Production Example 4-(3), the titled compound (1.34 g, 4.29 mmol) was obtained from the compound (2.76 g, 7.80 mmol) obtained in Production Example 7-(2), a LAH-THF solution (1M, 10.1 mL, 10.1 mmol) and THF (15 mL).

$^1$H-NMR (600 MHz, CDCl$_3$) δ(ppm): 0.89 (t, J=7.0 Hz, 6H), 1.18 (br s, 2H), 1.23-1.33 (m, 33H), 1.43 (br d, J=9.9 Hz, 1H), 1.53 (q, J=6.8 Hz, 2H), 1.59 (br s, 1H), 3.67 (t, J=7.2 Hz, 2H).

(4) Synthesis of 3-nonyldodecanal

According to the method in Production Example 2-(2), the titled compound (0.30 g, quant) was obtained from the compound (0.30 g, 0.97 mmol) obtained in Production Example 7-(3), oxalyl chloride (0.17 mL, 1.94 mmol). DMSO (0.27 mL, 3.88 mmol) and triethylamine (0.68 mL, 4.85 mmol).

$^1$H-NMR (600 MHz, CDCl$_3$) δ (ppm): 0.89 (t, J=7.0 Hz, 6H), 1.15-1.38 (m, 1H), 1.44 (s, 9H), 1.55 (s, 1H), 1.95 (br s, 1H), 2.33 (dd, J=6.6, 2.6 Hz, 2H), 9.77 (t, J=2.4 Hz, 1H).

(5) Synthesis of 10-(3-methoxyallyl)nonadecane

To a solution of (methoxymethyl)triphenylphosphonium chloride (1.10 g, 3.21 mmol) in THF (5.0 mL), a sodium hexamethyldisilazane THF solution (1M, 3.2 mL, 3.2 mmol) was added dropwise at −78° C. After 15 minutes, the mixture was added to a solution of the compound (0.50 g, 1.60 mmol) obtained in Production Example 7-(4) in THF (2.0 mL) under ice cooling through a cannula. After stirring for 1.5 hours, water was added and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (cyclohexane/diethyl ether) to obtain the titled compound (0.33 g, 0.98 mmol).

$^1$H-NMR (600 MHz, CDCl$_3$) δ(ppm): 0.89 (t, J=7.0 Hz, 6H), 1.20-1.35 (m, 28H), 1.41-1.48 (m, 1H), 1.55 (s, 1H), 1.88 (t, J=6.4 Hz, 1H), 1.96-2.11 (m 1H), 3.52 (s, 1H), 3.57 (s, 1H), 4.32 (q, J=7.3 Hz, 1H), 4.69 (dt, J=12.7, 7.4 Hz, 1H), 5.91 (d, J=6.2 Hz, 1H), 6.25 (d, J=12.8H, 1H).

(6) Synthesis of 4-nonyltridecanal

The compound (0.33 g, 0.97 mmol) obtained in Production Example 7-(5) was dissolved in THF (2.0 mL) and 1N hydrochloric acid (2.95 mL, 2.95 mmol) was added at room temperature and heated at 70° C. After 36 hours, water was added and extracted with diethyl ether. The organic phase was washed with a saturated sodium chloride solution and dried over anhydrous magnesium sulphate. Following filtration, the solvent was removed by distillation under reduced pressure to obtain the titled compound (0.28 g, 0.87 mmol).

$^1$H-NMR (600 MHz, CDCl$_3$) δ(ppm): 0.89 (t, J=7.0 Hz, 7H), 1.20-1.34 (m, 39H), 1.44 (s, 1H), 1.54-1.62 (m, 3H), 2.37-2.43 (m, 2H), 9.78 (t, J=1.8 Hz, 1H).

(7) Synthesis of 4-nonyltridecan-1-ol

The compound (0.28 g, 0.88 mmol) obtained in Production Example 7-(6) was dissolved in ethanol (13 mL), to which sodium borohydride (0.13 g, 3.50 mmol) was added at 0° C. After 1.5 hours, a saturated ammonium chloride aqueous solution was added and extracted with methylene chloride. The organic phase was washed with a saturated sodium chloride solution and dried over anhydrous magnesium sulphate. Following filtration, the solvent was removed by distillation under reduced pressure. The organic phase was dried over anhydrous magnesium sulphate and following filtration, the solvent was removed by distillation under reduced pressure to obtain the titled compound (0.28 g, 0.86 mmol).

$^1$H-NMR (600 MHz, CDCl$_3$) δ(ppm): 0.89 (t, J=7.0 Hz, 6H), 1.20-1.33 (m, 37H), 1.44 (s, 1H), 1.49-1.65 (m, 3H), 3.63 (t, J=6.8H, 2H).

Production Example 8

Synthesis of benzyl 5-bromopentanoate

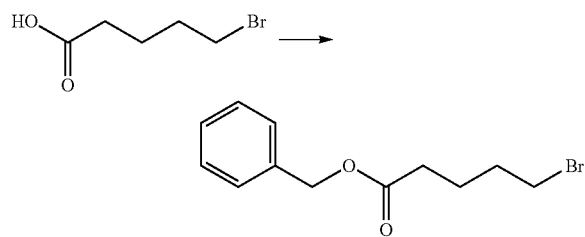

According to the method in Production Example 6, the titled compound (5.39 g, 19.89 mmol) was obtained from 5-bromopentanoic acid (4.0 g, 22.1 mmol), benzyl alcohol (2.3 mL, 22.1 mmol), methylene chloride (110 mL), oxalyl chloride (2.0 mL, 23.2 mmol) and DMF (0.17 mL, 2.21 mmol).

$^1$H-NMR (600 MHz, CDCl$_3$) δ(ppm): 1.62 (s, 1H), 1.79-1.85 (m, 2H), 1.88-1.93 (m, 2H), 2.41 (t, J=7.3 Hz, 2H), 3.41 (t, J=6.6 Hz, 2H), 5.14 (s, 2H), 7.33-7.40 (m, 5H).

Production Example 9

Synthesis of 3-hexylnonan-1-ol

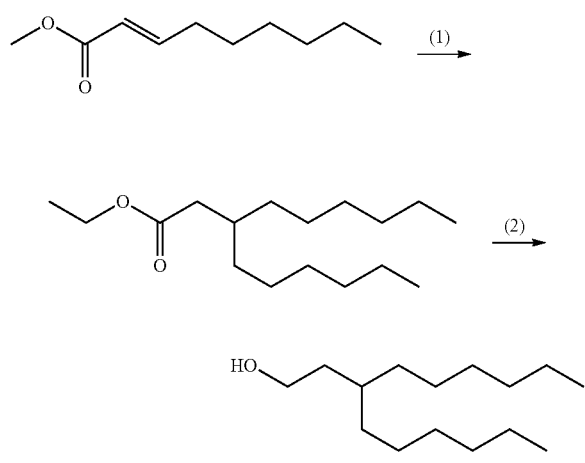

(1) Synthesis of methyl 3-hexylnonanoate

According to the method in Production Example 4-(2), the titled compound (4.18 g, 16.27 mmol) was obtained from methyl (E)-2-nonenoate (3.6 mL, 18.92 mmol), copper(I) bromide (0.275 g, 1.92 mmol), lithium chloride (0.160 g, 3.76 mmol), chlorotrimethylsilane (2.7 mL, 21.27 mmol), a hexylmagnesium bromide-THF solution (2.0 M, 10.5 mL, 21.0 mmol) and THF (50 mL).

$^1$H-NMR (600 MHz, CDCl$_3$) δ(ppm): 0.86-0.91 (m, 7H), 1.12-1.37 (m, 25H), 1.79-1.87 (m, 1H), 2.23 (d, J=6.8 Hz, 2H), 3.66 (s, 3H).

(2) Synthesis of 3-hexylnonan-1-ol

According to the method in Production Example 4-(3), the titled compound (2.33 g, 10.14 mmol) was obtained from the compound (4.0 g, 15.6 mmol) obtained in Production Example 9-(1), a LAH-THF solution (2.4 M, 13.0 mL, 31.2 mmol) and THF (60 mL).

$^1$H-NMR (600 MHz, CDCl$_3$) δ(ppm): 0.88 (t, J=7.0 Hz, 6H), 1.13 (br s, 1H), 1.19-1.34 (m, 20H), 1.41 (br s, 1H), 1.49-1.57 (m, 4H), 3.66 (br d, J=5.5 Hz, 2H).

Production Example 10

Synthesis of Benzyl 8-bromooctanoate

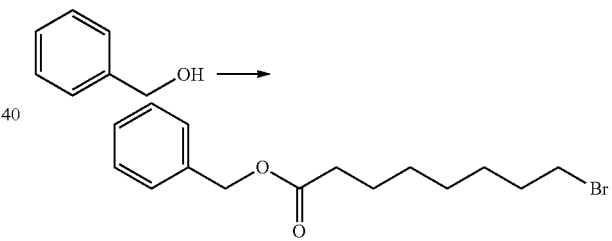

According to the method in Production Example 1, benzyl alcohol (1.3 mL, 12.5 mmol), 8-bromooctanoic acid (3.06 g, 12.73 mmol) and DMAP (0.15 g, 1.25 mmol) were dissolved in methylene chloride (60 mL), to which EDC.HCl (2.99 g, 15.61 mmol) was added under ice cooling, and the mixture was stirred at room temperature for 2 hours. The reaction mixture was added with a saturated sodium hydrogen carbonate aqueous solution and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (3.91 g, 12.5 mmol).

$^1$H-NMR (600 MHz, CDCl$_3$) δ(ppm): 1.22-1.48 (m, 6H), 1.58-1.71 (m, 2H), 1.78-1.90 (m, 2H), 2.30-2.38 (m, 2H), 3.33-3.45 (m, 2H), 5.12 (s, 2H), 7.28-7.44 (m, 5H).

Synthesis of Cationic Lipid (1)
Example A-1
Synthesis of (3S)-2-{9-oxo-9-[(3-pentyloctyl)oxy]nonyl}dodecyl 1-methylpyrrolidine-3-carboxylate (Cationic Lipid 1)
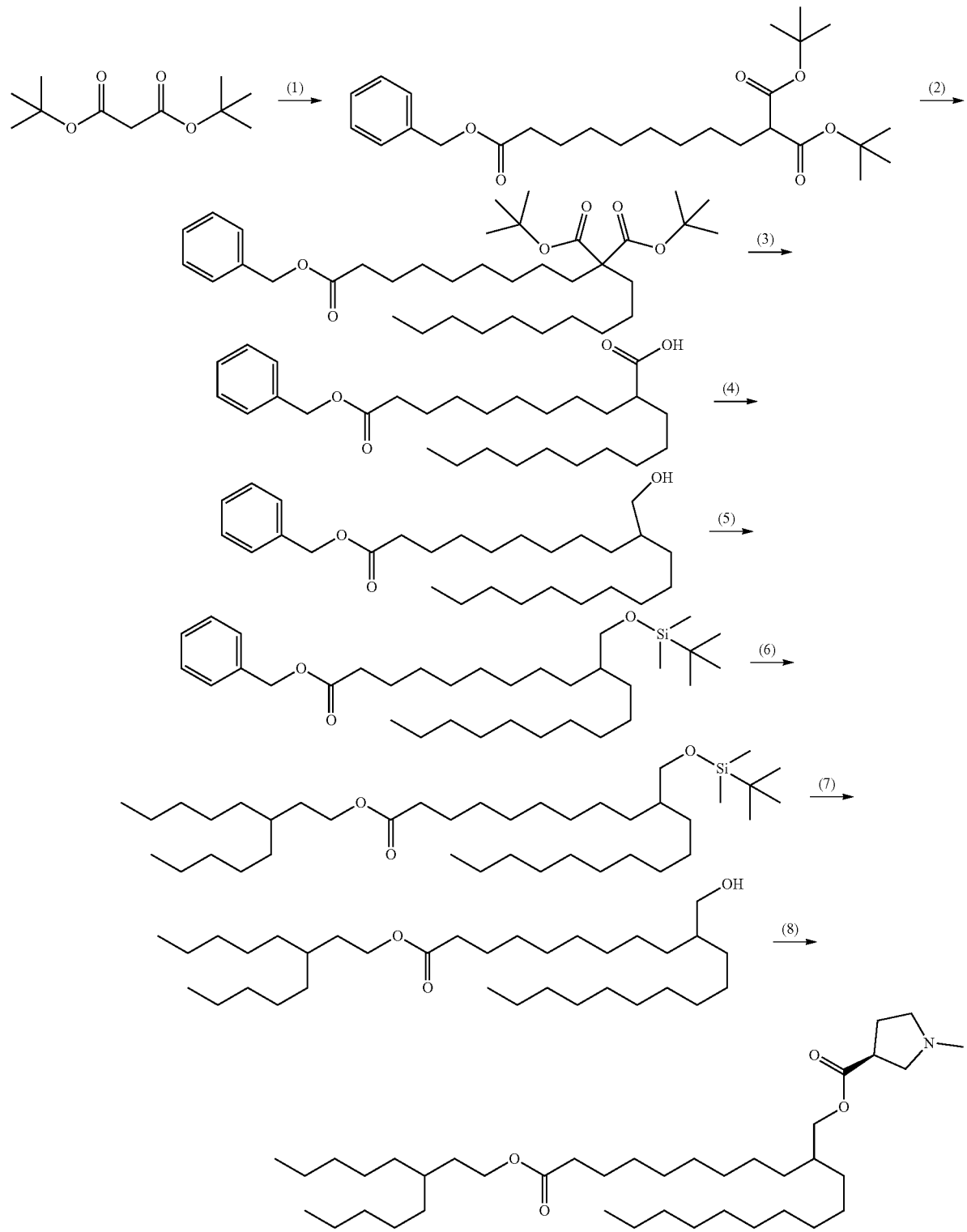

(1) Synthesis of 9-benzyl 1,1-di-tert-butyl nonane-1,1,9-tricarboxylate

Sodium hydride (60%, 0.43 g, 10.85 mmol) was suspended in DMF (40 mL), to which di-tert-butyl malonate (2.2 mL, 9.87 mmol) was gradually added under ice cooling, and the mixture was stirred for 5 minutes and for 20 minutes after the cooling bath was removed. Under ice cooling, sodium iodide (0.44 g, 2.96 mmol) and the compound (3.39 g, 10.36 mmol) obtained in Production Example 1 were sequentially added and stirred at room temperature for 15 hours. The reaction mixture was cooled in an ice water bath, added with water and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (3.6 g, 7.78 mmol).

$^1$H-NMR (600 MHz, CDCl$_3$) δ(ppm): 1.25-1.33 (m, 9H), 1.36 (s, 1H), 1.39 (s, 1H), 1.44-1.49 (m, 16H), 1.56-1.67 (m, 3H), 1.79 (q, J=6.7 Hz, 2H), 2.35 (t, J=7.5 Hz, 2H), 3.11 (t, J=7.7 Hz, 1H), 5.12 (s, 2H), 7.32-7.39 (m, 5H).

(2) Synthesis of 1-benzyl 9,9-di-tert-butyl nonadecane-1,9,9-tricarboxylate

The compound (3.6 g, 7.78 mmol) obtained in Example A-1-(1) was dissolved in DMF (36 mL), to which 60% sodium hydride (0.47 g, 11.67 mmol) was added under water cooling, and the mixture was stirred for 10 minutes and then for 20 minutes at room temperature. 1-Iododecane (3.3 mL, 15.56 mmol) was added and the mixture was stirred at room temperature for 4 hours. The reaction mixture was cooled in an ice water bath, added with a saturated ammonium chloride aqueous solution and extracted with n-heptane. The organic phase was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (3.4 g, 5.64 mmol).

$^1$H-NMR (400 MHz, CDCl$_3$) δ(ppm): 0.83-0.93 (m, 3H) 1.05-1.36 (m, 26H), 1.44 (s, 18H), 1.57-1.68 (m, 2H), 1.71-1.82 (m, 4H), 2.29-2.39 (m, 2H), 5.11 (s, 2H), 7.28-7.42 (m, 5H).

(3) Synthesis of 2-[9-(benzyloxy)-9-oxononyl]dodecanoic acid

The compound (3.4 g, 5.64 mmol) obtained in Example A-1-(2) was dissolved in methylene chloride (11.2 mL), to which TFA (5.6 mL) was added dropwise under ice cooling, and the mixture was stirred at room temperature for 1.5 hours. The reaction mixture was added with toluene and the solvent was removed by distillation under reduced pressure. The residue was dried by repeating addition and removal by distillation of toluene twice to obtain a crude product of 2-{9-[(2-butyloctyl)oxy]-9-oxononyl}-2-decylmalonic acid. The obtained crude product was dissolved in xylene (12 mL) and stirred at 150° C. for 8 hours. The reaction mixture was cooled to room temperature and concentrated under reduced pressure. The obtained residue was purified by column chromatography (n-heptane/ethyl acetate) to obtain the titled compound (2.26 g, 5.06 mmol).

$^1$H-NMR (400 MHz, CDCl$_3$) δ(ppm): 0.81-0.95 (m, 3H), 1.18-1.37 (m, 26H), 1.39-1.52 (m, 2H), 1.54-1.69 (m, 4H), 2.28-2.41 (m, 3H), 5.11 (s, 2H), 7.28-7.40 (m, 5H).

(4) Synthesis of benzyl 10-(hydroxymethyl)icosanoate

The compound (2.2 g, 4.93 mmol) obtained in Example A-1-(3) was dissolved in THF (25 mL), to which borane-THF complex (0.92, 8.0 mL, 7.39 mmol) was added dropwise at −15° C. and the mixture was stirred at 0° C. for 2 hours. A saturated sodium hydrogen carbonate aqueous solution was added, and the mixture was stirred at room temperature for 5 minutes and extracted with ethyl acetate. The organic phase was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (1.86 g, 4.30 mmol).

$^1$H-NMR (400 MHz, CDCl$_3$) δ(ppm): 0.81-0.95 (m, 3H), 1.12-1.38 (m, 31H), 1.39-0.5 (m, 1H), 1.58-1.72 (m, 2H), 2.23-2.36 (m, 2H), 3.48-3.59 (m, 2H), 5.11 (s, 2H), 7.28-7.41 (m, 5H).

(5) Synthesis of benzyl 10-{[(tert-butyldimethylsilyl)oxy]methyl}icosanoate

The compound (700 mg, 1.62 mmol) obtained in Example A-1-(4) was dissolved in DMF (3.2 mL), to which imidazole (165 mg, 2.43 mmol) was added and dissolved at room temperature. Under ice cooling, ten-butyldimethylsilyl chloride (293 mg, 1.94 mmol) was added and the mixture was stirred at room temperature for 3 hours. The reaction mixture was added with water and then extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (810 mg, 1.48 mmol).

$^1$H-NMR (40 MHz, CDCl$_3$) δ(ppm): 0.02 (s, 6H), 0.77-0.97 (m, 12H), 1.06-1.47 (m, 31H), 1.64 (br. s, 2H), 2.35 (t, J=7.5 Hz, 2H), 3.45 (d, J=5.7 Hz, 2H), 5.11 (s, 2H), 7.27-7.42 (m, 5H).

(6) Synthesis of 3-pentyloctyl 10-{[(ten-butyldimethylsilyl)oxy]methyl}icosanoate The compound (810 mg, 1.48 mmol) obtained in Example A-1-(5) was dissolved in ethyl acetate (10 mL), to which 10% palladium-carbon (158 mg, containing 50% water) was added at room temperature, and the mixture was stirred in a hydrogen atmosphere under normal pressure for 4.5 hours. The reaction mixture was filtered and washed with ethyl acetate. The filtrate was concentrated under reduced pressure to obtain a crude product of carboxylic acid (680 mg).

The obtained carboxylic acid, 3-pentyloctan-1-ol (CAS 1443519-63-8) (416 mg, 2.08 mmol) and DMAP (36 mg, 0.30 mmol) were dissolved in methylene chloride (7.4 mL), to which EDC.HCl (341 mg, 1.78 mmol) was added under ice cooling, and the mixture was stirred at room temperature for 16 hours. The reaction mixture was added with a saturated sodium hydrogen carbonate aqueous solution and extracted with ethyl acetate. The organic phase was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (926 mg, 1.45 mmol).

¹H-NMR (40 MHz, CDCl₃) δ(ppm): 0.02 (s, 5H), 0.88 (s, 17H), 1.12-1.46 (m, 46H), 1.55 (s, 8H), 2.21-2.34 (m, 2H), 3.39-3.52 (m, 2H), 4.00-4.13 (m, 2H).

(7) Synthesis of 3-pentyloctyl 10-(hydroxymethyl)icosanoate

The compound (925 mg, 1.45 mmol) obtained in Example A-1-(6) was dissolved in THF (4.5 mL), to which a TBAF/THF solution (1M, 3.6 mL) was gradually added under ice cooling, and the mixture was stirred at room temperature for 1 hour. The reaction mixture was added with water and extracted with ethyl acetate. The organic phase was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (584 mg, 1.11 mmol).

¹H-NMR (400 MHz, CDCl₃) δ(ppm): 0.78-0.99 (m, 9H), 1.26 (d, J=2.9 Hz, 55H), 1.50-1.75 (m, 8H), 2.28 (t, J=7.6 Hz, 2H), 3.53 (s, 2H), 4.08 (t, J=7.0 Hz, 2H).

(8) Synthesis of (3S)-2-{9-oxo-9-[(3-pentyloctyl)oxy]nonyl}dodecyl 1-methylpyrrolidine-3-carboxylate The compound (50 mg, 0.095 mmol) obtained in Example A-1-(7), DIPEA (0.036 mL, 0.21 mmol), (3S)-1-methylpyrrolidine-3-carboxylic acid hydrochloride (32 mg, 0.19 mmol) and DMAP (2.3 mg, 0.019 mmol) were dissolved in methylene chloride (0.8 mL), to which EDC.HCl (40 mg, 0.21 mmol) was added under ice cooling, and the mixture was stirred at room temperature for 15 hours. The reaction mixture was added with a saturated sodium hydrogen carbonate aqueous solution and extracted with ethyl acetate. The organic phase was washed with a saturated sodium chloride solution and dried over anhydrous magnesium sulphate. Following filtration, the solvent was removed by distillation under reduced pressure. The residue was purified by silica gel column chromatography (n-heptane/ethyl acetate/methanol) to obtain the titled compound (47 mg, 0.074 mmol).

¹H-NMR (400 MHz, CDCl₃) δ(ppm): 0.82-0.96 (m, 9H), 1.14-1.48 (m, 49H), 1.51-1.73 (m, 4H), 2.03-2.16 (m, 2H), 2.28 (t, J=7.5 Hz, 2H), 2.35 (s, 3H), 2.49 (d, J=9.0 Hz, 1H), 2.58-2.71 (m, 2H), 2.76-2.92 (m, 1H), 2.97-3.12 (m, 1H), 3.98 (d, J=5.7 Hz, 2H), 4.08 (s, 2H).

Synthesis of Cationic Lipid (2)

Example A-2

Synthesis of (3R)-2-{9-oxo-9-[(3-pentyloctyl)oxy]nonyl}dodecyl 1-methylpyrrolidine-3-carboxylate (Cationic Lipid 2)

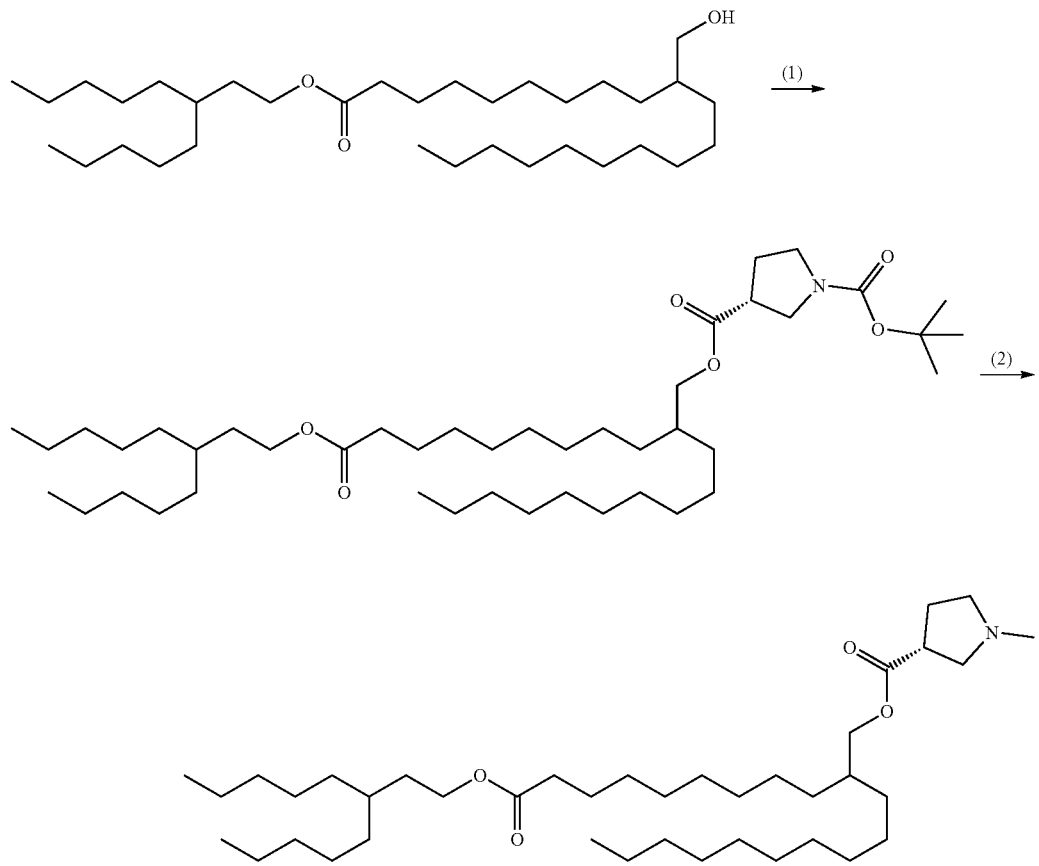

(1) Synthesis of (3R)-1-tert-butyl 3-(2-{9-oxo-9-[(3-pentyloctyl)oxy]nonyl}dodecyl)pyrrolidine-1,3-dicarboxylate According to the method in Example A-1-(8), the titled compound (80 mg, 0.11 mmol) was obtained from the compound (60 mg, 0.11 mmol) obtained in Example A-1-(7), (R)-1-(tert-butoxycarbonyl)pyrrolidine-3-carboxylic acid (49 mg, 0.23 mmol). EDC.HCl (48 mg, 0.25 mmol), DIPEA (0.039 mL, 0.23 mmol). DMAP (2.8 mg, 0.023 mmol) and methylene chloride (0.80 mL).

$^1$H-NMR (400 MHz, CDCl$_3$) δ(ppm): 0.88 (t, J=7.0 Hz, 9H), 1.10-1.38 (m, 53H), 1.46 (s, 9H), 1.50-1.72 (m, 4H), 1.99-2.19 (m, 2H), 2.28 (s, 2H), 2.90-3.17 (m, 1H), 3.24-3.75 (m, 4H), 3.97-4.03 (m, 2H), 4.05-4.12 (m, 2H).

(2) Synthesis of (3R)-2-{9-oxo-9-[(3-pentyloctyl)oxy]nonyl}dodecyl 1-methylpyrrolidine-3-carboxylate The compound (80 mg, 0.11 mmol) obtained in Example A-2-(1) was dissolved in methylene chloride (2.2 mL), to which TFA (1.1 mL) was added dropwise at room temperature, and the mixture was stirred for 0.5 hours. To the reaction mixture was added toluene, and the solvent was removed by distillation under reduced pressure. The residue was dissolved in methylene chloride (I mL), to which a formaldehyde solution (37%, 0.25 mL, 3.3 mmol) and sodium sulphate (0.79 g, 5.54 mmol) were added at room temperature, and the mixture was stirred for 10 minutes. Sodium tri(acetoxy)borohydride (117 mg, 0.55 mmol) was added and the mixture was stirred at room temperature for 16 hours. The reaction mixture was added with a saturated sodium hydrogen carbonate aqueous solution and extracted with chloroform. The organic phase was washed with a saturated sodium chloride solution and dried over anhydrous magnesium sulphate. Following filtration, the solvent was removed by distillation under reduced pressure. The residue was purified by silica gel column chromatography (ethyl acetate/methanol) to obtain the titled compound (20 mg, 0.031 mmol).

$^1$H-NMR (400 MHz, CDCl$_3$) δ(ppm): 0.82-0.96 (m, 9H), 1.14-1.48 (m, 49H), 1.51-1.73 (m, 4H), 2.03-2.16 (m, 2H), 2.23-2.32 (m, 2H), 2.35 (s, 3H), 2.49 (d, J=9.0 Hz, 1H), 2.58-2.71 (m, 2H), 2.76-2.92 (m, 1H), 2.97-3.12 (m, 1H), 3.98 (d, J=5.7 Hz, 2H), 4.04-4.12 (m, 2H).

Synthesis of Cationic Lipid (3)

Example A-3

Synthesis of 2-{9-oxo-9-[(3-pentyloctyl)oxy]nonyl}dodecyl 1-methylpyrrolidine-3-carboxylate (cationic lipid 3)

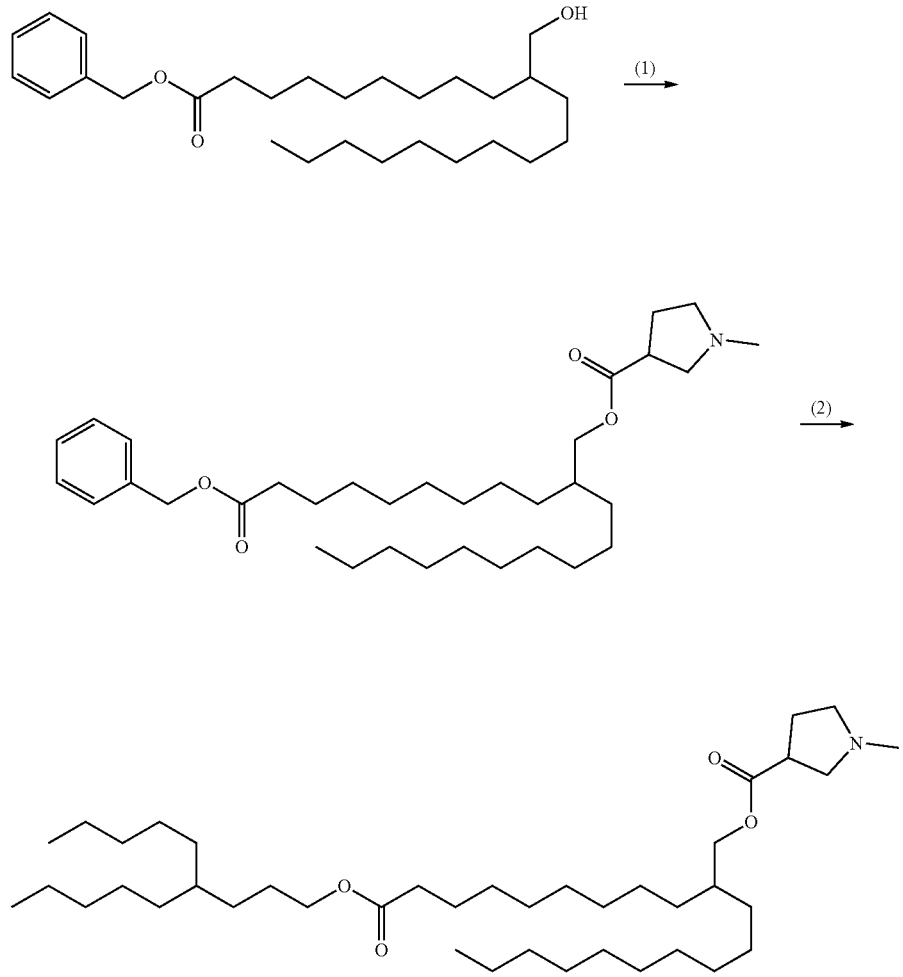

(1) Synthesis of 2-[9-(benzyloxy)-9-oxononyl]dodecyl 1-methylpyrrolidine-3-carboxylate The compound (0.20 g, 0.46 mmol) obtained in Example A-1-(4), DIPEA (0.161 mL, 0.92 mmol) and 1-methylpyrrolidine-3-carboxylic acid hydrochloride (0.15 g, 0.92 mmol) were dissolved in methylene chloride (2.0 mL), to which EDC.HCl (0.19 g, 1.02 mmol) was added and the mixture was stirred at room temperature for 18 hours. The reaction mixture was concentrated under reduced pressure and the residue was then purified by silica gel column chromatography (ethyl acetate/methanol) to obtain the titled compound (0.15 g, 0.28 mmol).

$^1$H-NMR (600 MHz, CDCl$_3$) δ(ppm): 0.89 (t, J=7.0 Hz, 3H), 1.27 (s, 40H), 1.61-1.67 (m, 3H), 1.74-1.86 (m, 1H), 2.07-2.13 (m, 2H), 2.34-2.38 (m, 6H), 2.47-2.52 (m, 1H), 2.61-2.66 (m, 2H), 2.85 (t, J=8.8 Hz, 1H), 3.02-3.07 (m, 1H), 3.99 (d, J=5.9 Hz, 2H), 5.08 (s, 1H), 5.12 (s, 2H), 7.31-7.38 (m, 5H).

(2) Synthesis of 2-{9-oxo-9-[(4-pentylnonyl)oxy]nonyl}dodecyl 1-methylpyrrolidine-3-carboxylate According to Example A-1-(6), a crude product of carboxylic acid was obtained from the compound (0.15 g, 0.28 mmol) obtained in Example A-3-(1), 10% palladium/carbon (0.30 g. containing 50% water) and ethyl acetate (5 mL).

The titled compound (0.081 g, 0.14 mmol) was obtained from the obtained carboxylic acid, the compound (0.048 g, 0.23 mmol) obtained in Production Example 2-(4), EDC.HCl (0.086 g, 0.45 mmol), DMAP (0.005 g, 0.05 mmol) and methylene chloride (1.0 mL).

$^1$H-NMR (600 MHz, CDCl$_3$) δ(ppm): 0.86-0.91 (m, 9H), 1.20-1.33 (m, 54H), 1.56-1.65 (m, 5H), 2.05-2.14 (m, 2H), 2.29 (t, J=7.7 Hz, 2H), 2.36 (s, 3H), 2.50 (q, J=7.7 Hz, 1H), 2.60-2.67 (m, 2H), 2.86 (t, J=8.8 Hz, 1H), 3.01-3.07 (m, 1H), 3.99 (d, J=5.9 Hz, 2H), 4.05 (t, J=6.8 Hz, 2H), 4.52 (d, J=4.8 Hz, 1H), 5.30 (s, 1H), 5.40 (br d, J=4.0 Hz, 1H), 5.47-5.53 (m, 1H).

Synthesis of Cationic Lipid (4)

Example A-4

(1) Synthesis of 2-nonyl-11-oxo-11-[(3-pentyloctyl)oxy]undecyl 1-methylpyrrolidine-3-carboxylate (Cationic Lipid 4)

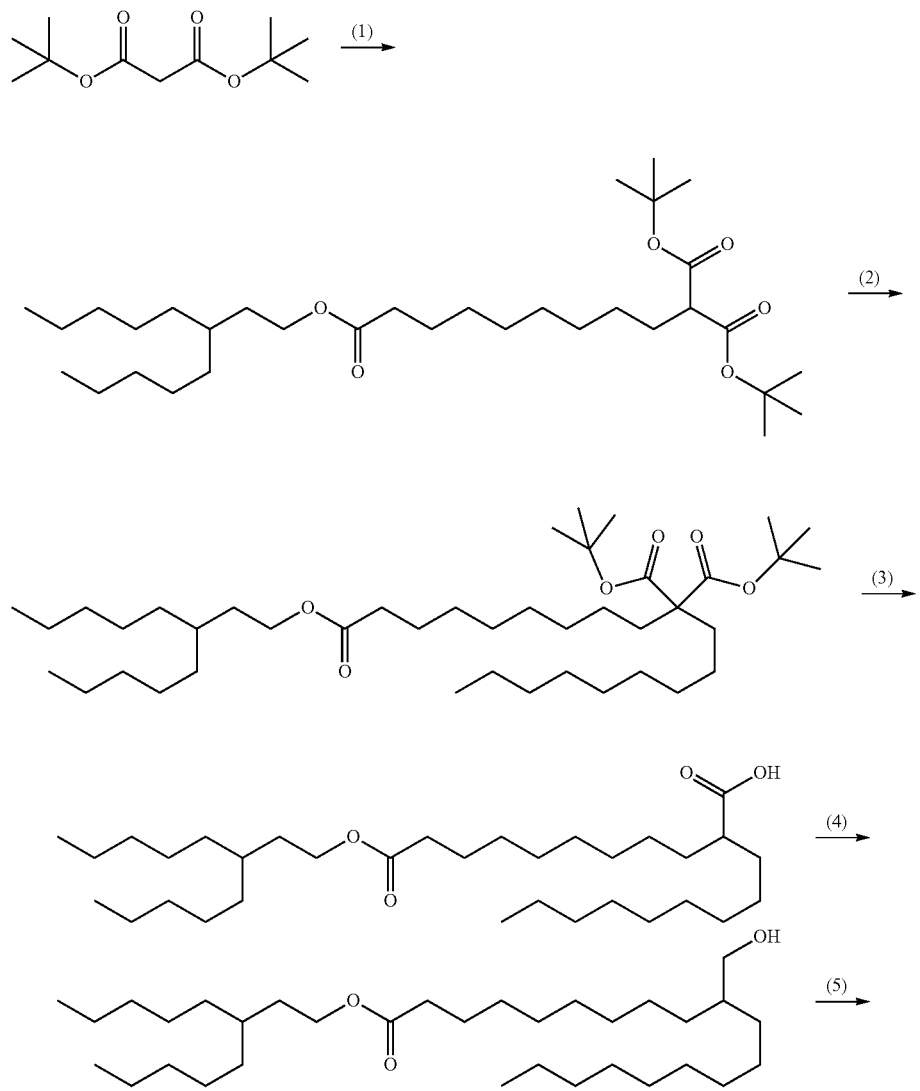

-continued

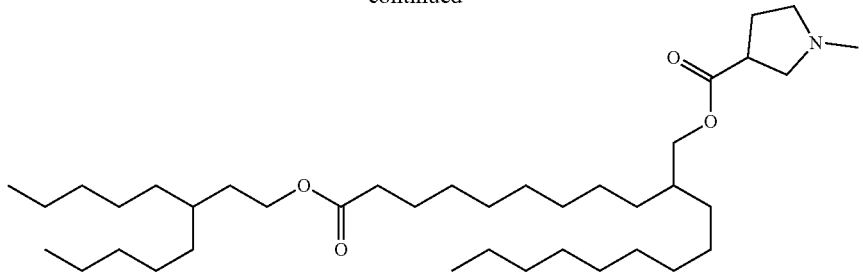

(1) Synthesis of 1,1-di-tert-butyl 9-(3-pentyloctyl) nonane-1,1,9-tricarboxylate Di-tert-butyl malonate (1.20 g, 5.56 mmol) was dissolved in THF (26 mL), to which 60% sodium hydride (0.22 g, 5.56 mmol) was added under ice cooling, and the mixture was stirred for 15 minutes. The mixture was stirred at room temperature for 10 minutes and then added with a solution of the compound (2.22 g, 5.29 mmol) obtained in Production Example 3 in THF (3 mL). The mixture was stirred at room temperature for 18 hours, added with water and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (cyclohexane/diethyl ether) to obtain the titled compound (1.79 g, 3.39 mmol).

$^1$H-NMR (600 MHz, CDCl$_3$) δ(ppm): 0.89 (t, J=7.2 Hz, 6H), 1.26 (br s, 12H), 1.27-1.34 (m, 13H), 1.46 (s, 13H), 1.48 (s, 8H), 1.54-1.64 (m, 5H), 1.79 (br d, J=7.0 Hz, 2H), 2.28 (t, J=7.5 Hz, 2H), 3.11 (t, J=7.7 Hz, 1H), 3.19 (s, 1H), 3.41 (s, 1H), 4.08 (t, J=7.2 Hz, 2H).

(2) Synthesis of 9,9-di-tert-butyl 1-(3-pentyloctyl) octadecane-1,9,9-tricarboxylate The compound (0.96 g, 1.72 mmol) obtained in Example A-4-(1) was dissolved in THF (7.6 mL), to which 60% sodium hydride (0.076 g, 1.89 mmol) was added under ice cooling, and the mixture was stirred for 20 minutes. After stirring at room temperature for 20 minutes, a solution of 1-iodononane (0.44 g, 1.72 mmol) in THF (2 mL) was added. After reflux under heating for 6 hours, water was added and extracted with diethyl ether. The organic phase was washed with a saturated sodium chloride solution and dried over magnesium sulphate. Following filtration, the solvent was removed by distillation under reduced pressure. The residue was purified by silica gel column chromatography (cyclohexane/diethyl ether) to obtain the titled compound (0.59 g, 0.86 mmol).

$^1$H-NMR (600 MHz, CDCl$_3$) δ(ppm): 0.83-0.94 (m, 12H), 1.13 (br s, 6H), 1.27 (br d, J=16.5 Hz, 43H), 1.31-1.36 (m, 4H), 1.41-1.48 (m, 28H), 1.51-1.65 (m, 5H), 1.70-1.85 (m, 6H), 2.22-2.34 (m, 2H), 4.02-4.15 (m, 2H).

(3) Synthesis of 2-nonyl-11-oxo-11-[(3-pentyloctyl) oxy]undecanoic acid

According to the method in Example A-1-(3), the titled compound (0.18 g, 0.35 mmol) was obtained from the compound (0.59 g, 0.86 mmol) obtained in Example A-4-(2), methylene chloride (2 mL), TFA (1 mL) and xylene (2 mL).

$^1$H-NMR (600 MHz, CDCl$_3$) δ(ppm): 0.84-0.92 (m, 9H), 1.17-1.33 (m, 42H), 1.36-1.51 (m, 4H), 1.54-1.66 (m, 6H), 2.24-2.37 (m, 3H), 4.09 (t, J=7.2 Hz, 2H).

(4) Synthesis of 3-pentyloctyl 10-(hydroxymethyl)nonadecanoate

According to the method in Production Example 2-(1), the titled compound (0.068 g, 0.14 mmol) was obtained from the compound (0.093 g, 0.18 mmol) obtained in Example A-4-(3), borane-THF complex (1M, 0.35 mL, 0.35 mmol), borane-THF complex (1M, 0.53 mL, 0.53 mmol) and THF (2.0 mL).

$^1$H-NMR (600 MHz, CDCl$_3$) δ(ppm): 0.87-0.90 (m, 10H), 1.27 (br dd, J=1.4, 7.3 Hz, 52H), 1.40-1.46 (m, 7H), 1.56-1.63 (m, 4H), 2.28 (t, J=7.5 Hz, 2H), 3.53 (d, J=5.5 Hz, 2H), 4.08 (t, J=7.2 Hz, 2H).

(5) Synthesis of 2-nonyl-11-oxo-11-[(3-pentyloctyl) oxy]undecyl 1-methylpyrrolidine-3-carboxylate The compound (0.069 g, 0.13 mmol) obtained in Example A-4-(4), DIPEA (0.047 mL, 0.27 mmol), 1-methylpyrrolidine-3-carboxylic acid hydrochloride (0.044 g, 0.27 mmol) and DMAP (3 mg, 0.03 mmol) were dissolved in methylene chloride (I mL) and THF (1 mL), to which EDC.HCl (0.057 g, 0.30 mmol) was added, and the mixture was stirred at room temperature for 18 hours. The reaction mixture was concentrated under reduced pressure and the residue was purified by silica gel column chromatography (ethyl acetate/methanol) to obtain the titled compound (0.046 g, 0.072 mmol).

$^1$H-NMR (600 MHz, CDCl$_3$) δ(ppm): 0.89 (t, J=7.0 Hz, 3H), 0.89 (t, J=7.2 Hz, 6H), 1.19-1.33 (m, 46H), 1.41 (br s, 1H), 1.58 (q, J=7.0 Hz, 2H), 1.60-1.66 (m, 3H), 1.70 (br s, 1H), 2.07-2.17 (m, 2H), 2.29 (t, J=7.5 Hz, 2H), 2.36 (s, 3H), 2.50 (q, J=8.0 Hz, 1H), 2.58-2.69 (m, 2H), 2.85 (t, J=9.0 Hz, 1H), 3.05 (tt, J=8.8, 6.7 Hz, 1H), 3.99 (d, J=5.9 Hz, 2H), 4.09 (t, J=7.2 Hz, 2H).

55

Synthesis of Cationic Lipid (5)

Example A-5

Synthesis of 2-{6-[(3-octylundecyl)oxy]-6-oxohexyl}dodecyl 1-methylpyrrolidine-3-carboxylate (Cationic Lipid 5)

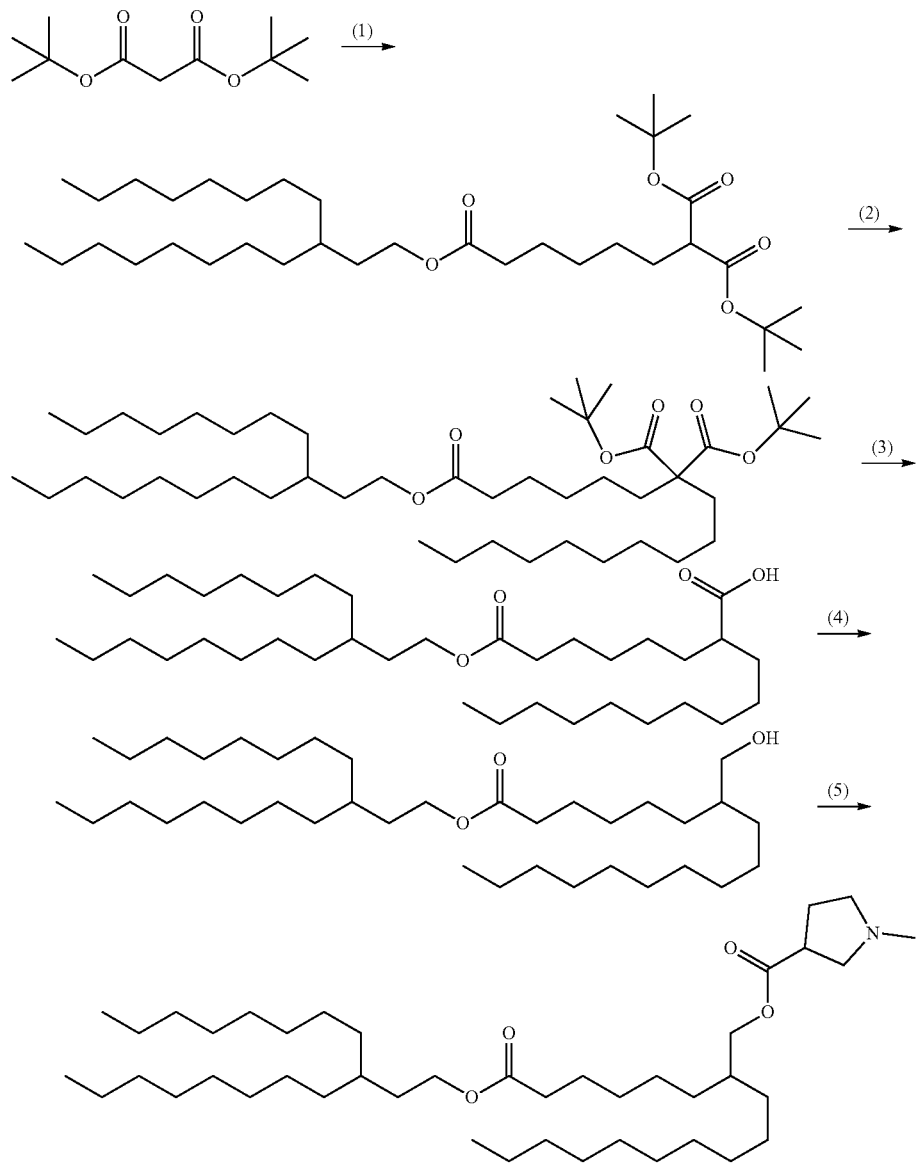

with a saturated sodium chloride solution and dried over anhydrous magnesium sulphate. Following filtration, the solvent was removed by distillation under reduced pressure. The residue was purified by silica gel column chromatography (cyclohexane/diethyl ether) to obtain the titled compound (2.9 g, 5.10 mmol).

(1) Synthesis of 1,1-di-tert-butyl (6-(3-octylundecyl)hexane-1,1,6-tricarboxylate Sodium hydride (60%, 0.43 g, 10.62 mmol) was suspended in THF (21 mL), to which di-tert-butyl malonate (2.4 mL, 10.6 mmol) was added dropwise under ice cooling. The mixture was heated to room temperature over 30 minutes, added with the compound (4.67 g, 10.12 mmol) obtained in Production Example 5 and sodium iodide (0.15 g, 1.01 mmol) under ice cooling, and stirred at room temperature for 18 hours. The reaction mixture was added with water and extracted with diethyl ether. The organic phase was washed $^1$H-NMR (600 MHz, CDCl$_3$) δ(ppm): 0.88 (t, J=7.0 Hz, 6H), 1.19-1.31 (m, 31H), 1.31-1.36 (m, 5H), 1.41-1.51 (m, 26H), 1.55-1.58 (m, 2H), 1.59-1.67 (m, 2H), 1.79 (q, J=7.3 Hz, 2H), 2.27 (t, J=7.5 Hz, 2H), 3.10 (t, J=7.5 Hz, 1H), 4.07 (t, J=7.2 Hz, 2H).

(2) Synthesis of 6,6-di-tert-butyl 1-(3-octylundecyl) hexadecane-1,6,6-tricarboxylate According to the method in Example A-4-(2), the titled compound (0.99 g, 1.32 mmol) was obtained from the compound (2.25 g, 3.78 mmol) obtained in Example A-5-

(1), i-iododecane (1.0 g, 3.78 mmol), 60% sodium hydride (0.17 g, 4.15 mmol) and THF (16.7 mL).

$^1$H-NMR (600 MHz, CDCl$_3$) δ(ppm): 0.01 (s, 1H), 0.89 (td, J=7.1, 2.8 Hz, 9H), 1.06-1.23 (m, 6H), 1.26 (br d, J=7.0 Hz, 34H), 1.30-1.37 (m, 5H), 1.40 (br s, 1H), 1.42-1.49 (m, 18H), 1.52-1.65 (m, 6H), 1.71-1.85 (m, 4H), 2.28 (t, J=7.5 Hz, 2H), 4.08 (t, J=7.2 Hz, 2H).

(3) Synthesis of 2-{6-[(3-octylundecyl)oxy]-6-oxohexyl}dodecanoic acid

According to the method in Example A-1-(3), a crude product (1.01 g) of dicarboxylic acid was obtained from the compound (0.99 g, 1.34 mmol) obtained in Example A-5-(2), methylene chloride (3 mL) and TFA (1.4 mL). The titled compound (0.31 g, 0.55 mmol) was obtained from the obtained crude product (0.84 g) and xylene (3 mL).

$^1$H-NMR (600 MHz, CDCl$_3$) δ(ppm): 0.89 (t, J=7.0 Hz, 11H), 1.23-1.36 (m, 60H), 1.40 (br s, 1H), 1.48 (br dd, J=13.8, 6.1 Hz, 2H), 1.56-1.66 (m, 7H), 2.29 (t, J=7.5 Hz, 2H), 2.33-2.36 (m, 1H), 4.09 (t, J=7.2 Hz, 2H).

(4) Synthesis of 3-octylundecyl 7-(hydroxymethyl)heptadecanoate

According to the method in Production Example 2-(1), the titled compound (0.19 g, 0.33 mmol) was obtained from the compound (0.31 g, 0.54 mmol) obtained in Example A-5-(3), borane-THF complex (1 M, 1.1 mL, 1.1 mmol) and THF (6.0 mL).

$^1$H-NMR (600 MHz, CDCl$_3$)(ppm): 0.89 (t, J=7.0 Hz, 10H), 1.22-1.37 (m, 55H), 1.40 (br s, 1H), 1.43-1.47 (m, 1H), 1.57 (q, J=6.6 Hz, 3H), 1.61-1.70 (m, 2H), 2.29 (t, J=7.5 Hz, 2H), 3.54 (d, J=5.5 Hz, 2H), 4.09 (t, J=7.2 Hz, 2H).

(5) Synthesis of 2-{6-[(3-octylundecyl)oxy]-6-oxohexyl}dodecyl 1-methylpyrrolidine-3-carboxylate According to the method in Example A-4-(5), the titled compound (0.055 g, 0.083 mmol) was obtained from the compound (0.19 g, 0.33 mmol) obtained in Example A-5-(4), 1-methylpyrrolidine-3-carboxylic acid hydrochloride (0.11 g, 0.67 mmol), EDC.HCl (0.14 g, 0.73 mmol), DIPEA (0.116 mL, 0.67 mmol), DMAP (8 mg, 0.07 mmol) and methylene chloride (1.5 mL).

$^1$H-NMR (600 MHz, CDCl$_3$) δ(ppm): 0.89 (t, J=7.0 Hz, 9H), 1.20-1.34 (m, 53H), 1.40 (br s, 1H), 1.57 (q, J=6.8 Hz, 2H), 1.61-1.66 (m, 3H), 2.05-2.17 (m, 2H), 2.29 (t, J=7.5 Hz, 2H), 2.37 (s, 3H), 2.45-2.56 (m, 1H), 2.64 (dd, J=9.5, 7.0 Hz, 1H), 2.68 (dt, J=9.1, 6.5 Hz, 1H), 2.90 (t, J=8.8 Hz, 1H), 3.0 (quin, J=7.8 Hz, 1H), 3.99 (d, J=5.9 Hz, 2H), 4.08 (t, J=7.2 Hz, 2H).

Synthesis of Cationic Lipid (6)

Example A-6

Synthesis of 2-{4-[(4-nonyltridecyl)oxy]-4-oxobutyl}dodecyl 1-methylpyrrolidine-3-carboxylate (Cationic Lipid 6)

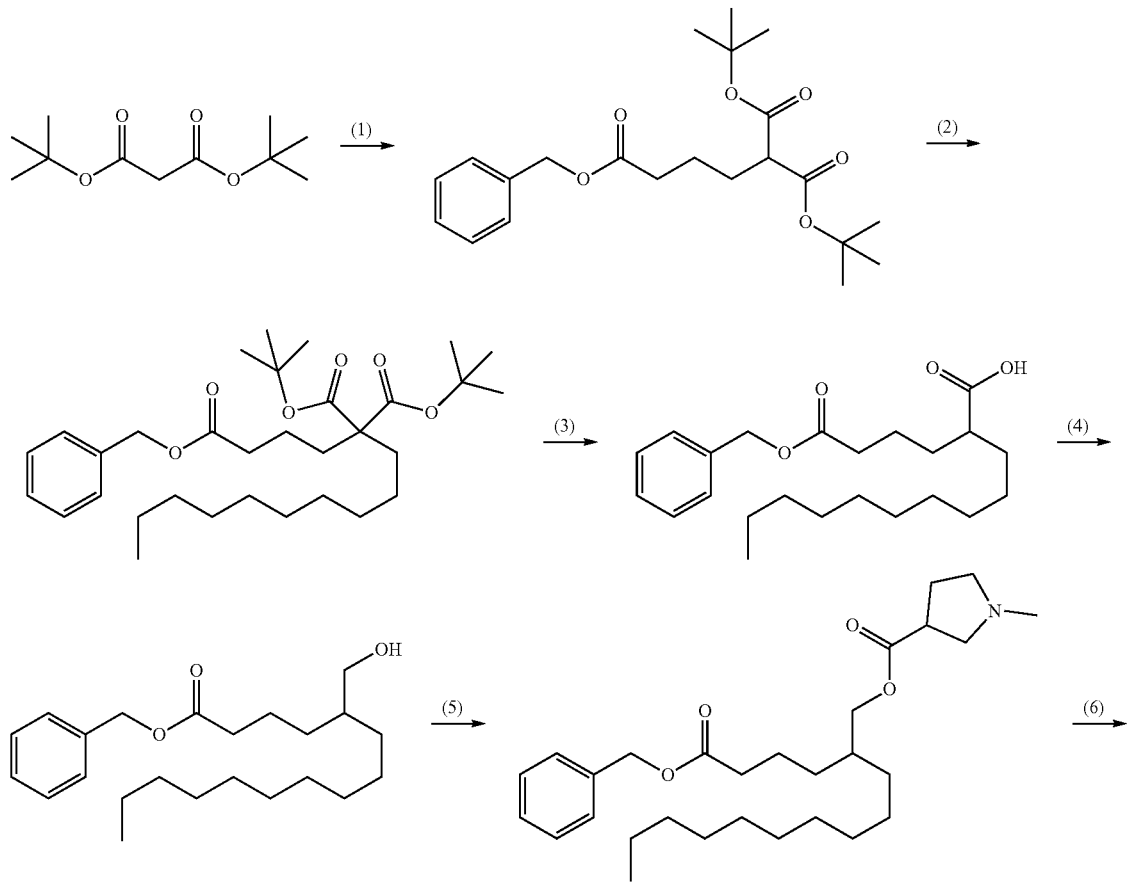

-continued

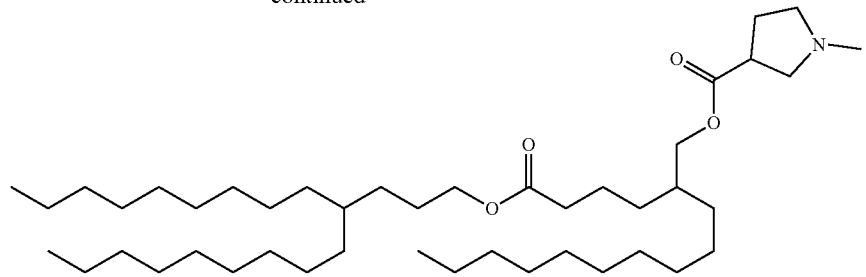

(1) Synthesis of 4-benzyl 1,1-di-tert-butyl butane-1,1,4-tricarboxylate

According to the method in Example A-4-(1), the titled compound (2.93 g, 7.46 mmol) was obtained from di-tert-butyl malonate (2.65 g, 12.25 mmol), THF (58 mL), 60%/o sodium hydride (0.49 g, 12.25 mmol) and the compound (3.00 g, 11.67 mmol) obtained in Production Example 6.

$^1$H-NMR (600 MHz, CDCl$_3$) δ(ppm): 1.43-1.48 (m, 20H), 1.66-1.72 (m, 2H), 1.82-1.86 (m, 2H), 2.4 (t, J=7.5 Hz, 2H), 3.13 (t, J=7.5 Hz, 1H), 5.12 (s, 2H), 7.31-7.38 (m, 5H).

(2) Synthesis of 1-benzyl 4,4-di-tert-butyl tetradecane-1,4,4-tricarboxylate The compound (2.93 g, 7.46 mmol) obtained in Example A-6-(1) was dissolved in THF (38 mL), to which 60% sodium hydride (0.31 g, 7.83 mmol) was added under ice cooling, and the mixture was stirred for 1 hour. A solution of 1-iododecane (2.10 g, 7.83 mmol) in THF (5 mL) was added and refluxed under heating overnight. Water was added and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (cyclohexane/diethyl ether) to obtain the titled compound (2.59 g, 4.85 mmol).

$^1$H-NMR (600 MHz, CDCl$_3$) δ(ppm): 0.89 (t, J=7.2 Hz, 3H), 1.09-1.20 (m, 2H), 1.22-1.33 (m, 15H), 1.45 (s, 18H), 1.48-1.56 (m, 2H), 1.59 (s, 1H), 1.76-1.84 (m, 4H), 2.37 (t, J=7.3 Hz, 2H), 5.12 (s, 2H), 7.32-7.38 (m, 5H).

(3) Synthesis of 2-[4-(benzyloxy)-4-oxobutyl]dodecanoic acid

According to the method in Example A-1-(3), a crude product (2.34 g) of dicarboxylic acid was obtained from the compound (2.59 g, 4.87 mmol) obtained in Example A-6-(2), methylene chloride (11 mL) and TFA (5 mL). The titled compound (1.58 g, 4.21 mmol) was obtained from the obtained crude product (2.05 g) and xylene (11 mL).

$^1$H-NMR (600 MHz, CDCl$_3$) δ(ppm): 0.89 (t, J=7.0 Hz, 3H), 1.07-1.22 (m, 1H), 1.24-1.32 (m, 16H), 1.41-1.57 (m, 2H), 1.60-1.74 (m, 4H), 2.34-2.41 (m, 3H), 5.10-5.15 (m, 2H), 7.31-7.40 (m, 5H).

(4) Synthesis of 2-{4-[(4-nonyltridecyl)oxy]-4-oxobutyl}dodecyl 1-methylpyrrolidine-3-carboxylate According to the method in Production Example 2-(1), the titled compound (1.29 g, 3.54 mmol) was obtained from the compound (1.58 g, 4.21 mmol) obtained in Example A-6-(3), borane-THF complex (1M, 8.4 mL, 8.4 mmol) and THF (48 mL).

$^1$H-NMR (600 MHz, CDCl$_3$) δ(ppm): 0.89 (t, J=7.0 Hz, 3H), 1.24-1.34 (m, 22H), 1.35-1.42 (m, 2H), 1.46-1.5 (m, 1H), 1.67 (quin, J=7.7 Hz, 3H), 2.36-2.39 (m, 2H), 3.51-3.58 (m, 2H), 5.13 (s, 2H), 7.32-7.39 (m, 5H).

(5) Synthesis of 2-[4-(benzyloxy)-4-oxobutyl]dodecyl 1-methylpyrrolidine-3-carboxylate According to the method in Example A-4-(5), the titled compound (0.33 g& 0.71 mmol) was obtained from the compound (0.50 g, 1.4 mmol) obtained in Example A-6-(4), l-methylpyrrolidine-3-carboxylic acid hydrochloride (0.46 g, 2.76 mmol). EDC.HCl (0.58 g, 3.03 mmol), DIPEA (0.48 mL, 2.76 mmol), DMAP (34 mg, 0.28 mmol) and methylene chloride (2 mL).

$^1$H-NMR (600 MHz, CDCl$_3$) δ(ppm): 0.88 (t, J=7.0 Hz, 3H), 1.23-1.36 (m, 23H), 1.42 (s, 5H), 1.63-1.69 (m, 3H), 1.85 (dt, J=6.3, 3.3 Hz, 1H), 2.06-2.11 (m, 2H), 2.33-2.36 (m, 6H), 2.49 (q, J=7.7 Hz, 1H), 2.59-2.64 (m, 2H), 2.82 (t, J=8.8 Hz, 1H), 2.94 (s, 1H), 3.02 (br t, J=8.3 Hz, 1H), 3.74 (br t, J=6.2 Hz, 1H), 3.96-4.00 (m, 2H), 5.11 (s, 2H), 7.31-7.37 (m, 5H).

(6) Synthesis of 2-{4-[(4-nonyltridecyl)oxy]-4-oxobutyl}dodecyl 1-methylpyrrolidine-3-carboxylate According to Example A-1-(6), a crude product (0.15 g) of carboxylic acid was obtained from the compound (0.18 g, 0.37 mmol) obtained in Example A-6-(5), 10% palladium/carbon (0.20 g. containing 50% water) and ethyl acetate (9 mL).

The titled compound (9 mg, 0.014 mmol) was obtained from the obtained carboxylic acid (0.086 g, 0.23 mmol), the compound (0.050 g, 0.16 mmol) obtained in Production Example 7-(7). EDC.HCl (0.086 g, 0.45 mmol), DIPEA (0.074 mL, 0.45 mmol) and methylene chloride (1.0 mL).

$^1$H-NMR (600 MHz, CDCl$_3$) δ(ppm): 0.89 (t, J=7.0 Hz, 9H), 1.21-1.37 (m, 57H), 1.57-1.70 (m, 7H), 2.06-2.15 (m, 2H), 2.3 (t, J=7.5 Hz, 2H), 2.36 (s, 3H), 2.45-2.57 (m, 1H), 2.64 (ddd, J=9.4, 6.8, 2.9 Hz, 2H), 2.85 (t, J=8.8 Hz, 1H), 3.00-3.08 (m, 1H), 3.97-4.07 (m, 4H).

61
Synthesis of Cationic Lipid (7)
Example A-7
Synthesis of bis(3-nonyldodecyl) 6-{[(1-methylpyrrolidine-3-carbonyl)oxy]methyl}undecanedioate (Cationic Lipid 7)
62
(1) Synthesis of 5-benzyl 1,1-di-tert-butyl pentane-1,1,5-tricarboxylate
According to the method in Example A4-(1), the titled compound (2.09 g, 5.77 mmol) was obtained from di-tert-butyl malonate (2.34 g, 10.84 mmol), THF (52 mL), 60%
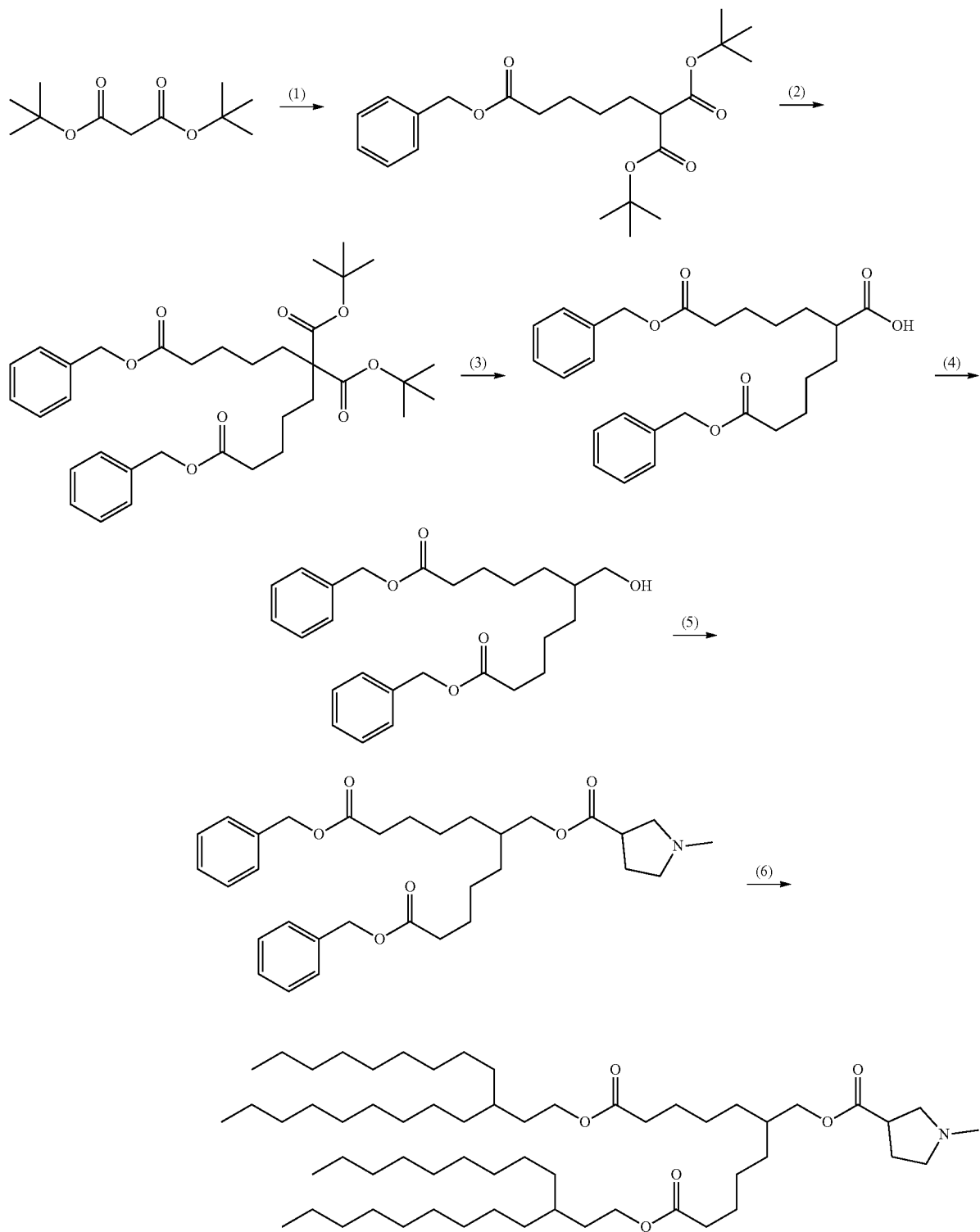

sodium hydride (0.26 g, 10.8 mmol) and the compound (2.8 g, 10.3 mmol) obtained in Production Example 8.

$^1$H-NMR (600 MHz, CDCl$_3$) δ(ppm): 1.26-1.41 (m, 3H), 1.43-1.49 (m, 20H), 1.55-1.60 (m, 1H), 1.69 (quin, J=7.6 Hz, 2H), 1.78-1.86 (m, 2H), 2.37 (t, J=7.5 Hz, 2H), 3.11 (t, J=7.5 Hz, 1H), 5.11 (s, 2H), 7.31-7.40 (m, 5H).

(2) Synthesis of 1,9-dibenzyl 5,5-di-tert-butyl nonane-1,5,5,9-tetracarboxylate The compound (2.09 g, 5.14 mmol) obtained in Example A-7-(1) was dissolved in THF (23 mL), to which 60% sodium hydride (0.23 g, 5.66 mmol) and sodium iodide (0.077 g, 0.51 mmol) were sequentially added at room temperature, and the mixture was stirred for 30 minutes. The reaction mixture was added with a solution of the compound (1.39 g, 5.14 mmol) obtained in Production Example 8 in THF (2 mL) and heated at 65° C. After 3 days, iced water was added and extracted with diethyl ether. The organic phase was washed with a saturated sodium chloride solution and dried over anhydrous magnesium sulphate. Following filtration, the solvent was removed by distillation under reduced pressure. The residue was purified by silica gel column chromatography (diethyl ether/n-pentane) to obtain the titled compound (2.27 g, 3.80 mmol).

$^1$H-NMR (600 MHz, CDCl$_3$) δ(ppm): 1.13-1.20 (m, 4H), 1.42 (s, 17H), 1.58-1.70 (m, 4H), 1.74-1.80 (m, 4H), 2.35 (t, J=7.6 Hz, 4H), 5.10 (s, 4H), 7.29-7.39 (m, 10H).

(3) Synthesis of 7-(benzyloxy)-2-[5-(benzyloxy)-5-oxopentyl]-7-oxopentanoic Acid According to the method in Example A-1-(3), a crude product (2.02 g) of dicarboxylic acid was obtained from the compound (2.27 g, 3.80 mmol) obtained in Example A-7-(2), methylene chloride (9 mL) and TFA (4.1 mL). The titled compound (1.47 g, 3.34 mmol) was obtained from the obtained crude product and xylene (10 mL).

$^1$H-NMR (600 MHz, CDCl$_3$) δ(ppm): 1.27-1.41 (m, 5H), 1.42-1.50 (m, 6H), 1.59-1.70 (m, 7H), 2.31-2.40 (m, 5H), 5.12 (s, 4H), 7.31-7.38 (m, 10H).

(4) Synthesis of dibenzyl 6-(hydroxymethyl)undecanedioate

According to the method in Production Example 2-(1), the titled compound (1.14 g, 2.70 mmol) was obtained from the compound (1.47 g, 3.33 mmol) obtained in Example A-7-(3), borane-THF complex (1M, 6.7 mL, 6.7 mmol) and THF (38 mL).

$^1$H-NMR (600 MHz, CDCl$_3$) δ(ppm): 1.24-1.38 (m, 10H), 1.42-1.47 (m, 3H), 1.65 (quin, J=7.2 Hz, 4H), 1.71 (br s, 1H), 2.37 (t, J=7.5 Hz, 4H), 3.50 (br d, J=4.0 Hz, 2H), 5.12 (s, 4H), 7.31-7.39 (m, 7H).

(5) Synthesis of dibenzyl 6-{[(1-methylpyrrolidine-3-carbonyl)oxy)methyl]undecanedioate According to the method in Example A-4-(5), the titled compound (0.56 g, 1.05 mmol) was obtained from the compound (1.14 g, 2.68 mmol) obtained in Example A-7-(4), I-methylpyrrolidine-3-carboxylic acid hydrochloride (0.89 g, 5.36 mmol), EDC.HCl (1.13 g, 5.90 mmol), DIPEA (0.93 mL, 5.36 mmol), DMAP (0.066 g, 0.54 mmol) and methylene chloride (12 mL).

$^1$H-NMR (600 MHz, CDCl$_3$) δ(ppm): 1.26-1.38 (m, 9H), 1.59-1.70 ((m, 5H), 1.81 (br s, 1H), 2.06-2.14 (m, 2H), 2.34-2.40 (m, 7H), 2.47-2.55 (m, 1H), 2.58-2.68 (m, 2H), 2.84 (t, J=8.8 Hz, 1H), 3.04 (quin, J=7.7 Hz, 1H), 3.98 (d, J=5.9 Hz, 2H), 5.13 (s, 4H), 5.32 (s, 1H), 7.28 (s, 1H), 7.32-7.4 (m, 10H).

(6) Synthesis of bis(3-nonyldodecyl) 6-{[(1-methylpyrrolidine-3-carbonyl)oxy)methyl]undecanedioate According to Example A-1-(6), a crude product (0.24 g) of dicarboxylic acid was obtained from the compound (0.56 g, 1.03 mmol) obtained in Example A-7-(5), 10% palladium/carbon (0.55 g. containing 50% water) and ethyl acetate (27 mL).

The titled compound (0.029 g, 0.030 mmol) was obtained from the obtained carboxylic acid (0.055 g, 0.15 mmol), the compound (0.096 g, 0.31 mmol) obtained in Production Example 7-(3), EDC.HCl (0.118 g, 0.62 mmol), DIPEA (0.11 mL, 0.62 mmol), DMAP (4 mg, 0.031 mmol) and methylene chloride (0.7 mL).

$^1$H-NMR (600 MHz, CDCl$_3$) δ(ppm): 0.88 (t, J=7.0 Hz, 13H), 1.12-1.45 (m, 84H), 1.48-1.7 (m, 12H), 2.09 (q, J=7.3 Hz, 2H), 2.28 (t, J=7.6 Hz, 4H), 2.36 (s, 3H), 2.45-2.57 (m, 1H), 2.63 (br dd, J=8.9, 6.9 Hz, 2H), 2.83 (br t, J=8.6 Hz, 1H), 3.03 (quin, J=7.7 Hz, 1H), 3.94-4.02 (m, 2H), 4.07 (t, J=7.2 Hz, 4H).

Synthesis of Cationic Lipid (8)

Example A-8

Synthesis of bis(3-pentyloctyl) 9-{[(1-methylpyrrolidine-4-carbonyl)oxy]methyl}heptadecanedioate (Cationic Lipid 8)

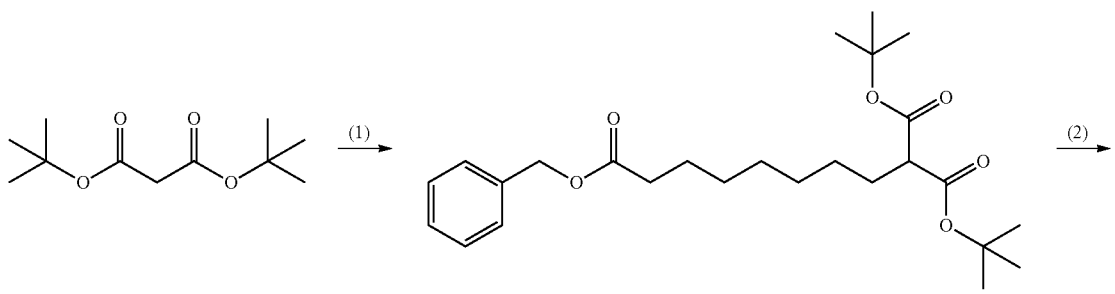

-continued
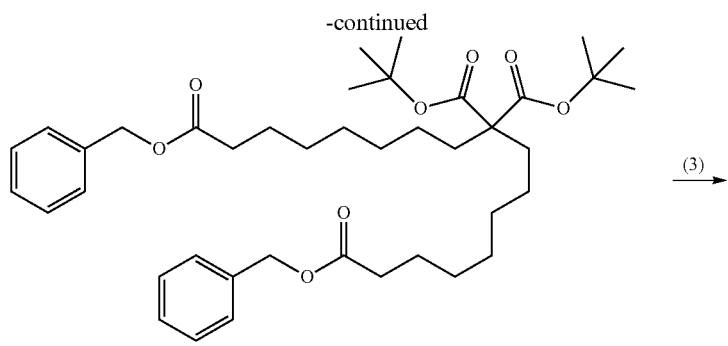
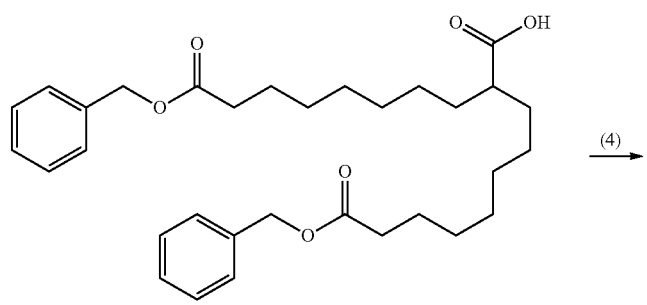
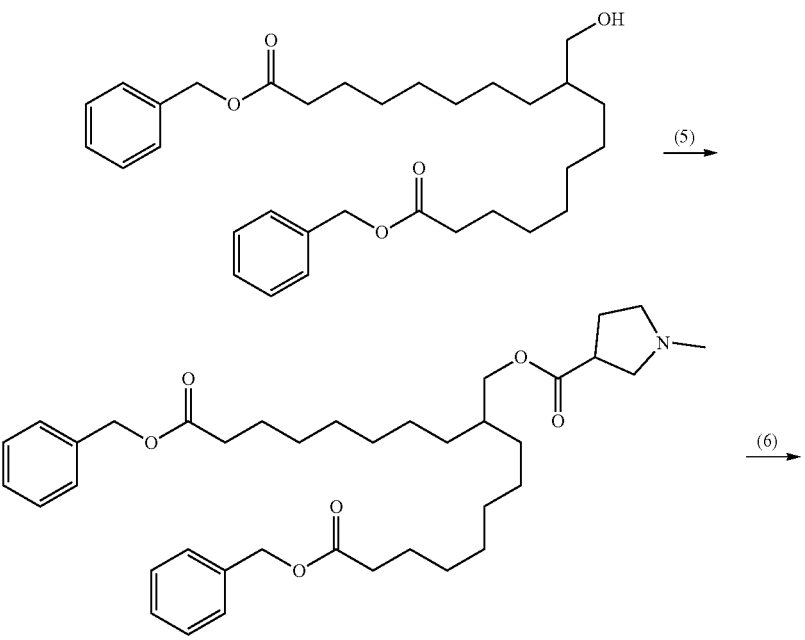
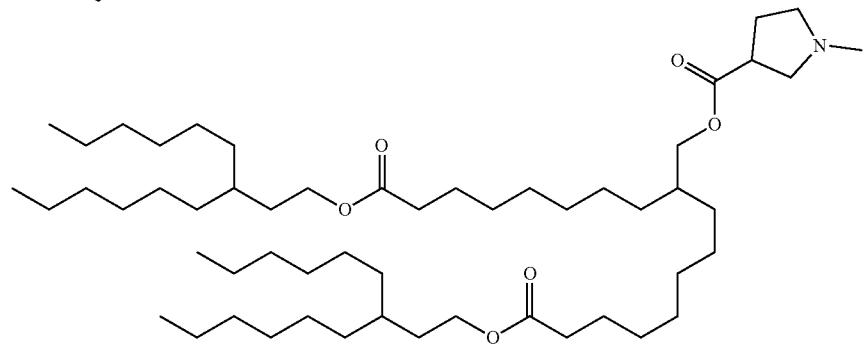

(1) Synthesis of 8-benzyl 1,1-di-tert-butyl octane-1,1,8-tricarboxylate

According to the method in Example A-5-(1), the titled compound (1.60 g, 3.57 mmol) was obtained from di-tert-butyl malonate (1.5 mL, 6.70 mmol), the compound (2.0 g, 6.39 mmol) obtained in Production Example 10, 60% sodium hydride (0.27 g, 6.70 mmol), sodium iodide (0.09 g, 0.64 mmol) and THF (60 mL).

$^1$H-NMR (600 MHz, CDCl$_3$) δ(ppm): 1.23-1.36 (m, 8H), 1.45 (s, 1H), 1.58-1.69 (m, 2H), 1.72-1.84 (m, 2H), 2.30-2.40 (m, 2H), 3.05-3.15 (m, 1H), 5.11 (s, 2H), 7.28-7.41 (m, 5H).

(2) Synthesis of 1,15-dibenzyl 8,8-di-tert-butyl pentadecane-1,8,8,15-tetracarboxylate According to the method in Example A-7-(2), the titled compound (1.4 g, 2.07 mmol) was obtained from the compound (1.6 g, 3.57 mmol) obtained in Example A-8-(1), the compound (1.17 g, 3.75 mmol) obtained in Production Example 10, sodium iodide (0.053 g, 0.36 mmol), 60% sodium hydride (0.16 g, 4.0 mmol) and THF (15 mL).

$^1$H-NMR (600 MHz, CDCl$_3$) δ(ppm): 1.03-1.17 (m, 4H), 1.23-1.36 (m, 12H), 1.43 (s, 18H), 1.56-1.68 (m, 4H), 1.70-1.8 (m, 4H), 2.29-2.38 (m, 4H), 5.11 (s, 4H), 7.27-7.41 (m, 10H).

(3) Synthesis of 10-(benzyloxy)-2-[8-(benzyloxy)-8-oxooctyl]-10-oxodecanoic acid According to the method in Example A-1-(3), a crude product (1.17 g) of dicarboxylic acid was obtained from the compound (1.40 g, 2.06 mmol) obtained in Example A-8-(2), methylene chloride (10 mL) and TFA (2.4 mL). The titled compound (0.83 g, 1.61 mmol) was obtained from the obtained crude product and xylene (25 mL).

$^1$H-NMR (600 MHz, CDCl$_3$) δ(ppm): 1.18-1.37 (m, 16H), 1.38-1.71 (m, 8H), 2.26-2.41 (m, 5H), 5.11 (s, 4H), 7.28-7.43 (m, 10H).

(4) Synthesis of dibenzyl 9-(hydroxymethyl)heptadecanedioate

According to the method in Production Example 2-(1), the titled compound (0.72 g, 1.43 mmol) was obtained from the compound (0.83 g, 1.59 mmol) obtained in Example A-8-(3), a borane-THF complex (1 M, 4.0 mL, 4.0 mmol) and THF (6.0 mL).

$^1$H-NMR (600 MHz, CDCl$_3$) δ(ppm): 1.12-1.51 (m, 22H), 1.56-1.72 (m, 4H), 2.29-2.41 (m, 4H), 3.47-3.58 (m, 2H), 5.11 (s, 4H), 7.28-7.44 (m, 10H).

(5) Synthesis of dibenzyl 9-{[(1-methylpyrrolidine-3-carbonyl)oxy)methyl]heptadecanedioate According to the method in Example A-4-(5), the titled compound (0.81 g, 1.30 mmol) was obtained from the compound (0.73 g, 1.43 mmol) obtained in Example A-8-(4), 1-methylpyrrolidine-3-carboxylic acid hydrochloride (0.36 g, 2.14 mmol), EDC.HCl (0.438 g, 2.29 mmol), DIPEA (0.37 mL, 2.14 mmol), DMAP (0.035 g, 0.29 mmol) and methylene chloride (6 mL).

$^1$H-NMR (600 MHz, CDCl$_3$) δ(ppm): 1.13-1.35 (m, 22H), 1.58-1.69 (m, 5H), 2.04-2.14 (m, 2H), 2.29-2.39 (m, 7H), 2.43-2.54 (m, 1H), 2.57-2.67 (m, 2H), 2.84 (t, J=8.8H, 1H), 2.99-3.08 (m, 1H), 3.97 (d, J=5.7 Hz, 2H), 5.11 (s, 4H), 7.29-7.40 (m, 9H).

(6) Synthesis of bis(3-hexylnonyl) 9-{[(1-methylpyrrolidine-3-carbonyl)oxy)methyl]heptadecanedioate According to Example A-1-(6), a crude product (0.66 g) of dicarboxylic acid was obtained from the compound (0.81 g, 1.30 mmol) obtained in Example A-8-(5), 10% palladium/carbon (0.028 g. containing 50% water) and ethyl acetate (15 mL).

The titled compound (0.077 g, 0.090 mmol) was obtained from the obtained dicarboxylic acid (0.10 g, 0.23 mmol), the compound (0.124 g, 0.54 mmol) obtained in Production Example 9-(2). EDC.HCl (0.113 g, 0.59 mmol), DIPEA (0.10 mL, 0.59 mmol). DMAP (6 mg, 0.050 mmol) and methylene chloride (5 mL).

$^1$H-NMR (600 MHz, CDCl$_3$) δ(ppm): 0.88 (t, J=7.0 Hz, 13H), 1.18-1.35 (m, 64H), 1.37-1.42 (m, 2H), 1.52-1.66 (m, 9H), 2.06-2.13 (m, 2H), 2.25-2.32 (m, 4H), 2.36 (s, 3H), 2.45-2.53 (m, 1H), 2.59-2.66 (m, 2H), 2.85 (t, J=8.8 Hz, 1H), 3.00-3.08 (m, 1H), 3.98 (d, J=5.9 Hz, 2H), 4.08 (t, J=7.1 Hz, 4H).

Synthesis of Cationic Lipid (9)

Example A-9

Synthesis of bis(3-pentyloctyl) 9-{[(1-methylpyrrolidine-3-carbonyl)oxy]methyl}heptadecanedioate (Cationic Lipid 9)

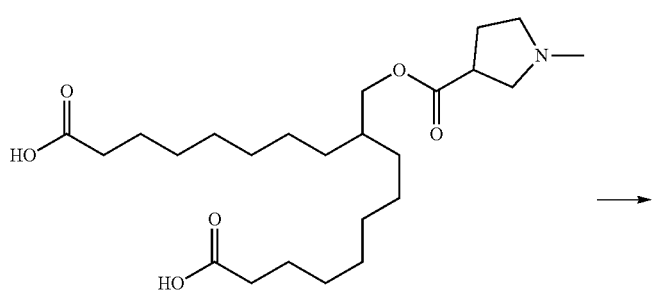

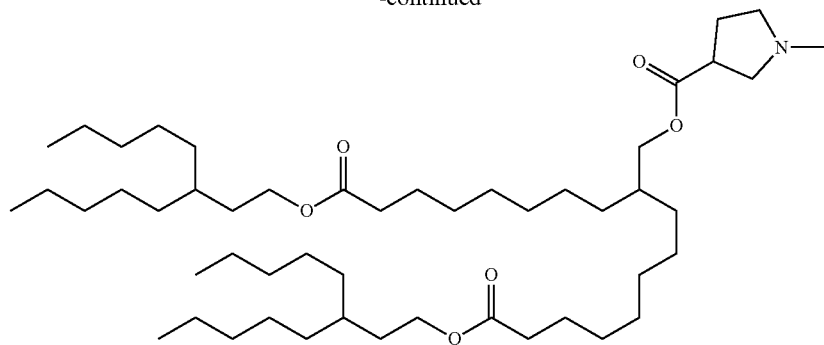

According to Example A-1-(6), the titled compound (0.089 g, 0.11 mmol) was obtained from the dicarboxylic acid (0.10 g, 0.23 mmol) obtained in Example A-8-(6), 3-pentyloctan-1-ol (CAS 1443519-63-8) (0.11 g, 0.54 mmol), EDC.HCl (0.11 g, 0.59 mmol), DIPEA (0.10 mL, 0.59 mmol), DMAP (6 mg, 0.050 mmol) and methylene chloride (5 mL).

$^1$H-NMR (600 MHz, CDCl$_3$) δ(ppm): 0.88 (t, J=7.2 Hz, 13H), 1.17-1.34 (m, 56H), 1.37-1.43 (m, 2H), 1.53-1.69 (m, 10H), 2.06-2.14 (m, 2H), 2.28 (t, J=7.5 Hz, 4H), 2.36 (s, 3H), 2.45-2.53 (m, 1H), 2.58-2.66 (m, 2H), 2.84 (t, J=8.9 Hz, 1H), 3.00-3.08 (m, 1H), 3.98 (d, J=5.7 Hz, 2H), 4.08 (t, J=7.1 Hz, 4H).

Synthesis of Cationic Lipid (10)

Comparative Example A'-1

Synthesis of 2-{9-oxo-9-[(3-pentyloctyl)oxy] nonyl}dodecyl 1-methylazepane-4-carboxylate (Cationic Lipid 10)

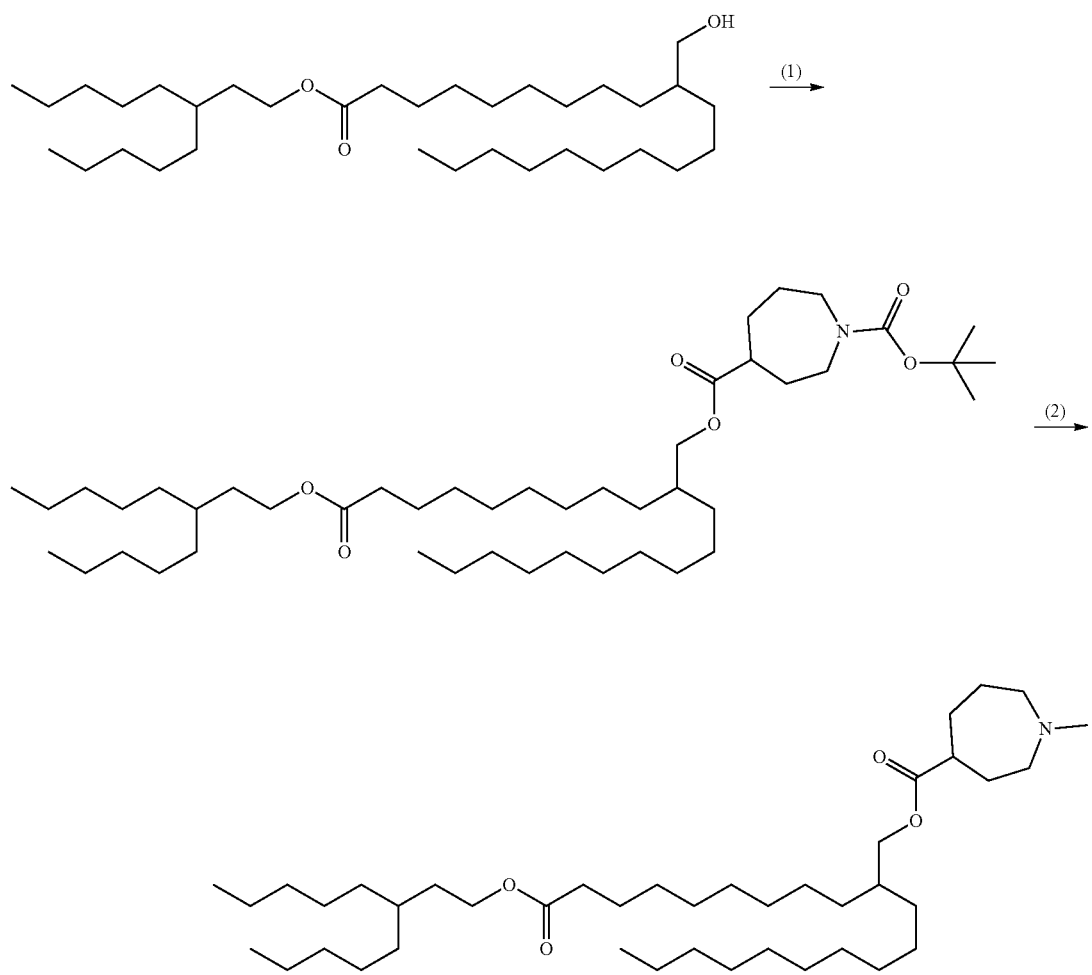

(1) Synthesis of 1-tert-butyl 4-(2-{9-oxo-9-[(3-pentyloctyl)oxy]nonyl}dodecyl) azepane-1,4-dicarboxylate According to the method in Example A-1-(8), the titled compound (81 mg, 0.11 mmol) was obtained from the compound (60 mg, 0.11 mmol) obtained in Example A-1-(7), 1-(tert-butoxycarbonyl)azepane-4-carboxylic acid (56 mg, 0.23 mmol), EDC.HCl (48 mg, 0.25 mmol), DIPEA (0.039 mL, 0.23 mmol), DMAP (2.8 mg, 0.023 mmol) and methylene chloride (0.80 mL).

(2) Synthesis of 2-{9-oxo-9-[(3-pentyloctyl)oxy]nonyl}dodecyl 1-methylazepane-4-carboxylate According to the method in Example A-2-(2), the titled compound (51 mg, 0.077 mmol) was obtained from the compound (81 mg, 0.11 mmol) obtained in Comparative Example A'-1(1), TFA (1.1 mL), THF (1 mL), a formaldehyde solution (37%, 0.080 mL, 1.1 mmol), sodium sulphate (460 mg, 3.23 mmol) and sodium tri(acetoxy)borohydride (69 mg, 0.32 mmol).

$^1$H-NMR (400 MHz, CDCl$_3$) δ(ppm): 0.88 (t, J=7.0 Hz, 9H), 1.14-1.49 (m, 49H), 1.51-1.71 (s, 4H), 1.73-2.10 (m, 5H), 2.23-2.31 (m, 2H), 2.34 (s, 3H), 2.45-2.76 (m, 5H), 3.92-3.98 (m, 2H), 4.03-4.12 (m, 2H).

Synthesis of Cationic Lipid (11)

Comparative Example A'-2

Synthesis of 2-butyloctyl 9-bromononanoate (Cationic Lipid 11)

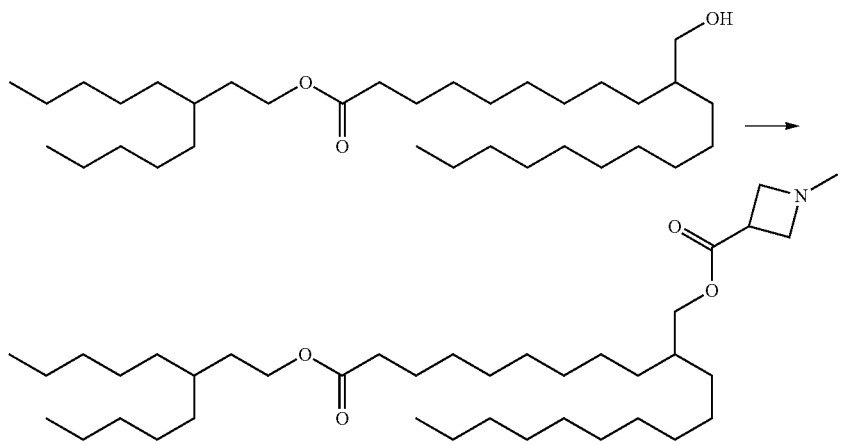

According to the method in Example A-1-(8), the titled compound (30 mg, 0.048 mmol) was obtained from the compound (50 mg, 0.095 mmol) obtained in Example A-1-(7), 1-methyl-3-azetidinecarboxylic acid (22 mg, 0.19 mmol), EDC.HCl (40 mg, 0.21 mmol), DIPEA (0.033 mL, 0.19 mmol). DMAP (2.3 mg, 0.019 mmol) and methylene chloride (0.80 mL).

$^1$H-NMR (400 MHz, CDCl$_3$) δ(ppm): 0.88 (t, J=6.9 Hz, 9H), 1.14-1.47 (m, 44H), 1.61 (s, 8H), 2.30 (s, 5H), 3.26 (s, 3H), 3.46-3.64 (m, 2H), 3.99 (d, J=5.9 Hz, 2H), 4.08 (t, J=7.1 Hz, 2H).

The synthesized cationic lipids 1 to 11 are indicated in Table A below.

TABLE A

| Synthesized cationic lipids 1 to 11 | |
|---|---|
| | Structure |
| Cationic lipid 1: (3S)-2-{9-oxo-9-[(3-pentyloctyl)oxy]nonyl} dodecyl 1-methylpyrrolidine-3-carboxylate | |

(A1)

TABLE A-continued

Synthesized cationic lipids 1 to 11

Structure

Cationic lipid 2:
(3R)-2-{9-oxo-9-[(3-pentyloctyl)oxy]nonyl}dodecyl 1-methylpyrrolidine-3-carboxylate

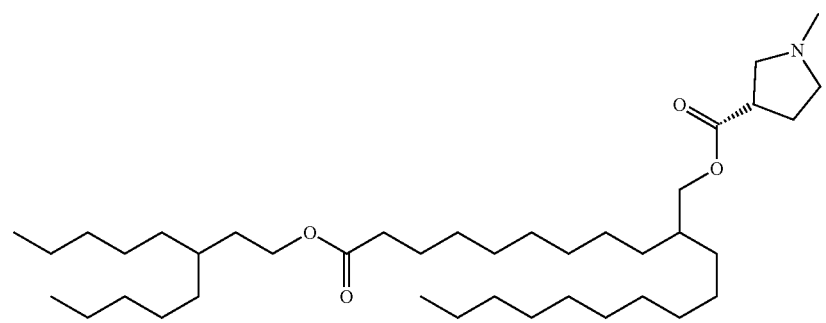

(A2)

Cationic lipid 3:
2-{9-oxo-9-[(3-pentyloctyl)oxy]nonyl}dodecyl 1-methylpyrrolidine-3-carboxylate

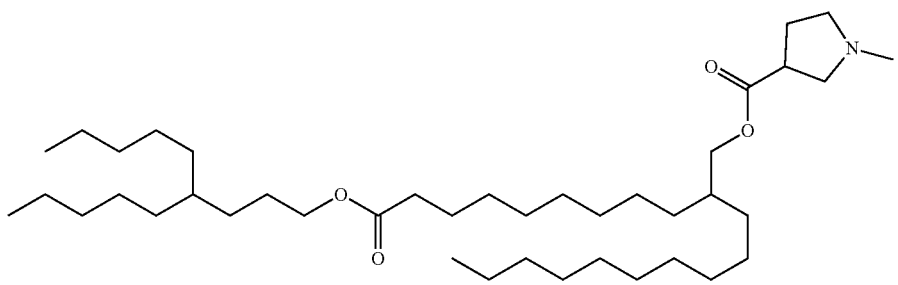

(A3)

Cationic lipid 4:
2-nonyl-1 1-oxo-1 1-[(3-pentyloctyl)oxy]undecyl 1-methylpyrrolidine-3-carboxylate

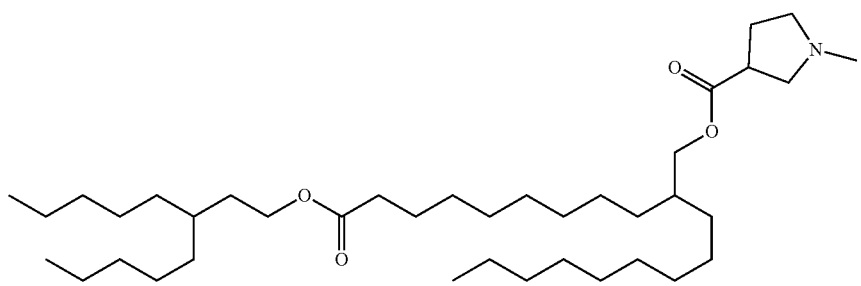

(A4)

Cationic lipid 5:
2-{6-[(3-octylundecyl)oxy]-6-oxohexyl}dodecyl 1-methylpyrrolidine-3-carboxylate

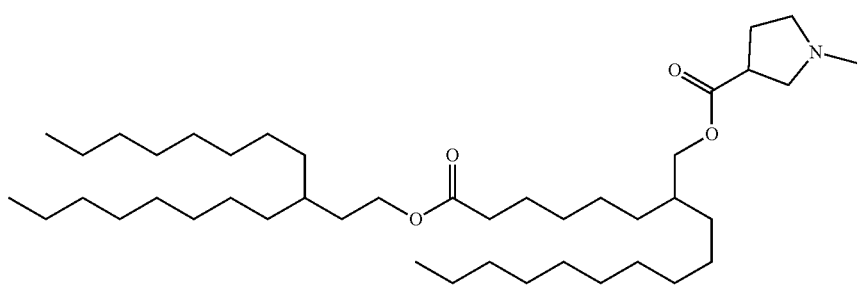

(A5)

TABLE A-continued
Synthesized cationic lipids 1 to 11
Structure
Cationic lipid 6:
2-{4-[(4-nonyltridecyl)
oxy]-4-oxobutyl}dodecyl
1-methylpyrrolidine-3-
carboxylate
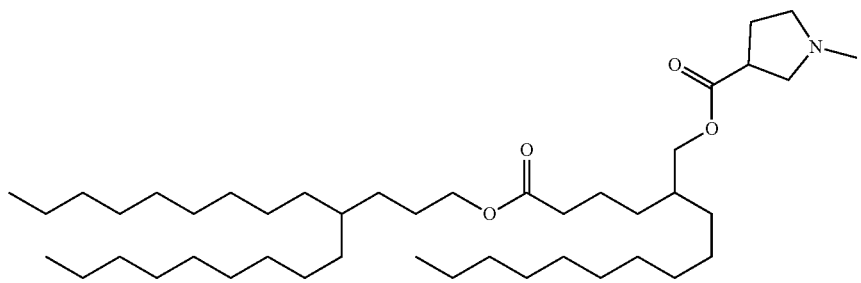
(A6)
Cationic lipid 7:
bis(3-nonyldodecyl)6-
{[(1-methylpyrrolidine-
3-carbonyl)oxy]methyl}
undecanedioate
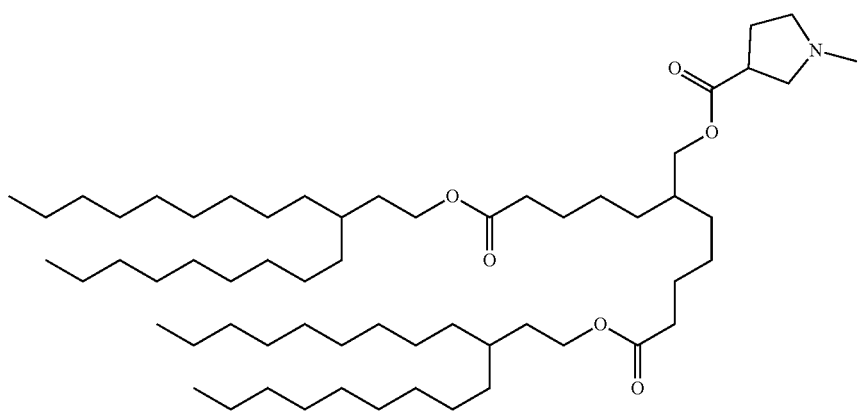
(A7)
Cationic lipid 8:
bis(3-pentyloctyl)9-{[(1-
methylpyrrolidine-4-
carbonyl)oxy]methyl}
heptadecanedioate
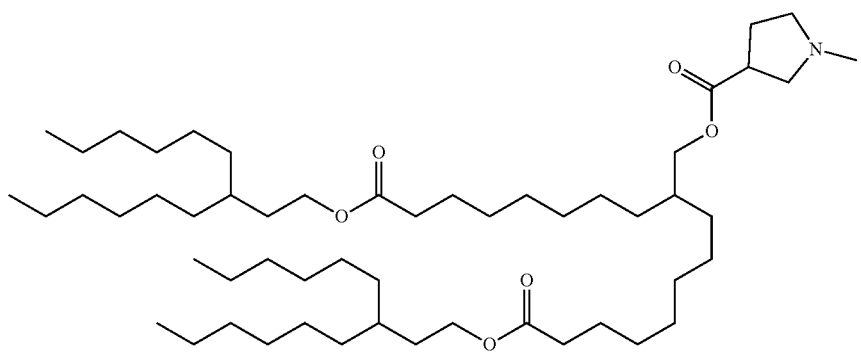
(A8)

TABLE A-continued

Synthesized cationic lipids 1 to 11

Structure

Cationic lipid 9:
bis(3-pentyloctyl) 9-{[(1-methylpyrrolidine-3-carbonyl)oxy]methyl} heptadecanedioate

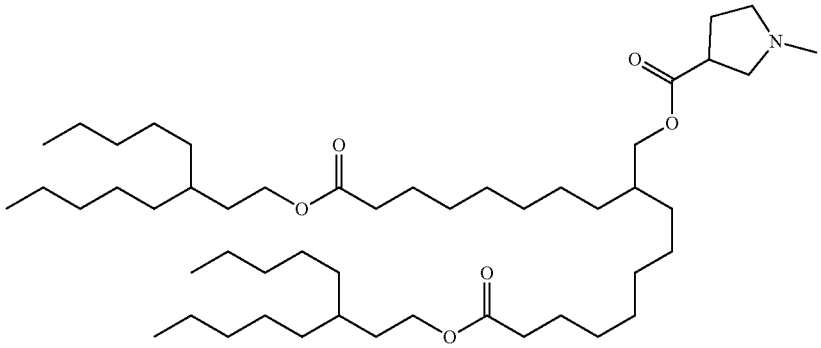

(A9)

Cationic lipid 10:
2-{9-oxo-9-[(3-pentyloctyl)oxy]nonyl} dodecyl 1-methylazepane-4-carboxylate

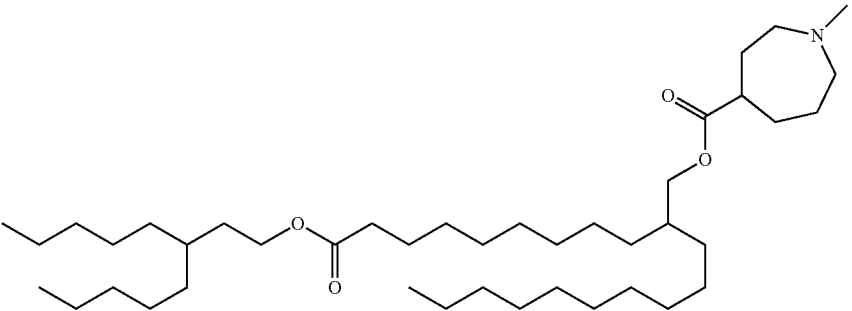

(A'1)

Cationic lipid
2-butyloctyl 9-bromononanoate

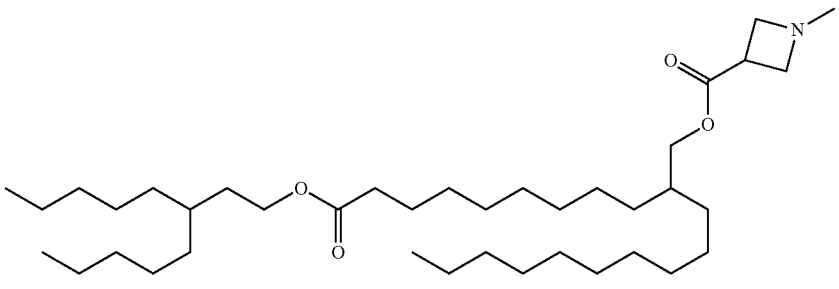

(A'2)

B. Preparation and Analysis of Compositions

Preparation of Compositions (I)

Example B-1

A composition was prepared with cationic lipid 1 of Example A-1. As the nucleic acid, annealed siRNA (GeneDesign Inc., hereinafter also referred to as "Factor VII siRNA") that silences expression of the Factor VII (blood coagulation factor VII) gene and consists of a sense strand having a base sequence: 5'-GGAfUfCAfUfCUfCAAGfUf-CfUfUAfCT*T-3' (T: DNA, fU, fC=2'-Fluoro RNA, *=Phosphorothioate linkage) (SEQ ID NO: 1) and an antisense strand having a base sequence: 5'-GfUAAGAfCfUfUGAGAfUGAfUfCfCT*T-3' (T: DNA, fU, fC=2'-Fluoro RNA, *=Phosphorothioate linkage) (SEQ ID NO: 2) was used.

Factor VII siRNA was dissolved in 25 mM sodium acetate aqueous solution (pH 4.0) at 80 µg/mL to obtain a diluted siRNA solution. Cationic lipid 1, DSPC (Nippon Fine Chemical Co., Ltd.), Cholesterol (Nippon Fine Chemical Co., Ltd.), MPEG2000-DMG (NOF Corporation, methoxy (polyethylene glycol, molecular weight=2000)-dimyristylglycerol) were dissolved in ethanol at a ratio of 60/8.5/30/1.5 (molar ratio) so that the total lipid concentration was set to 7.2 mM, and then a lipid solution was obtained. The diluted siRNA solution and the lipid solution were fed and mixed at flow rates of 3 mL/min and 1 mL/min. respectively, to obtain a lipid complex aqueous solution. The obtained lipid complex aqueous solution was subjected to dialysis using a dialysis membrane (product name "Float-A-Lyzer G2", SPECTRUM, Inc., 100K MWCO) to replace the external solution with phosphate buffer (PBS, pH 7.4). After the dialysis, concentration and filter sterilization were performed, thereby obtaining a liquid composition of Example B-1.

Example B-2

A composition of Example B-2 was obtained in the same manner as Example B-1 except that as the cationic lipid, cationic lipid 2 of Example A-2 was used instead of cationic lipid 1.

Comparative Example B'-1

A composition of Comparative Example B'-1 was obtained in the same manner as Example B-1 except that as the cationic lipid, cationic lipid 10 of Comparative Example A'-1 was used instead of cationic lipid 1.

Comparative Example B'-2

A composition of Comparative Example B'-2 was obtained in the same manner as Example B-1 except that as the cationic lipid, cationic lipid 11 of Comparative Example A'-2 was used instead of cationic lipid 1.

<Analysis of Compositions (1)>

In the compositions of Example B-1, Example B-2, Comparative Example B'-1 and Comparative Example B'-2, the encapsulation rate of siRNA into lipid complexes was measured.

Specifically, the siRNA concentration (A) measured with Quant-iT RiboGreen RNA Reagent (Invitrogen) after diluting a composition with RNase Free Water was set as the concentration of siRNA present in the external solution of the lipid complex. The siRNA concentration (B) measured after diluting the composition with 1% Triton X-100 was set as the total siRNA concentration in the composition. Next, according to formula (F1) below, the encapsulation rate of the nucleic acid was calculated.

Encapsulation rate (%)=100−(A/B)×100    (F1)

The average particle diameter of lipid complexes was measured using a particle diameter analyser (product name "Zetasizer Nano ZS", produced by Malvern Panalytical Ltd.).

Table 1 shows the encapsulation rate of siRNA and the average particle diameter (Z-average) and the polydispersion index of the lipid complexes.

TABLE 1

| Composition | Cationic lipid | Encapsulation rate (%) | Average particle diameter (nm) | Polydispersion index |
|---|---|---|---|---|
| Example B-1 | 1 | 94 | 90 | 0.14 |
| Example B-2 | 2 | 96 | 91 | 0.11 |

TABLE 1-continued

| Composition | Cationic lipid | Encapsulation rate (%) | Average particle diameter (nm) | Polydispersion index |
|---|---|---|---|---|
| Comparative Example B'-1 | 10 | 99 | 95 | 0.13 |
| Comparative Example B'-2 | 11 | 95 | 105 | 0.13 |

It is confirmed that the compositions of Example B-1 and Example B-2 exhibit high encapsulation rates of siRNA, equivalent to those of the compositions of Comparative Example B'-1 and Comparative Example B'-2.

Preparation of Compositions (2)

Example B-3

A composition of Example B-3 was obtained in the same manner as Example B-1 in preparation of composition (1), except that as the cationic lipid, cationic lipid 3 of Example A-3 was used instead of cationic lipid 1.

Example B-4

A composition of Example B-4 was obtained in the same manner as Example B-3 except that as the cationic lipid, cationic lipid 4 of Example A-4 was used instead of cationic lipid 3.

Example B-5

A composition of Example B-5 was obtained in the same manner as Example B-3 except that as the cationic lipid, cationic lipid 5 of Example A-5 was used instead of cationic lipid 3.

Example B-6

A composition of Example B-6 was obtained in the same manner as Example B-3 except that as the cationic lipid, cationic lipid 6 of Example A-6 was used instead of cationic lipid 3.

Example B-7

A composition of Example B-7 was obtained in the same manner as Example B-3 except that as the cationic lipid, cationic lipid 7 of Example A-7 was used instead of cationic lipid 3.

Example B-8

A composition of Example B-8 was obtained in the same manner as Example B-3 except that as the cationic lipid, cationic lipid 8 of Example A-8 was used instead of cationic lipid 3.

Example B-9

A composition of Example B-9 was obtained in the same manner as Example B-3 except that as the cationic lipid, cationic lipid 9 of Example A-9 was used instead of cationic lipid 3.

Example B-10

A composition of Example 8-10 was obtained in the same manner as Example B-3 except that as the cationic lipid, cationic lipid 1 of Example A-1 was used instead of cationic lipid 3.

Comparative Example B'-3

A composition of Comparative Example B'-3 was obtained in the same manner as Example B-3 except that as the cationic lipid, di ((Z)-nonan-2-en-1-yl)9-((4-(dimethylamino)butanoyl)oxy)heptadecanedioate (hereinafter also referred to as "ALN-319") represented by formula (i) below disclosed in Patent Literature 2 that was synthesized according to the method disclosed in Patent Literature 2 was used instead of cationic lipid 3.

TABLE 3

| Composition | Cationic lipid | Pre-storage average particle diameter (nm) | Post-storage average particle diameter (nm) | Change in average particle diameter (%) |
|---|---|---|---|---|
| Example B-3 | 3 | 102 | 107 | 105 |
| Example B-4 | 4 | 101 | 108 | 106 |
| Example B-5 | 5 | 86 | 90 | 104 |
| Example B-6 | 6 | 89 | 92 | 104 |
| Example B-7 | 7 | 106 | 115 | 109 |
| Example B-8 | 8 | 95 | 102 | 107 |
| Example B-9 | 9 | 85 | 91 | 107 |
| Comparative Example B'-3 | ALN-319 | 95 | 121 | 127 |

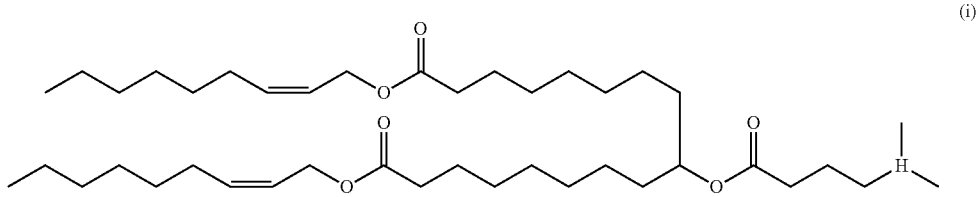

(i)

<Analysis of Compositions (2)>

In the same manner as in analysis of compositions (1), the encapsulation rate of siRNA in lipid complexes and the average particle diameter of lipid complexes were measured for the compositions of Example B-3 to Example B-10 and Comparative Example B'-3. Table 2 shows the encapsulation rate of siRNA and the average particle diameter (Z-average) and the polydispersion index of lipid complexes.

TABLE 2

| Composition | Cationic lipid | Encapsulation rate (%) | Average particle diameter (nm) | Polydispersion index |
|---|---|---|---|---|
| Example B-3 | 3 | 93 | 102 | 0.10 |
| Example B-4 | 4 | 89 | 101 | 0.16 |
| Example B-5 | 5 | 96 | 86 | 0.12 |
| Example B-6 | 6 | 97 | 89 | 0.15 |
| Example B-7 | 7 | 95 | 106 | 0.13 |
| Example B-8 | 8 | 93 | 95 | 0.14 |
| Example B-9 | 9 | 94 | 85 | 0.09 |
| Example B-10 | 1 | 94 | 90 | 0.14 |
| Comparative Example B'-3 | ALN-319 | 84 | 95 | 0.08 |

<Analysis of Compositions (4)>

The compositions of Example B-3 to Example B-9 and Comparative Example B'-3 were further stored in sealed vials at 4° C. for 1.5 months and the average particle diameter (post-storage average particle diameter) of lipid complexes was measured in the same manner as in analysis of compositions (1). Table 3 shows the change in the average particle diameter (Z-average) of lipid complexes. In the table, the change (%) in the average particle diameter was calculated by post-storage average particle diameter/pre-storage average particle diameter×100.

It was demonstrated that the compositions of Example B-3 to Example B-9 had almost no change in average particle diameters after a storage over 1.5 months and were physically more stable than the composition of Comparative Example B'-3. This result indicates that the cationic lipid of the present invention can minimize an increase in particle diameter of lipid complex after a storage over a certain period of time.

C. Test Examples

Test Example 1

The compositions of Example B-1, Example B-2. Comparative Example B'-1 and Comparative Example B'-2 were diluted with PBS so that the Factor VII siRNA concentration encapsulated in lipid complexes was 3 or 30 μg/mL. The compositions were administered to ICR mice (n=3) via the tail vein at a dosage of 10 mL/kg, and the blood was collected under anaesthesia 1 day after administration. The plasma was separated from the blood by centrifugation and the Factor VII protein concentration in the plasma was assayed using a commercially available kit (product name "BIOPHEN FVII", HYPHEN BioMed). As a negative control, the same treatment was carried out in a group to which PBS was administered.

When setting the Factor VII protein concentration of the group to which PBS was administered (negative control) to 100%, the Factor VII protein concentration of the groups to which the compositions were administered were calculated as a relative value. The results are show in FIG. 1 and Table 4.

TABLE 4

| siRNA dose (mg/kg) | Composition | Cationic lipid | Factor VII protein concentration (relative value) |
|---|---|---|---|
| 0.03 | Example B-1 | 1 | 47% |
|  | Example B-2 | 2 | 40% |
|  | Comparative Example B'-1 | 10 | 76% |
|  | Comparative Example B'-2 | 11 | 83% |
| 0.3 | Example B-1 | 1 | 3% |
|  | Example B-2 | 2 | 2% |
|  | Comparative Example B'-1 | 10 | 21% |
|  | Comparative Example B'-2 | 11 | 50% |

It is confirmed that the compositions of Example B-1 and Example B-2 have a higher inhibitory effect on Factor VII protein expression than the compositions of Comparative Example B'-1 and Comparative Example B'-2. This result indicates that the compositions of Examples effectively release nucleic acids into the cytoplasm.

Test Example 2

Figure 2:
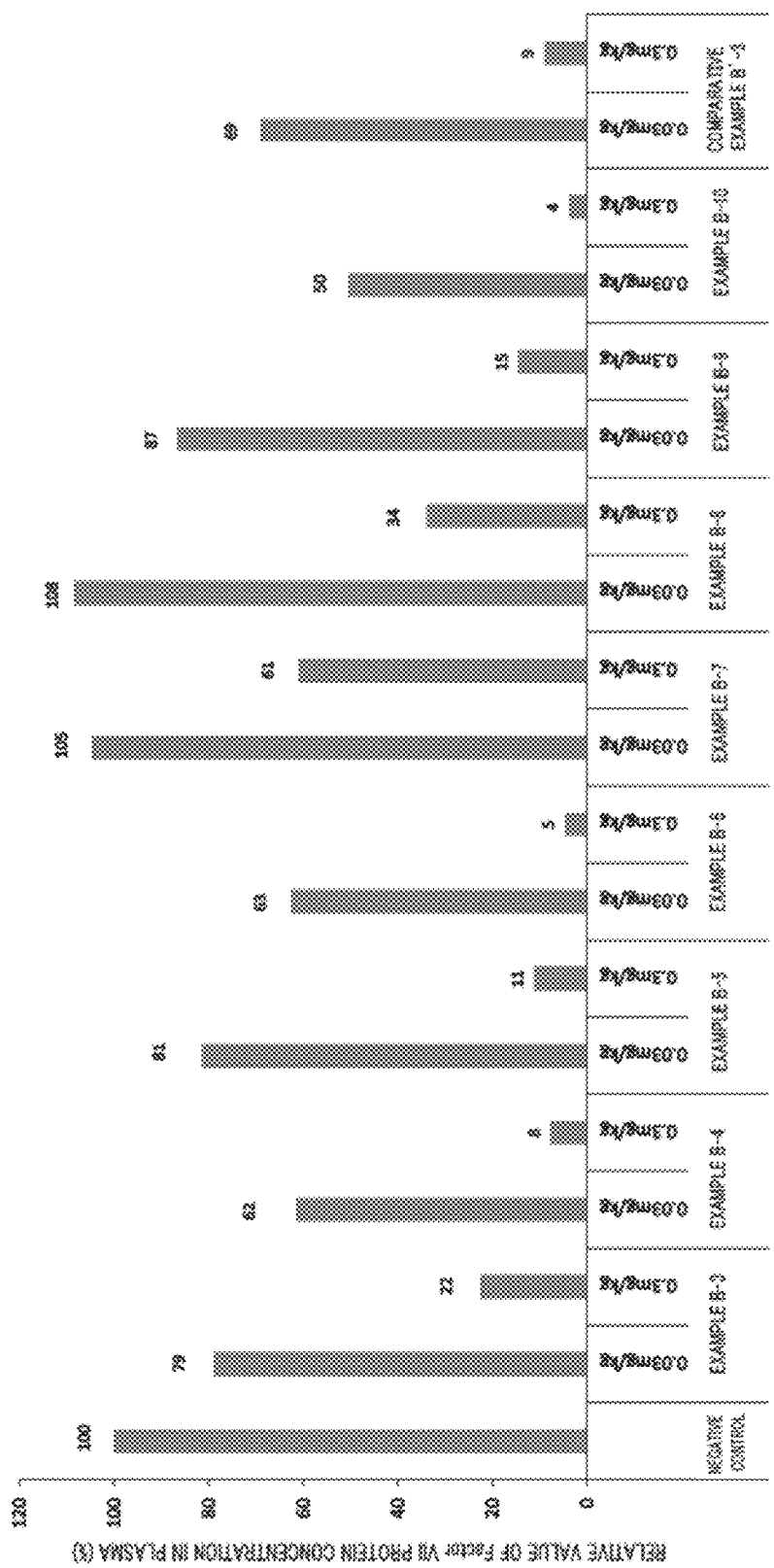
FIG. 2 is a graph illustrating the result of Test Example 2.

In the same manner as in Test Example 1, the compositions of Example B-3 to Example B-10 and Comparative Example B'-3 were administered to ICR mice (n=3) and the relative value of the Factor VII protein concentration in the plasma 1 day after administration was calculated by setting the Factor VII protein concentration in the group to which PBS was administered (negative control) as 100%. The results are shown in FIG. 2 and Table 5.

TABLE 5

| siRNA dose (mg/kg) | Composition | Cationic lipid | Factor VII protein concentration (relative value) |
|---|---|---|---|
| 0.03 | Example B-3 | 3 | 79% |
|  | Example B-4 | 4 | 62% |
|  | Example B-5 | 5 | 81% |
|  | Example B-6 | 6 | 63% |
|  | Example B-7 | 7 | 105% |
|  | Example B-8 | 8 | 108% |
|  | Example B-9 | 9 | 87% |
|  | Example B-10 | 1 | 50% |
|  | Comparative Example B'-3 | ALN-319 | 69% |
| 0.3 | Example B-3 | 3 | 22% |
|  | Example B-4 | 4 | 8% |
|  | Example B-5 | 5 | 11% |
|  | Example B-6 | 6 | 5% |
|  | Example B-7 | 7 | 61% |
|  | Example B-8 | 8 | 34% |
|  | Example B-9 | 9 | 15% |
|  | Example B-10 | 1 | 4% |
|  | Comparative Example B'-3 | ALN-319 | 9% |

The results in Test Examples 1 and 2 demonstrate that the compositions of Examples can release nucleic acids into the cytoplasm.

The results in Test Examples 1 and 2 also indicate that the compositions of Example B-1, Example B-2, Example B-3, Example B-4, Example B-5, Example B-6, Example B-8, Example B-9 and Example B-10 (cationic lipids 1, 2, 3, 4, 5, 6, 8 and 9) have an excellent inhibitory effect of Factor VII protein expression (particularly when the siRNA dose is relatively high). It is confirmed from the results that the compositions effectively release nucleic acids into the cytoplasm.

The results in Test Examples 1 and 2 also indicate that the compositions Example B-1, Example B-2, Example B-3, Example B-4, Example B-5, Example B-6, Example B-9 and Example B-10 (cationic lipids 1, 2, 3, 4, 5, 6 and 9) inhibited Factor VII protein expression even when the siRNA dose was low. It is confirmed from the results that the compositions effectively release nucleic acids into the cytoplasm.

Particularly, the compositions of Example B-1, Example B-2, Example B-4, Example B-6 and Example B-10 (cationic lipids 1, 2, 4 and 6) have a higher inhibitory effect of Factor VII protein expression than the composition of Comparative Example B'-3. It is suggested that the compositions can more effectively release nucleic acids into the cytoplasm.

From the above results, according to the cationic lipid of an embodiment of the present invention, it is possible to release effectively nucleic acids into the cytoplasm. In addition, according to the cationic lipid of an embodiment of the present invention, it is possible to minimize an increase in the particle diameter of lipid complexes after a storage over a certain period of time.

INDUSTRIAL APPLICABILITY

According to the present invention, it is possible to provide a cationic lipid that can release nucleic acids into the cytoplasm.

The invention claimed is:

1. A compound represented by formula (1) or a pharmaceutically acceptable salt thereof:

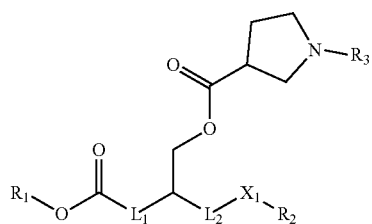

(1)

wherein $L_1$ and $L_2$ independently represent an alkylene group having 3 to 10 carbon atoms; $R_1$ and $R_2$ independently represent an alkyl group having 4 to 24 carbon atoms or an alkenyl group having 4 to 24 carbon atoms; $R_3$ represents an alkyl group having 1 to 3 carbon atoms; and $X_1$ represents a single bond or CO—O—.

2. The compound according to claim 1 selected from the group consisting of compounds represented by formulae (A1) to (A9) below, or a pharmaceutically acceptable salt thereof

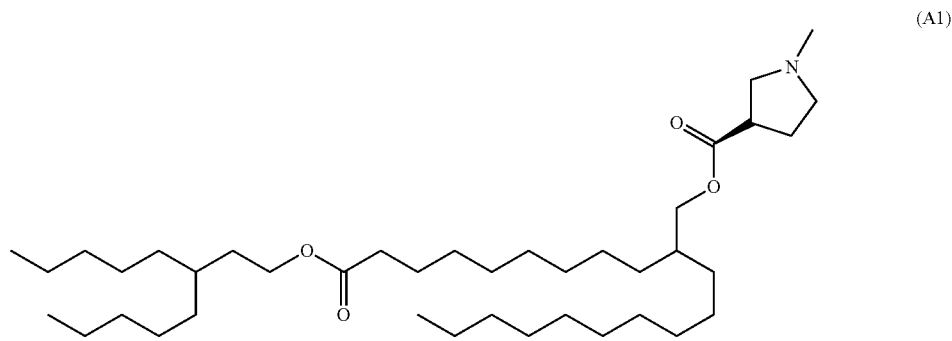

(A1)

-continued
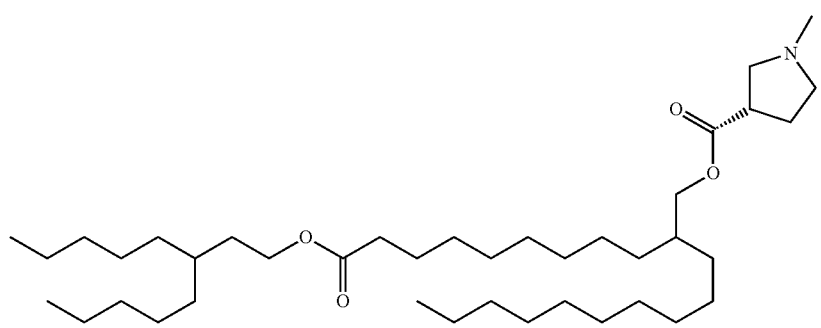
(A2)
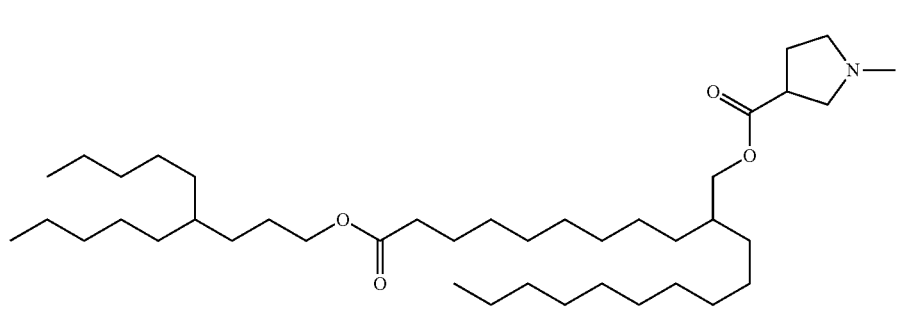
(A3)
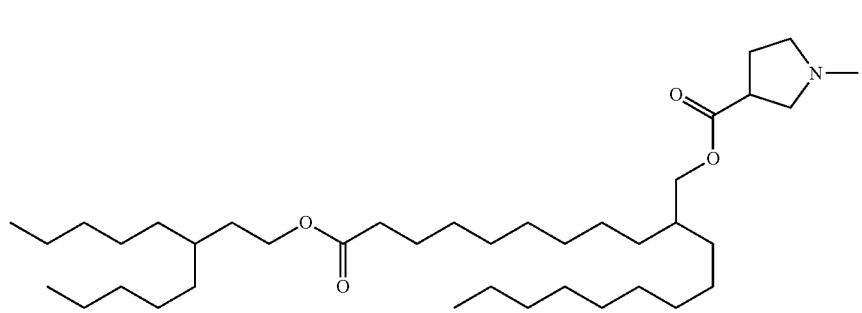
(A4)
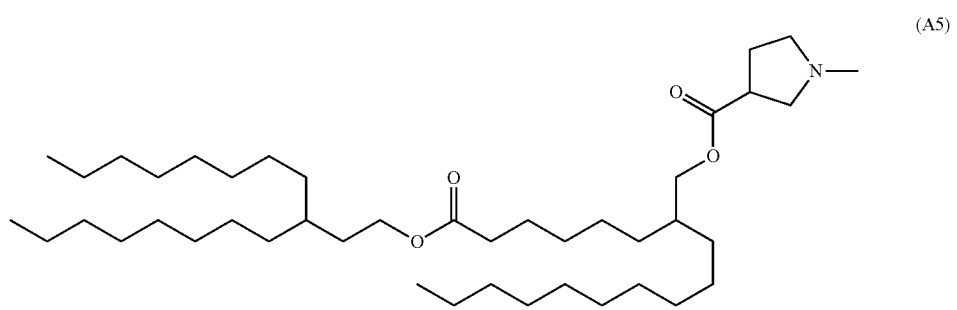
(A5)
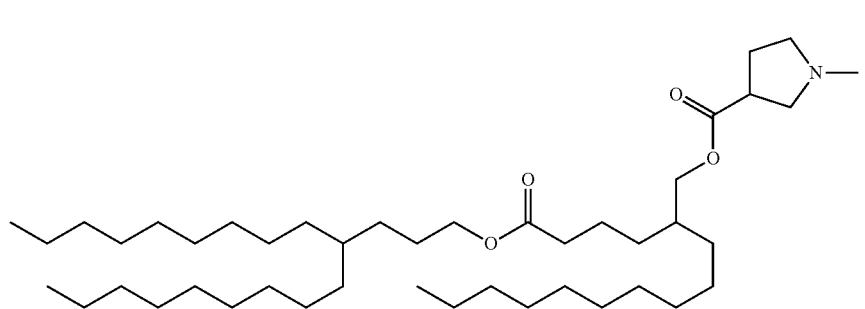
(A6)

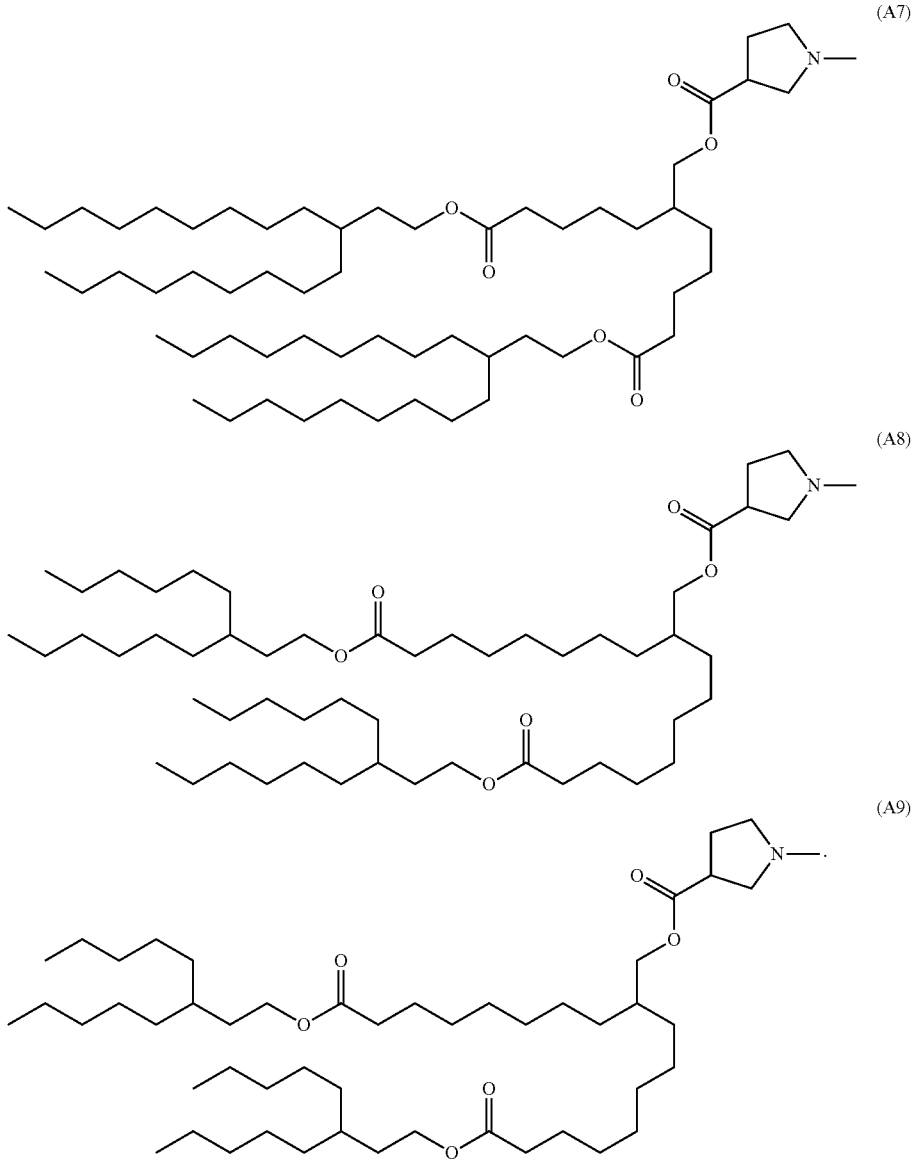
3. The compound according to claim 1 represented by formula (A1) below, or a pharmaceutically acceptable salt thereof
4. The compound according to claim 1 represented by formula (A2) below, or a pharmaceutically acceptable salt thereof
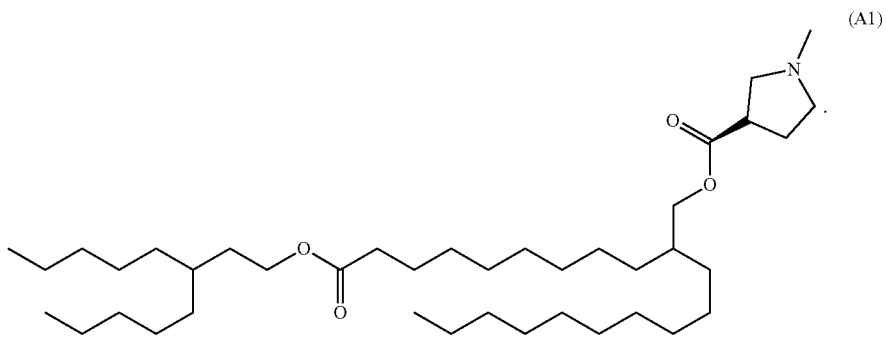

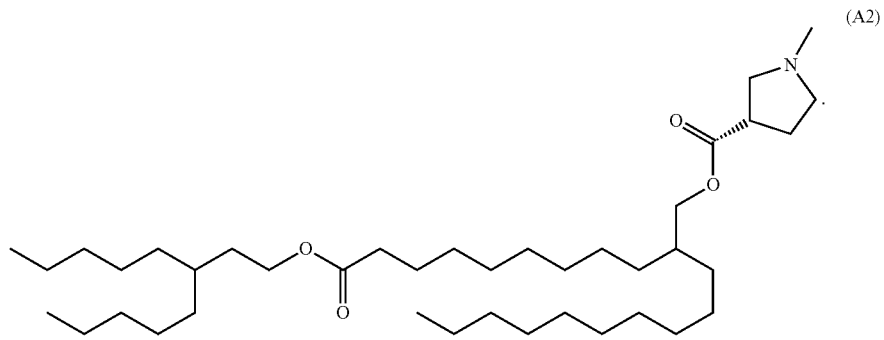
(A2)
5. The compound according to claim 1 represented by formula (A3) below, or a pharmaceutically acceptable salt thereof
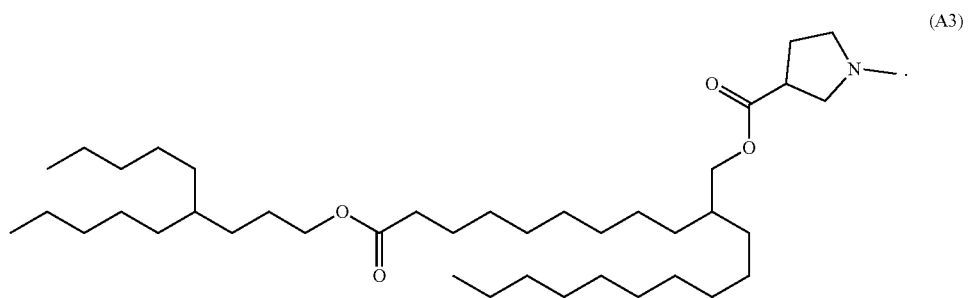 [SMILES: CCCCCCCCCCC(CCCCCCCCC(=O)OCCCC(CCCCC)CCCCC)COC(=O)C1CCN(C)C1]
(A3)
6. The compound according to claim 1 represented by formula (A4) below, or a pharmaceutically acceptable salt thereof
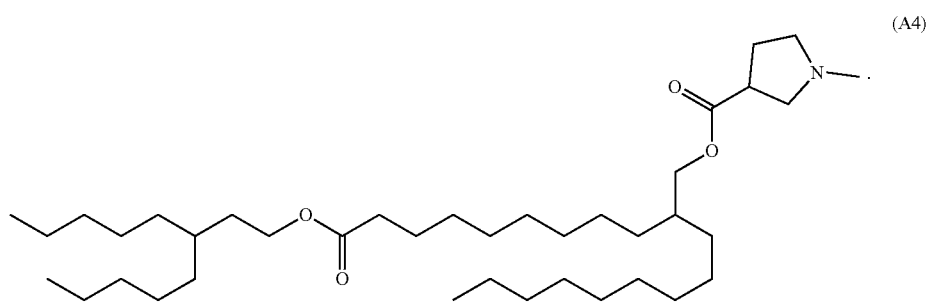 [SMILES: CCCCCCCCCC(CCCCCCCCC(=O)OCCC(CCCCC)CCCCC)COC(=O)C1CCN(C)C1]
(A4)
7. The compound according to claim 1 represented by formula (A5) below, or a pharmaceutically acceptable salt thereof
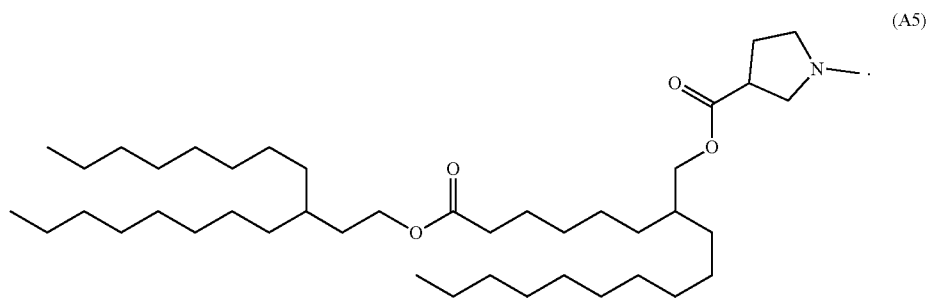 [SMILES: CCCCCCCCCCC(CCCCCC(=O)OCCC(CCCCCCCC)CCCCCCCC)COC(=O)C1CCN(C)C1]
(A5)

8. The compound according to claim 1 represented by formula (A6) below, or a pharmaceutically acceptable salt thereof

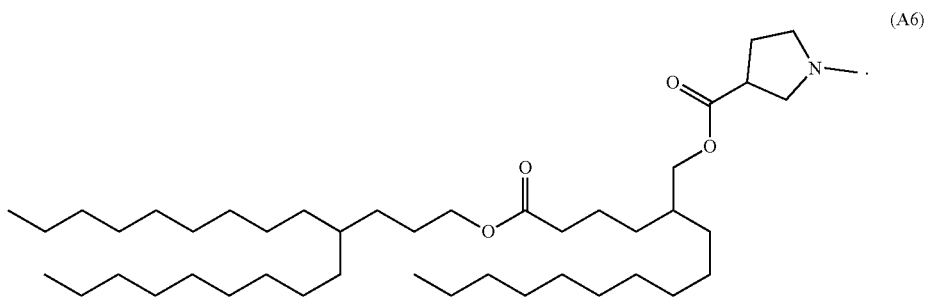 [SMILES: CCCCCCCCCCC(CCCC(=O)OCCCC(CCCCCCCCC)CCCCCCCCC)COC(=O)C1CCN(C)C1]

(A6)

9. The compound according to claim 1 represented by formula (A7) below, or a pharmaceutically acceptable salt thereof

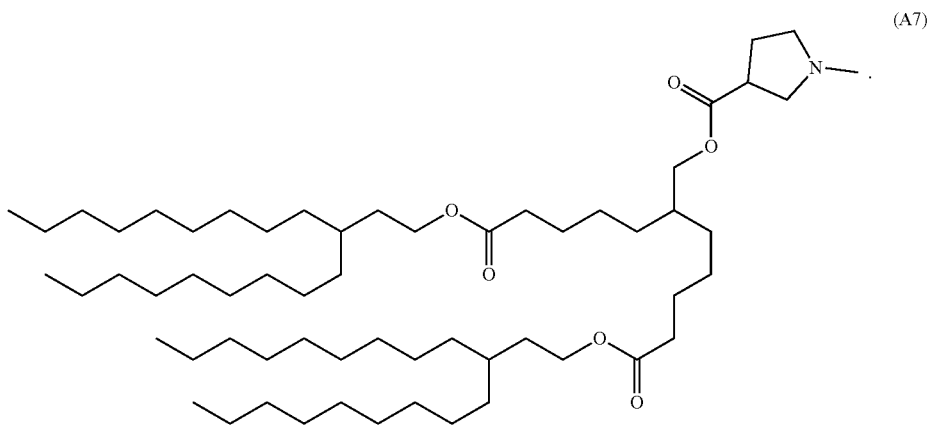 [SMILES: CCCCCCCCCC(CCCCCCCCC)CCOC(=O)CCCCC(CCCCC(=O)OCCC(CCCCCCCCC)CCCCCCCCC)COC(=O)C1CCN(C)C1]

(A7)

10. The compound according to claim 1 represented by formula (A8) below, or a pharmaceutically acceptable salt thereof

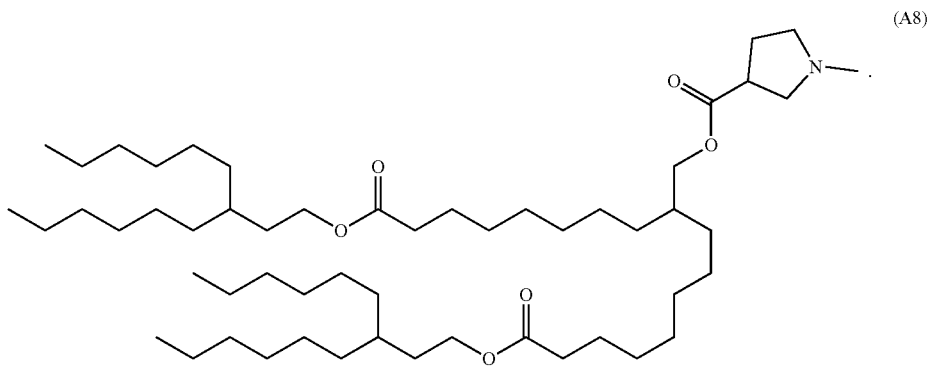 [SMILES: CCCCCCC(CCCCCC)CCOC(=O)CCCCCCCC(CCCCCCCC(=O)OCCC(CCCCCC)CCCCCC)COC(=O)C1CCN(C)C1]

(A8)

11. The compound according to claim 1 represented by formula (A9) below, or a pharmaceutically acceptable salt thereof

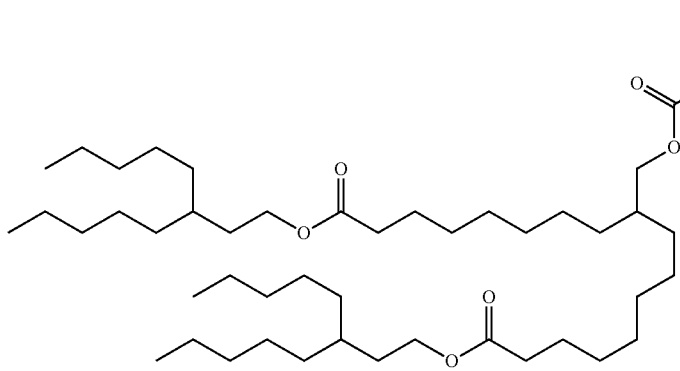

(A9)

12. A lipid complex comprising:
(I) the compound according to claim 1 or a pharmaceutically acceptable salt thereof; and
(II) at least one lipid selected from the group consisting of a neutral lipid, a polyethylene glycol-modified lipid and a sterol.

13. A composition comprising:
(I) the compound according to claim 1 or a pharmaceutically acceptable salt thereof;
(II) at least one lipid selected from the group consisting of a neutral lipid, a polyethylene glycol-modified lipid and a sterol; and
(III) a nucleic acid.

14. A method for producing a composition, the method comprising:
a step of mixing a polar organic solvent-containing aqueous solution containing (I) the compound according to claim 1 or a pharmaceutically acceptable salt thereof, and (II) at least one lipid selected from the group consisting of a neutral lipid, a polyethylene glycol-modified lipid and a sterol with an aqueous solution containing (III) a nucleic acid to obtain a mixed solution; and
a step of reducing a content percentage of the polar organic solvent in the mixed solution.

\* \* \* \* \*

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: #1 sense
<220> FEATURE:
<221> NAME/KEY: misc_difference
<222> LOCATION: (1)..(19)
<223> OTHER INFORMATION: RNA
<220> FEATURE:
<221> NAME/KEY: misc_feature
```

```
<222> LOCATION: (4)..(4)
<223> OTHER INFORMATION: n stands for 2'- fluorouridine
<220> FEATURE:
<221> NAME/KEY: misc_feature
<222> LOCATION: (5)..(5)
<223> OTHER INFORMATION: n stands for 2'- fluorocytidine
<220> FEATURE:
<221> NAME/KEY: misc_feature
<222> LOCATION: (7)..(7)
<223> OTHER INFORMATION: n stands for 2'- fluorouridine
<220> FEATURE:
<221> NAME/KEY: misc_feature
<222> LOCATION: (8)..(8)
<223> OTHER INFORMATION: n stands for 2'- fluorocytidine
<220> FEATURE:
<221> NAME/KEY: misc_feature
<222> LOCATION: (9)..(9)
<223> OTHER INFORMATION: n stands for 2'- fluorouridine
<220> FEATURE:
<221> NAME/KEY: misc_feature
<222> LOCATION: (10)..(10)
<223> OTHER INFORMATION: n stands for 2'- fluorocytidine
<220> FEATURE:
<221> NAME/KEY: misc_feature
<222> LOCATION: (14)..(14)
<223> OTHER INFORMATION: n stands for 2'- fluorouridine
<220> FEATURE:
<221> NAME/KEY: misc_feature
<222> LOCATION: (15)..(15)
<223> OTHER INFORMATION: n stands for 2'- fluorocytidine
<220> FEATURE:
<221> NAME/KEY: misc_feature
<222> LOCATION: (16)..(16)
<223> OTHER INFORMATION: n stands for 2'- fluorouridine
<220> FEATURE:
<221> NAME/KEY: misc_feature
<222> LOCATION: (17)..(17)
<223> OTHER INFORMATION: n stands for 2'- fluorouridine
<220> FEATURE:
<221> NAME/KEY: misc_feature
<222> LOCATION: (19)..(19)
<223> OTHER INFORMATION: n stands for 2'- fluorocytidine
<220> FEATURE:
<221> NAME/KEY: misc_difference
<222> LOCATION: (20)..(21)
<223> OTHER INFORMATION: DNA
<220> FEATURE:
<221> NAME/KEY: misc_binding
<222> LOCATION: (20)..(21)
<223> OTHER INFORMATION: phosphorothioate binding

<400> SEQUENCE: 1
ggannannnn aagnnnnant t                                             21

<210> SEQ ID NO 2
<211> LENGTH: 21
<212> TYPE: DNA
<213> ORGANISM: Artificial Sequence
<220> FEATURE:
<223> OTHER INFORMATION: #1 antisense
<220> FEATURE:
<221> NAME/KEY: misc_difference
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n stands for 2'- fluorouridine
<220> FEATURE:
<221> NAME/KEY: misc_feature
<222> LOCATION: (7)..(7)
<223> OTHER INFORMATION: n stands for 2'- fluorocytidine
<220> FEATURE:
<221> NAME/KEY: misc_feature
<222> LOCATION: (8)..(8)
<223> OTHER INFORMATION: n stands for 2'- fluorouridine
<220> FEATURE:
```

```
<221> NAME/KEY: misc_feature
<222> LOCATION: (9)..(9)
<223> OTHER INFORMATION: n stands for 2'- fluorouridine
<220> FEATURE:
<221> NAME/KEY: misc_feature
<222> LOCATION: (14)..(14)
<223> OTHER INFORMATION: n stands for 2'- fluorouridine
<220> FEATURE:
<221> NAME/KEY: misc_feature
<222> LOCATION: (17)..(17)
<223> OTHER INFORMATION: n stands for 2'- fluorouridine
<220> FEATURE:
<221> NAME/KEY: misc_feature
<222> LOCATION: (18)..(18)
<223> OTHER INFORMATION: n stands for 2'- fluorocytidine
<220> FEATURE:
<221> NAME/KEY: misc_feature
<222> LOCATION: (19)..(19)
<223> OTHER INFORMATION: n stands for 2'- fluorocytidine
<220> FEATURE:
<221> NAME/KEY: misc_difference
<222> LOCATION: (20)..(21)
<223> OTHER INFORMATION: DNA
<220> FEATURE:
<221> NAME/KEY: misc_binding
<222> LOCATION: (20)..(21)
<223> OTHER INFORMATION: phosphorothioate binding

<400> SEQUENCE: 2
gnaagannng agangannnt t                                              21
```